US006331527B1

(12) United States Patent
Parmacek et al.

(10) Patent No.: US 6,331,527 B1
(45) Date of Patent: Dec. 18, 2001

(54) PROMOTER SMOOTH MUSCLE CELL EXPRESSION

(75) Inventors: Michael S. Parmacek, Bryn Mawr, PA (US); Julian Solway, Glencoe, IL (US)

(73) Assignee: Arch Development Corporation, Chicago, IL (US)

(*) Notice: Subject to any disclaimer, the term of this patent is extended or adjusted under 35 U.S.C. 154(b) by 0 days.

(21) Appl. No.: 09/431,349

(22) Filed: Nov. 1, 1999

Related U.S. Application Data

(62) Division of application No. 08/726,807, filed on Oct. 7, 1996
(60) Provisional application No. 60/004,868, filed on Oct. 5, 1995.

(51) Int. Cl.$^7$ .......................... A61K 31/70; A61F 2/06; C07H 21/04; C12N 15/85; C12N 15/86

(52) U.S. Cl. .......................... 514/44; 435/455; 435/456; 536/24.1; 623/1.13; 623/1.41

(58) Field of Search ........................ 514/44; 623/1.13; 623/1.41; 536/24.1; 435/455, 456

(56) References Cited

U.S. PATENT DOCUMENTS 5,837,534    11/1998    Olson et al. .

FOREIGN PATENT DOCUMENTS

| 0666270 | 8/1995 | (EP) . |
|---|---|---|
| WO 94/11506 | 5/1994 | (WO) . |
| WO 94/13824 | 6/1994 | (WO) . |
| WO 96/00006 | 1/1996 | (WO) . |
| WO 96/26742 | 9/1996 | (WO) . |
| WO 97/35974 | 10/1997 | (WO) . |

OTHER PUBLICATIONS

Kemp et al., "Cloning and analysis of the promoter region of the rat SM22 alpha gene," Abstract, *Biochem. J.*, 310:1037–1043, 1995.
Solway et al., "Structure and expression of a smooth muscle cell–specific gene, SM22 alpha," Abstract, *J. Biol. Chem.*, 270(22):13460–13469, 1995.
Aikawa et al., "Human Smooth Muscle Myosin Heavy Chain Isoforms as Molecular Markers for Vascular Development and Atherosclerosis," *Circulation Research*, 73(6):1000–1012, Dec. 1993.
Akira et al., "A nuclear factor for IL–6 expression (NF–IL6) is a member of a C/EBP family," *The EMBO Journal*, 9(6):1897–1906, 1990.
Blank et al., "Elements of the Smooth Muscle α–Action Promoter Required in Cis for Transcriptional Activation in Smooth Muscle," *J. of Biol. Chem.*, 267(2):984–989, Jan. 1992.
Carroll et al., "Structure and Complete Nucleotide Sequence of the Chicken α–Smooth Muscle (Aortic) Actin Gene," *J. of Biol. Chem.*, 261(19):8965–8976, Jul. 1986.

Chang et al., "Cytostatic Gene Therapy for Vascular Proliferative Disorders with a Constitutively Active form of the Retinoblastoma Gene Product," *Science*, 267:518–522, Jan. 1995.
Cserjesi et al., "MHox: a mesodermally restricted homeodomain protein that binds an essential site in the muscle creatine kinase enhancer," *Development*, 115:1087–1101, 1992.
Dalton and Treisman, "Characterization of SAP–1, a Protein Recruited by Serum Response Factor to the c–fos Serum Response Element," *Cell*, 68:597–612, Feb. 1992.
Devlin et al., "Identification of a Muscle–specific Enhancer within the 5'–Flanking Region of the Human Myoglobin Gene," *J. of Biol. Chem.*, 264(23):13896–13901, Aug. 1989.
Dierks et al., "Three Regions Upstream from the Cap Site are Required for Efficient and Accurate Transcription of the Rabbit β–Globin Gene in Mouse 3T6 Cells," *Cell*, 32:695–706, Mar. 1983.
Dynan and Tjian, "The Promoter–Specific Transcription Factor Sp 1 Binds to Upstream Sequences in the SV40 Early Promoter," *Cell*, 35:79–87, Nov. 1983.
Edmondson et al., "Analysis of the Myogenin Promoter Reveals an Indirect Pathway for Positive Autoregulation Mediated by the Muscle–Specific Enhancer Factor MEF–2," *Mol. and Cell. Biol. USA*, 12(9):3665–3677, Sep. 1992.
Evans et al., "An erythrocyte–specific DNA–binding factor recognizes a regulatory sequence common to all chicken globin genes," *Proc. Natl. Acad. Sci.*, 85:5976–5980, Aug. 1988.
Fields and Song, "A novel genetic system to detect protein–protein interactions," *Nature*, 340:245–246, Jul. 1989.
Forrester et al., "A Paradigm for Restenosis Based on Cell Biology: Clues for the Development of New Preventive Therapies," *JACC*, 17(3):758–769, Mar. 1991.
Frid et al., "Myosin Heavy–Chain Isoform Composition and Distribution in Developing and Adult Human Aortic Smooth Muscle," *J. Vasc. Res.*, 30:279–292, 1993.
Gimona et al., "Smooth muscle specific expression of calponin," *FEBS*, 274(1,2):159–162, Nov. 1990.
Gorski et al., "Molecular Cloning of a Diverged Homeobox Gene That is Rapidly Down–Regulated during the $G_0/G_1$ Transition in Vascular Smooth Muscle Cells," *Mol. and Cell. Biol.*, 13(6):3722–3733, Jun. 1993.
Gossett et al., "A New Myocyte–Specific Enhancer–Binding Factor That Recognizes a Conserved Element Associated with Multiple Muscle–Specific Genes.," *Mol. and Cell. Biol.*, 9(11):5022–5033, Nov. 1989.

(List continued on next page.)

*Primary Examiner*—Terry McKelvey
(74) *Attorney, Agent, or Firm*—Fulbright & Jaworski, LLP

(57) ABSTRACT

Disclosed is a smooth muscle cell specific promoter, the SM22α gene promoter as well as the murine cDNA and genomic SM22α nucleic acid sequences. Also disclosed are methods of preventing restenosis following balloon angioplasty and methods of treating asthma based on inhibition of smooth muscle cell proliferation by expressing cell cycle control genes, or contraction inhibiting peptides in smooth muscle cells, under the control of the SM22α promoter.

75 Claims, 21 Drawing Sheets

OTHER PUBLICATIONS

Gottesdiener et al., "Isolation and Structural Characterization of the Human 4F2 Heavy–Chain Gene, and Inducible Gene Involved in T–Lymphocyte Activation," *Mol. and Cell. Biol.*, 8(9):3809–3819, Sep. 1988.

Grepin et al., "A Hormone–Encoding Gene Identifies a Pathway for Cardiac but Not Skeletal Muscle Gene Transcription," *Mol. and Cell. Biol.*, 14(5):3115–3129, May 1994.

Grueneberg et al., "Human and Drosophila Homeodomain Proteins That Enhance the DNA–Binding Activity of Serum Response Factor," *Science*, 257:1089–1095, Aug. 1992.

Gustafson et al., "Interaction of Nuclear Proteins with Muscle–Specific Regulatory Sequences of the Human Cardiac α–Actin Promoter," *Mol. and Cell. Biol.*, 8(10):4110–4119, Oct. 1988.

Gualberto et al., "Functional Antagonism Between YY1 and the Serum Response Factor," *Mol. and Cell. Biol.*, 12(9):4209–4214, Sep. 1992.

Hasty et al., "Muscle deficiency and neonatal death in mice with a targeted mutation in the myogenin gene," *Nature*, 364:501–506, Aug. 1993.

Ip et al., "The GATA–4 Transcription Factor Transactivates the Cardiac Muscle–Specific Troponin C Promoter–Enhancer in Nonmuscle Cells," *Mol. and Cell. Biol.*, 14(11):7517–7526, Nov. 1994.

Jones et al., "A Cellular DNA–Binding Protein That Activates Eukaryotic Transcription and DNA Replication," *Cell*, 48:79–89, Jan. 1987.

Jaynes et al., "The Muscle Creatine Kinase Gene is Regulated by Multiple Upstream Elements, Including a Muscle–Specific Enhancer," *Mol. and Cell. Biol.*, 8(1):62–70, Jan. 1988.

Johansen and Prywes, "Serum response factor: transcriptional regulation of genes induced by growth factors and differentiation," *Biochimica et Biophysica Acta*, 1242, 1–10, 1995.

Kadonaga and Tijan, "Affinity purification of sequence–specific DNA binding proteins," *Proc. Natl., Acad. Sci. USA*, 83:5889–5893, Aug. 1986.

Kretsinger, "Structure and Evolution of Calcium–Modulated Proteins," *Critical Reviews in Biochemistry*, CRC Press, 8(1):119–174, Jul. 1980.

Lees–Miller et al., "Isolation and Characterization of an Abundant and Novel 22–kDa Protein (SM22) from Chicken Gizzard Smooth Muscle," *J. of Biol. Chem.*, 262(7):2988–2993, Mar. 1987.

Lee et al., "Displacement of BrdUrd–induced YY1 by serum response factor activates skeletal α–actin transcription in embryonic myoblasts," *Proc. Natl. Acad. Sci.USA*, 89:9814–9818, Oct. 1992.

Lilly et al., "Requirement of MADS Domain Transcription Factor D–MEF2 for Muscle Formation in Drosophila," *Science*, 267:688–693, Feb. 1995.

Martin, et al., "The paired–like homeo box gene MHox is required for early events of skeletogenesis in multiple lineages," *Genes & Development*, 9:1237–1249, 1995.

Lassar et al., "MyoD is a Sequence–Specific DNA Binding Protein Requiring a Region of myc Homology to Bind to the Muscle Creatine Kinase Enhancer," *Cell*, 58:823–831, Sep. 1989.

Liu et al., "Restenosis After Coronary Angioplasty, Potential Biologic Determinants and Role of Intimal Hyperplasia," *Circulation*, 79(6):1374–1387, Jun. 1989.

Miano et al., "Smooth Muscle Myosin Heavy Chain Exclusively Marks the Smooth Muscle Lineage During Mouse Embryogenesis," *Circulation Research*, 75(5):803–812, Nov. 1994.

Min et al., "The 5'–Flanking Region of the Mouse Vascular Smooth Muscle α–Actin Gene Contains Evolutionarily Conserved Sequence Motifs within a Functional Promoter," *J. of Biol. Chem.*, 265(27):16667–16675, Sep. 1990.

Minty and Kedes, "Upstream Regions of the Human Cardiac Actin Gene That Modulate its Transcription in Muscle Cells: Presence of an Evolutionarily Conserved Repeated Motif," *Mol. and Cell. Biol.*, 6(6):2125–2136, Jun. 1986.

Mitchell et al., "Positive and Negative Regulation of Transcription In Vitro: Enhancer–Binding Protein AP–2 is Inhibited by SV40 T Antigen," *Cell*, 50:847–861, Sep. 1987.

Natesan and Gilman, "DNA bending and orientation–dependent function of YY1 in the c–fos promoter," *Genes & Development*, 7:2497–2509, 1993.

Nishida et al., "cDNA cloning and mRNA expression of calponin and SM22 in rat aorta smooth muscle cells," *Gene*, 130:297–302, 1993.

Olson, "MyoD family: a paradigm for development?", *Genes & Development*, 4:1454–1461, 1990.

Orkin, "GATA–Binding Transcription Factors in Hematopoietic Cells," *Blood*, 80(3):575–581, Aug. 1992.

Owens et al., "Expression of Smooth Muscle–specific α–Isoactin in Cultured Vascular Smooth Muscle Cells: Relationship between Growth and Cytodifferentiation," *J. of Cell Biol.*, 102:343–352, Feb. 1986.

Parmacek et al., "A Novel Myogenic Regulatory Circuit Controls Slow/Cardiac Troponin C Gene Transcription in Skeletal Muscle," *Mol. and Cell. Biol.*, 14(3):1870–1885, Mar. 1994.

Parmacek et al., "Identification and Characterization of a Cardiac–Specific Transcriptional Regulatory Element in the Slow/Cardiac Troponin C Gene," *Mol. and Cell. Biol.*, 12(5):1967–1976, May 1992.

Parmacek et al., "The Structure and Regulation of Expression of the Murine Fast Skeletal Troponin C Gene," *J. of Biol. Chem.*, 265(26):15970–15976, Sep. 1990.

Parmacek and Leiden, "Structure and Expression of the Murine Slow/Cardiac Troponin C Gene," *J. of Biol. Chem.*, 264(22):13217–13225, Aug. 1989.

Ross, "The pathogenesis of atherosclerosis: a perspective for the 1990s," *Nature*, 362:801–809, Apr. 1993.

Ross, "Atherosclerosis: A Defense Mechanism Gone Awry," *American J. of Pathology*, 143(4):987–1002, Oct. 1993.

Ross, "The Pathogenesis of Atherosclerosis—An Update," *The New England Journal of Medicine*, 314(8):488–500, Feb. 1986.

Rovner, et al., "Expression of Smooth Muscle and Nonmuscle Myosin Heavy Chains in Cultured Vascular Smooth Muscle Cells," *J. of Biol. Chem.*, 261(31):14740–14745, Nov. 1986.

Rudnicki et al., "MyoD or Myf–5 is Required for the Formation of Skeletal Muscle," *Cell*, 75:1351–1359, Dec. 1993.

Sawtell and Lessard, Cellular Distribution of Smooth Muscle Actins during Mammalian Embryogenesis: Expression of the α–Vascular but not the γ–Enteric Isoform in Differentiating Striated Myocytes, *J. of Cell Biol.*, 109(6, pt. 1):2929–2937, Dec. 1989.

Schwartz et al., "Replication of Smooth Muscle Cells in Vascular Disease," *Circulation Research,* 58(4):427–444, Apr. 1986.

Shanahan et al., "Isolation of Gene Markers of Differentiated and Proliferating Vascular Smooth Muscle Cells," *Circulation Research,* 73(1):193–204, Jul. 1993.

Schwartz et al., "The Restenosis Paradigm Revisited: An Alternative Proposal for Cellular Mechanisms," *JACC,* 20(5):1284–1293, Nov. 1992.

Singh et al., "Molecular Cloning of an Enhancer Binding Protein: Isolation by Screening of an Expression Library with a Recognition Site DNA," *Cell,* 52:415–423, Feb. 1988.

Tapscott and Weintraub, "MyoD and the Regulation of Myogenesis by Helix–Loop–Helix Proteins," *J. Clin. Invest.,* 87:1133–1138, Apr. 1991.

Ueki et al., "Expression of high and low molecular weight caldesmons during phenotypic modulation of smooth muscle cells," *Proc. Natl. Acad. Sci.USA,* 84:9049–9053, Dec. 1987.

Wilkie and Simon, "Cloning Multigene Families with Degenerate PCR Primers," *Methods: A Companion to Methods in Enzymology,* 2(1):32–41, Feb. 1991.

Zanellato et al., "Myosin Isoform Expression and Smooth Muscle Cell Heterogeneity in Normal and Atherosclerotic Rabbit Aorta," *Arteriosclerosis,* 10(6):996–1009, Nov./Dec. 1990.

International Search Report dated Feb. 11, 1998 (PCT/US97/16204)(ARSB:523P).

Li et al., "Expression of the SM22 alpha promoter in transgenic mice provides evidence for distinct transcriptional regulatory programs in vascular and visceral smooth muscle cells," *J Cell Biol.,* 132(5):849–859, 1996.

Moessler et al., "The SM22 promoter directs tissue–specific expression in arterial but nit in venous or visceral smooth muscle cells in transgenic mice," *Development,* 122:2415–2425, 1996.

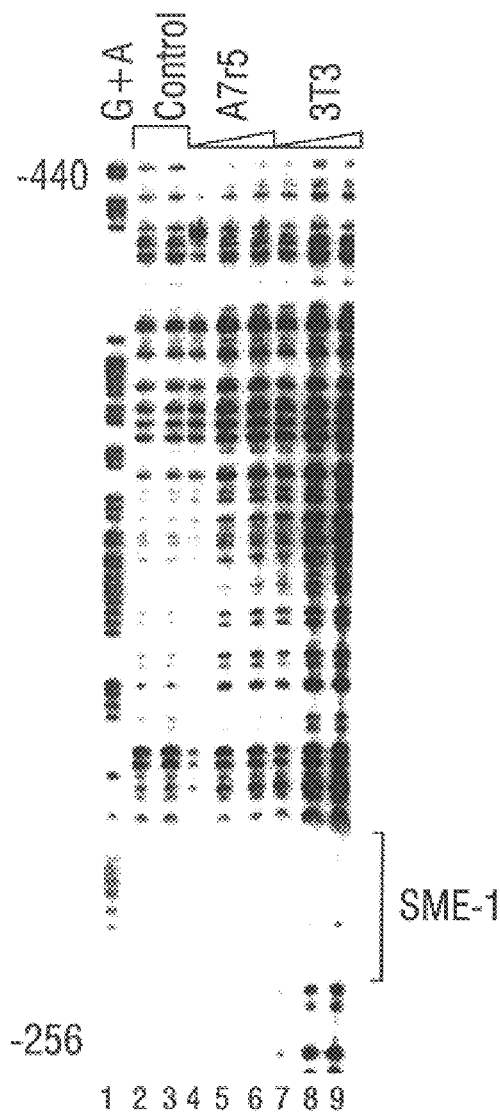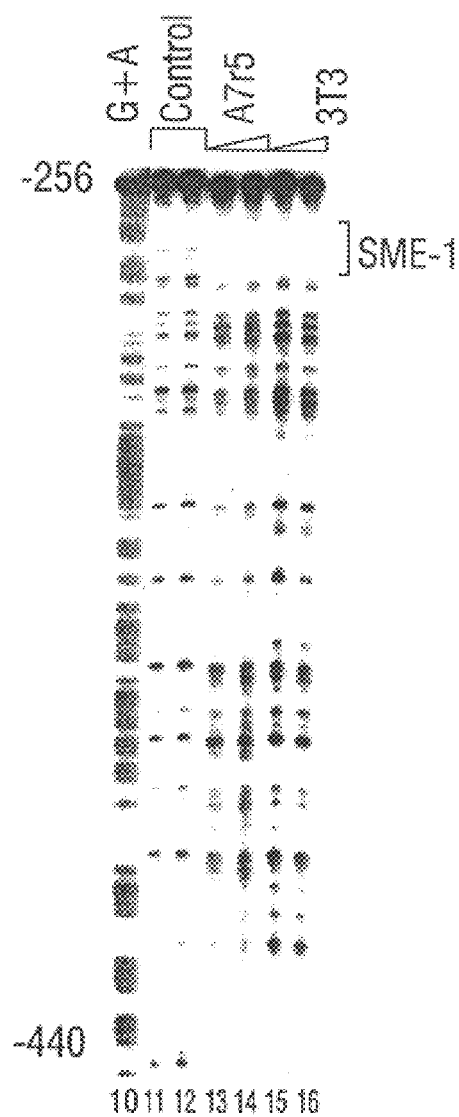
FIG. 3A-1    FIG. 3A-2

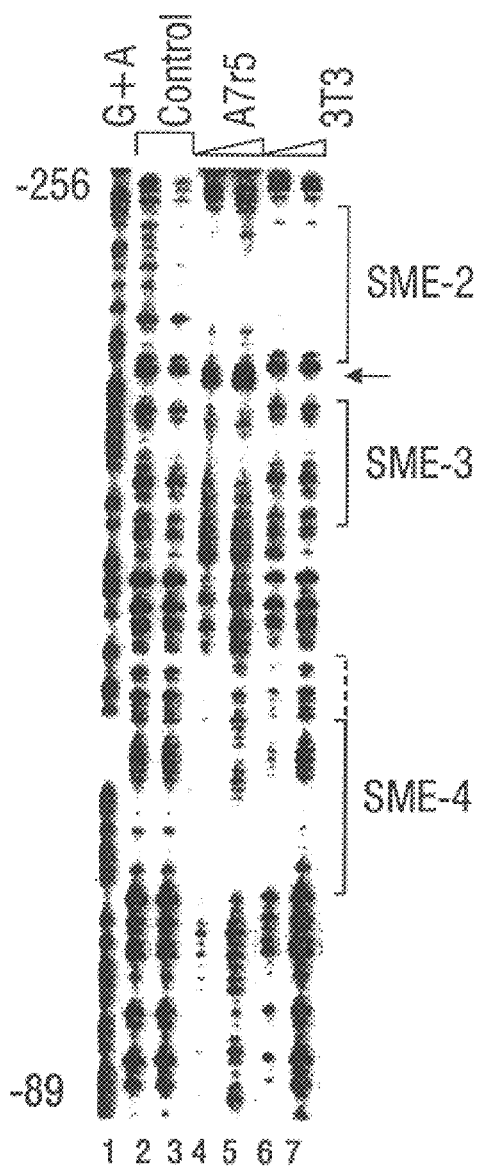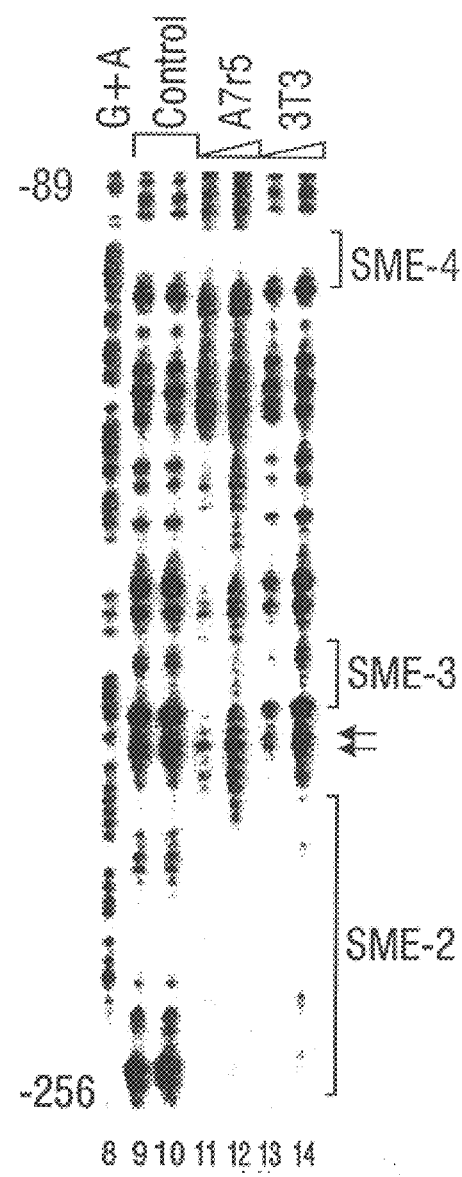
FIG. 3B-1    FIG. 3B-2

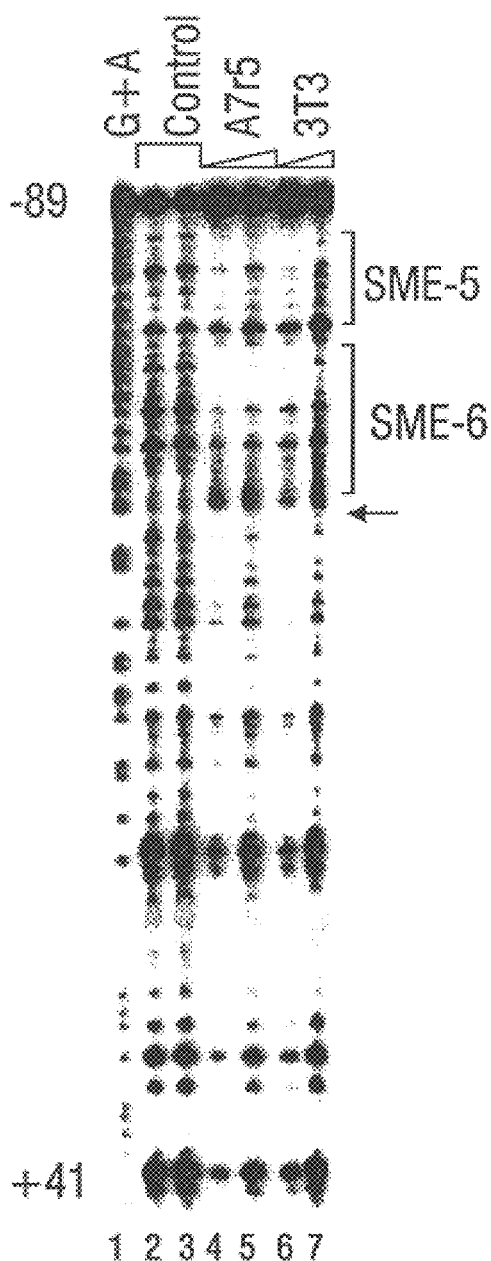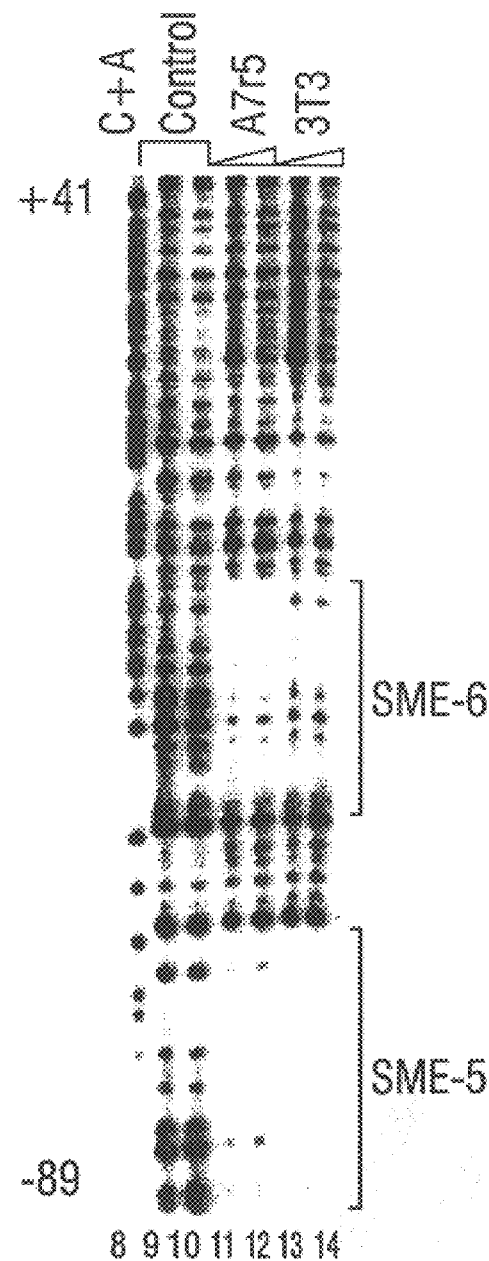
FIG. 3C-1  FIG. 3C-2

```
                                                    -432
AGTCAAGACT AGTTCCCACC AACTCGATTT TAAAGCCTTG CAAGAAGGTG GCTGTTTGT
TCAGTTCTGA TCAAGGGTGG TTGAGCTAAA ATTTCGGAAC GTTCTTCCAC CGAACAAACA

-372                -362        -352        -342        -332        -322
CCCTTGCAGG TTCCTTTGTC GGGCCAAACT CTAGAATGCC TCCCCCTTTC TTTCTCATTG
GGGAACGTCC AAGGAAACAG CCCGGTTTGA GATCTTACGG AGGGGGAAAG AAAGAGTAAC

-312                -302        -292        -282        -272        -262
                                                       SME-1    CArG
AAGAGCAGAC CCAAGTCCGG GTAACAAGGA AGGGTTTCAG GGTCCTGCCC ATAAAAGGTT
TTCTCGTCTG GGTTCAGGCC CATTGTTCCT TCCCAAAGTC CCAGGACGGG TATTTTCCAA

-252                -242        -232        -222        -212        -202
   SME-2              Sp1/AP2                                SME-3
TTTCCGGCC GCCCTCAGCA CCGCCCCCG CCGACCCCCG CAGCATCTCC AAAGCATGCA
AAAGGCCGG CGGGAGTCGT GGCGGGGGCG GGCTGGGGGC GTCGTAGAGG TTTCGTACGT
```

FIG. 3D-1

```
-192              -182              -172
GAGAATGTCT CCGGCT GCCC CCGACAGACT
CTCTTACAGA GGCCGACGGG GCTGTCTGA
         Sp1/AP2

-132              -122              -112
GAGCC TGTGT GGAGTGAGTG GGGCGGCCCG
CTCGGA CACA CCTCACTCAC CCCGCCGGGC
                              SME-6

-72               -62               -52
AGGGAGGGGC GCCAGCGGAC GG CAGAGGGG
TCCCTCCCCG CGGTCGCCTG CC GTCTCCCC

-12               -2
CCTCACCCAG CCGGCGCCCC A
GGAGTGGGTC GGCCGCGGGG T
```

```
                    -162              -152              -142
CCGACAGACT GCTCCAAG TT GGTGTCTTTC CCCAAATATG
GCTGTCTGA CGAGGTTGAA CCACAGAAAG GGGTTTATAC
         SME-4                         CarG

-102              -92               -82
GGGCGGCCCG GGGTGGTGAG CCAAGCAGAC TTCCA TGGGC
CCCGCCGGGC CCCACCACTC GGTTCGTCTG AAGGT ACCCG
                                       SME-5

-42               -32               -22
GG CAGAGGGG TGACATCACT GCCTAGG CGG CCTTTAAACC
CC GTCTCCCC ACTGTAGTGA CGGATCC GCC GGAAATTTGG
         CRE                    TATA
```

FIG. 3D-2

-445 CTGCAGTCAA GACTaG TTCCCACC AAGGGTGG aACTCG ATTTTAAAGCCTTGCAA -399
      GACGTCAGTT CTGATC AAGGGTGG TTGAGc TAAAATTTCGGAACGTT

Potential   Potential         Potential
            Zeste (Z1)  (A-site)          Zeste (Z2)

FIG. 11

PROMOTER SMOOTH MUSCLE CELL EXPRESSION

This is a divisional of co-pending application Ser. No. 08/726,807, filed Oct. 7, 1996, which claims the benefit of priority of U.S. Provisional Application No. 60/004,868, filed Oct. 5, 1995.

The government owns rights in the present invention pursuant to grant numbers R01-HL48257, U01 AI34566 and R01HL51145 from the Public Health Service.

BACKGROUND OF THE INVENTION

1. Field of the Invention

The present invention relates generally to the fields of gene expression, particularly tissue specific expression, and more particularly smooth muscle cell specific expression. The invention also relates to cell proliferation diseases such as atherosclerosis, restenosis following balloon angioplasty and airway blockage in asthma.

2. Description of the Related Art

The phenotypic plasticity of smooth muscle cells (SMCs) permits this muscle cell lineage to subserve diverse functions in multiple tissues including the arterial wall, uterus, respiratory, urinary and digestive tracts. In contrast to fast and slow skeletal muscle cells which fuse and terminally differentiate before expressing contractile protein isoforms, SMCs are capable of simultaneously proliferating and expressing a set of lineage-restricted proteins including myofibrillar isoforms, cell surface receptors and SMC-restricted enzymes. Moreover, in response to specific physiological and pathophysiological stimuli, SMCs can modulate their phenotype by down-regulating a set of contractile protein genes, and in so doing, convert from the so called "contractile phenotype" to a de-differentiated "secretory phenotype" (Mosse et al., 1985; Owens et al., 1986; Rovner et al., 1986; Taubman et al., 1987; Ueki et al., 1987; Belkin et al., 1988; Glukhova et al., 1988; Chaponnier et al., 1990; Gimona et al., 1990; Shanahan et al., 1993).

This phenotypic modulation has been implicated in the pathogenesis of a number of disease states including atherosclerosis and restenosis following coronary balloon angioplasty (Ross, 1986; Schwartz et al., 1986; Zanellato et al., 1990; Ross, 1993; Olson and Klein, 1994) and may also contribute to the airway remodeling seen in asthma (James et al., 1989). Restenosis following coronary balloon angioplasty is a major problem, and contributes to the 40% failure rate of this procedure (Schwartz, et al., 1992; Liu, et al., 1989). Restenosis occurs because the smooth muscle cells are stimulated to proliferate after angioplasty and thus block the arterial wall. Because of restenosis, balloon angioplasty is used mainly for palliation in patients who are not acceptable candidates for open heart surgery (*Scientific American Medicine,* Rubenstein and Federman, Eds., March 1993, Section 1, XII, page 11). A method is needed, therefore, to control or inhibit the proliferation of smooth muscle cells after angioplasty.

In addition, ample evidence demonstrates that airway smooth muscle contraction plays a critical role during acute episodic airflow obstruction in asthma (Knox, 1994; Rodger, 1992; Pueringer and Hunninghake, 1992; Black, 1991). Extra-muscular factors, including submucosal thickening (James et al., 1989), vascular engorgement (Lockhart et al., 1992), periadventitial inflammation (Ingram, 1991), or persistent airway closure with bronchial non-reopening (Gaver et al., 1990), may amplify lumenal narrowing during bronchial smooth muscle constriction. While these factors exacerbate airflow obstruction, it remains airway smooth muscle contraction that is ultimately responsible for the acute decrement of airway caliber. Prevention or reversal of muscular bronchoconstriction has therefore acquired a prominent role in asthma treatment. Because they inhibit force generation by airway smooth muscle, $\beta_2$-adrenergic agonists are recommended in recent NIH guidelines as "the medication of choice for treatment of acute exacerbations of asthma . . . " (National Asthma Education Program, 1991).

Yet, despite their obvious clinical utility, $\beta_2$-adrenergic agonists are-not ideal medicines. Their chronic use has been associated with diminished control of asthma symptoms, due perhaps to receptor down-regulation (Tashkin et al., 1982), to enhanced constrictor hyperresponsiveness following cessation of regular $\beta_2$-adrenergic agonist use (Vathenen et al., 1988), or simply to masking of the underlying inflammatory process. Though controversial (Wanner, 1995), chronic use of potent $\beta_2$-adrenergic agonists might even increase asthma mortality (Crane et al., 1989). Furthermore, wide clinical and laboratory experience (Rossing et al., 1982) demonstrates that inhaled $\beta_2$-adrenergic agonists do not fully prevent acute airway narrowing in response to provocative stimuli. Together, these accumulated data indicate that: 1) inhibition of airway smooth muscle contraction does represent an important facet of the treatment of asthma, but 2) use of $\beta_2$-adrenergic agonists alone to achieve this goal is not the optimal solution.

Relatively little is understood about the molecular mechanisms that control SMC-specific gene expression. Only three smooth muscle cell specific genes have been studied intensively throughout development, SM$\alpha$-actin, SM-myosin heavy chain and calponin-h1. However, of these three, SM$\alpha$-actin and calponin-h1 are expressed in various tissues other than smooth muscle. It is also unfortunate that all three of the smooth muscle genes, SM$\alpha$-actin, SM-myosin heavy chain and calponin-h1 are only expressed in quiescent vascular smooth muscle cells, and not in proliferating cells. Thus, there is still a need for discovery of a smooth muscle cell specific promoter that is not expressed in other types of cells and is constitutively expressed in both quiescent and proliferating cells.

SUMMARY OF THE INVENTION

The present invention seeks to overcome these and other drawbacks in the prior art by providing a promoter specific for expression in smooth muscle cells, and offering the further advantage that the control of expression directed by the promoter is constitutive and cell cycle independent. The promoter of the present invention thus promotes transcription in both resting and proliferating cells, in contrast to other known smooth muscle cell promoters that are down-regulated in proliferating cells. This promoter may be used therefore, to express heterologous proteins or mRNA's in proliferating smooth muscle cells and to control proliferative diseases or to promote angiogenesis, for example.

The invention may be described, in certain embodiments, as an isolated nucleic acid segment comprising an SM22$\alpha$ promoter sequence. The isolated SM22$\alpha$ promoter may be described as the region immediately upstream of the translational start site of the murine SM22$\alpha$ gene. As described herein a nucleic acid segment having a sequence according to bases 899–1382 of SEQ ID NO:1, is also effective to promote transcription in a smooth muscle cell and a nucleic acid segment having that sequence or one that is hybridizable to that sequence under high stringency conditions and further is effective to promote transcription of a heterologous gene in a smooth muscle cell would also fall within the scope of the claimed invention. Such homologous promoters may be isolated from an animal sequence, such as from a mouse, pig, rat, hamster, rabbit or and even a human genome or cDNA library using any of the sequences disclosed herein as a molecular probe. In addition, based on the present disclosure, one of skill might construct such a promoter by splicing elements taken from various sources including, but not limited to, chemically synthesized nucleic acid molecules, or elements removed from other naturally occurring promoters. It is understood that any such promoter, or a promoter having the essential elements of the promoter disclosed herein would be encompassed by the spirit and scope of the invention claimed herein.

The promoter region of the present invention may be defined as comprising that region of the genome immediately upstream (5') of the structural SM22α gene, and controlling expression of that gene. For example, the promoter may comprise the region of up to 30, 40, 50, 100, 500, 1,000, 1,500, 2,000 or even up to 5,000 bases directly upstream of the translational start site of the SM22α gene, and more specifically, an SM22α promoter of the present invention may be described as an isolated nucleic acid segment that comprises a contiguous sequence of bases 1–1381 (−1338 to +41) of SEQ ID NO:1. The designations of −1338 to +41 and the like indicate the position of a base relative to the transcriptional start site (+1), which, in the murine genome, is disclosed herein to be base 1341 of SEQ ID NO:1. The promoter of the present invention may also be described as an isolated nucleic acid segment that comprises a contiguous sequence of bases 899–1381 (−441 to +41) of SEQ ID NO:1. Certain elements of the promoter that are identified in light of the present disclosure are a TATA box 29-bp 5' of the start site, five consensus E boxes/bHLH myogenic transcription factor binding sites located at bps −534, −577, −865, −898, −910, and −1267, three consensus GATA-4 binding sites located at bps −504, −828, −976, two AT-rich, potential MEF-2/rSRF binding sites located at bps −407 and −770 and at least one cis-acting, positive transcriptional regulatory element contained by bp −435 to −416. In addition, the promoter of the present invention contains consensus CArG/SRF binding sites located at bps −150 and −273, one CACC box located at bp −104 and two potential zeste-binding sites, 5' ends at bp −435 and −421, respectively, which are illustrated in FIG. 11, SEQ ID NO:54 and SEQ ID NO:55.

Thus, the promoter of the present invention may comprise some or all of the elements described in the previous paragraph. Such elements may be isolated and recombined by techniques well known in the art to produce a smooth muscle cell specific promoter that may be smaller than the 441 to 482 bases disclosed herein as a minimal sequence required for constitutive smooth muscle cell transcription. It is also known that certain stretches of sequence in the promoter are required for spacing of the cis acting elements and that any sequence that does not impart hairpin loops or other deleterious structural properties may be substituted for those regions so long as the spacing remains the same. It is understood that all such promoters would be encompassed by the present invention.

The isolated nucleic acid segments of the present invention may also be defined as comprising a nucleic acid sequence or even a gene operatively linked to an isolated SM22α promoter sequence. Operatively linked is understood to mean that the gene is joined to the promoter region such that the promoter is oriented 5' to the gene and is of an appropriate distance from the transcription start site, so that the transcription of the gene will be dependent on or controlled by the promoter sequence. The arts of restriction enzyme digestion and nucleic acid ligation to be used in construction of a promoter-gene construct are well known in the art as exemplified by Maniatis et al., *Molecular Cloning, A Laboratory Manual,* Cold Spring Harbor, N.Y., 1982, (incorporated herein by reference). Therefore one would, using standard techniques, prepare a gene by restriction enzyme digestion to have a compatible end sequence, or even a blunt end, to be ligated downstream of the SM22α promoter. The restriction enzyme recognition site may be a naturally occurring sequence, or a sequence generated by site directed mutagenesis, by a PCR™ primer sequence or by any other means known in the art. Alternatively, one might chemically synthesize a gene or gene fragment or an oligonucleotide containing an appropriate restriction enzyme recognition sequence or one-might prepare a gene by any of several methods known in the art.

The gene or nucleic acid segment may be, for example, a structural gene that encodes a full length protein, a portion or part of a protein, or a peptide that one desires to express in a smooth muscle cell. The gene may also encode an RNA sequence, such as an antisense oligonucleotide sequence, or even a regulatory sequence that affects the expression of another gene or genes. In certain preferred embodiments of the invention, the gene will be a cell cycle control gene, such as a retinoblastoma (Rb) gene, p53, a cell cycle dependent kinase, a CDK kinase, a cyclin, a cell cycle regulatory protein, an angiogenesis gene such as VEGF, or any other gene, the expression of which will affect proliferation of the smooth muscle cells in which the gene is expressed, or will effect the growth of new blood vessels. Alternatively, the nucleic acid segment may encode an antisense RNA effective to inhibit expression of a cell cycle control gene or regulatory element Antisense constructs are oligo- or polynucleotides comprising complementary nucleotides to the control regions or coding segments of a DNA molecule, such as a gene or cDNA. Such constructs may include antisense versions of both the promoter and other control regions, exons, introns and exon:intron boundaries of a gene. Antisense molecules are designed to inhibit the transcription, translation or both, of a given gene or construct, such that the levels of the resultant protein product are reduced or diminished. Antisense RNA constructs, or DNA encoding such antisense RNAs, may be employed to inhibit gene transcription or translation or both within a host cell, either in vitro or in vivo, such as within a host animal, including a human subject. Of course, the antisense constructs have evident utility in the types of nucleic acid hybridization described herein. The gene may also encode an antigenic sequence and the necessary leader sequence for transport to the cell surface, or it may encode an enzyme, or an intracellular signal protein or peptide, or it may even encode an SM22α gene or SM22α cDNA gene. Particularly preferred is a constitutively active form of the Rb gene product that inhibits cellular proliferation, disclosed in Chang et al., 1995 (incorporated herein by reference).

The present invention may also be described, in certain embodiments, as a recombinant vector that is capable of replication in an appropriate host cell and that comprises an SM22α promoter sequence as disclosed herein, including an SM22α promoter operatively linked to a gene or nucleic acid segment. Preferred vectors include, but are not limited to, a plasmid, a raus sarcoma virus (RSV) vector, a p21 viral vector or an adenoviral vector. In addition, a variety of viral vectors, such as retroviral vectors, herpes simplex virus (U.S. Pat. No. 5,288,641, incorporated herein by reference), cytomegalovirus, and the like may be employed, as described by Miller (1992, incorporated herein by reference). Recombinant adeno-associated virus (AAV) and AAV vectors may also be employed, such as those described in U.S. Pat. No. 5,139,941, incorporated herein by reference. Recombinant adenoviral vectors are currently preferred. Techniques for preparing replication-defective infective viruses are well known in the art, as exemplified by Ghosh-Choudhury & Graham (1987); McGrory et al. (1988); and Gluzman et al. (1982), each incorporated herein by reference. Also preferred are plasmid vectors designed for increased expression such as those described in Tripathy et al., 1996.

A preferred adenovirus used in the practice of the present invention is replication-defective. A preferred replication-defective adenovirus is one that lacks the early gene region E1 or the early gene regions E1 and E3. For example, the foreign DNA of interest, such as the SM22α promoter and gene of the present invention may be inrerted into the region of the deleted E1 and E3 regions of the adenoviral genome. In this way, the entire sequence is capable of being packaged into virions that can transfer the foreign DNA into an injectable host cell. A preferred adenovirus is a type 5 adenovirus and a SM22α promoter and coding sequence are preferably flanked by adenovirus type 5 sequences.

In certain embodiments of the invention, the vector of the present invention is dispersed in a pharmaceutically acceptable solution. Preferred solutions include neutral saline solutions buffered with phosphate, lactate, Tris, and the like. Of course, one will desire to purify the vector sufficiently to render it essentially free of undesirable contaminant, such as defective interfering adenovirus particles or endotoxins and other pyrogens such that it will not cause any untoward reactions in the individual receiving the vector construct. A preferred means of purifying the vector involves the use of buoyant density gradients, such as cesium chloride gradient centrifugation.

The present invention may also be described, in certain embodiments, as a method of expressing a gene in a smooth muscle cell comprising the steps of: obtaining an isolated nucleic acid segment comprising a gene operatively linked to an SM22α promoter region; transferring that nucleic acid segment into a smooth muscle cell; and maintaining the smooth muscle cell under conditions effective to express the gene. The gene may be a heterologous gene or the SM22α gene, for example. In this method of the invention, the SM22α promoter region preferably includes bases −441 to +41 of the SM22α gene (899–1382 of SEQ ID NO:1) or even bases −441 to +1 of the murine SM22α gene (899–1341 of SEQ ID NO:1) and may include up to 5,000 bases of the SM22α promoter. In the practice of this method, the heterologous gene is preferably a reporter gene, a cell cycle control regulatory gene, an angiogenesis gene, an antisense molecule, or it may encode a muscle contraction inhibiting peptide, and may encode an Rb gene product or a peptide having the sequence MIRJCRKK, SEQ ID NO:19. The Rb gene may be the wild type Rb gene or it may be an altered gene such that the gene product is phosphorylation deficient. It is noteworthy that it may not be necessary to collect the gene product in the practice of the present method. For example, if the gene product is a cell cycle regulatory element, or a contraction inhibiting peptide, then the cell itself will be the target of that effect and the utility of the method will not depend on collecting or even on identifying a protein product. However, certain gene products will have utility as markers of gene expression and as useful proteins or peptides produced by a recombinant cell.

In addition, the present invention may be described as a method of inhibiting smooth muscle cell proliferation comprising the steps of: obtaining an isolated nucleic acid segment comprising a cell cycle regulatory gene operatively linked to an SM22α promoter region; transferring the nucleic acid segment into a smooth muscle cell to obtain a transfected cell; and maintaining the smooth muscle cell under conditions effective to express the cell cycle regulatory gene; wherein expression of the cell cycle regulatory gene inhibits proliferation of the smooth muscle cell. In the practice of the method, the cell cycle regulatory gene operatively linked to an SM22α promoter region may comprise a viral vector, a plasmid vector or it may comprise an adenoviral vector. Further, the cell cycle regulatory gene may preferably encode Rb, p53, cell cycle dependent kinase, CDK kinase, cyclin or a constitutively active Rb gene product, or an antisense RNA.

The present invention may also be described in certain broad aspects as a method of preventing restenosis in a subject following balloon angioplasty of either a coronary artery, renal artery, peripheral artery or carotid artery, for example. In addition, the present invention may be described in certain broad embodiments as a method of preventing restenosis in a subject following balloon angioplasty of a vein as would be used in a coronary artery bypass surgery, or other bioprosthetic grafts that might be used in the periphery. This method comprises the steps of obtaining a viral vector comprising a cell cycle regulatory gene operatively linked to an SM22α promoter region dispersed in a pharmaceutically acceptable solution and administering the solution to the subject. The subject may be an animal subject and is preferably a human subject. In the practice of the method, the viral vector is preferably a replication defective adenoviral vector and the gene may preferably encode a constitutively active Rb gene product Rb, p53, cell cycle dependent kinase, CDK kinase, cyclin or a constitutively active Rb gene product.

An aspect of the invention is also a method of screening for identifying smooth muscle cell specific transcriptional control elements and particularly those elements that work in trans. The method as provided herein preferably employs a reporter gene that confers on its recombinant hosts a readily detectable phenotype that is either expressed or inhibited, as the case may be. Generally reporter genes encode (a) a polypeptide not otherwise produced by the host cell; or (b) a protein or factor produced by the host cell but at lower levels; or (c) a mutant form of a polypeptide produced by the host cell. Preferably the gene encodes an enzyme which produces colorimetric or fluorometric change in the host cell which is detectable by in situ analysis and which is a quantitative or semi-quantitative function of transcriptional activation. Exemplary enzymes include esterases, phosphatases, proteases (tissue plasminogen activator or urokinase) and other enzymes capable of being detected by activity that generates a chromophore or a fluorophore as will be known to those of skill in the art.

Examples of such a reporter gene are the *E. coli* β-galactosidase (β-gal) and firefly luciferase genes. The β-gal enzyme produces a color change upon cleavage of the indigogenic substrate, indolyl-β-D-galactoside by cells expressing β-galactosidase. Thus, this enzyme facilitates automatic plate reader analysis of expression directly in microtiter wells containing transformants treated with candidate activators. Also, since the endogenous β-galactosidase activity in mammalian cells ordinarily is quite low, the analytic screening system using β-galactosidase is not hampered by host cell background.

This enzyme offers the further advantage that expression can be monitored in vivo by tissue analysis as described below.

Another class of reporter genes that confers detectable characteristics on a host cell are those that encode polypeptides, generally enzymes, that render their transformants resistant against toxins, e.g., the neo gene, which protects host cells against toxic levels of the antibiotic G418; a gene encoding dihydrofolate reductase, which confers resistance to methotrexate, or the chloramphenicol acetyltransferase (CAT) gene. Other genes for use in the screening assay herein are those capable of transforming hosts to express unique cell surface antigens, e.g. viral env proteins such as HIV gp120 or herpes gD, which are readily detectable by immunoassays.

In certain embodiments, the present invention may be described as a recombinant vector comprising an isolated SM22α promoter positioned adjacent a gene in a position to control expression of the gene. The splicing of nucleic acid sequences is well known in the art as described above and the insertion of such genes into vectors is also well known in the art. The vector of the present invention may be a plasmid, a phagemid, an adenovirus or a retrovirus, for example. The type of vector does not in and of itself define the present invention, and therefore, any vector that can transfer genetic material into a cell to be expressed in that cell will be useful in the present invention. It is also understood that the nucleic acid segments may be transferred into a cell by means such as liposomes, receptor ligand carriers, mechanical means such as electroporation, etc. and that all such embodiments are encompassed within the claimed invention.

However, the recombinant vector of the present invention preferably is a replication deficient adenovirus or a high expression plasmid comprising an SM22α promoter operatively joined to a gene, and wherein the gene is a cell cycle regulatory gene, such as Rb, p53, cell cycle dependent kinase, CDK kinase, cyclin or a constitutively active Rb.

It is understood that the method of inhibiting muscle contraction will have utility in the treatment of palliation of a variety of diseases that arise from muscle cell contraction. Such diseases include, but are not limited to Prinzmetal's angina, Raynaud's phenomenon, migraine headache, a variety of collagen vascular diseases such as ELS, scleroderma, pulmonary hypertension, coronary arterial vasospasm, in contractile disorders of smooth muscle cells in the eye, gut, uterus, bladder, spleen, etc., or even in striated muscle spasms in paralysis victims.

In a certain broad aspect the present invention may be described as a method of promoting angiogenesis in a subject comprising the steps of obtaining a nucleic acid segment comprising an angiogenesis factor gene operatively linked to an SM22α promoter region; and transferring the nucleic acid segment into a smooth muscle cell to obtain a transfected cell; wherein expression of the nucleic acid segment in the smooth muscle cell promotes angiogenesis. In the practice of the method, the smooth muscle cell may be a coronary arterial or venous smooth muscle cell, or it may be a peripheral arterial or venous smooth muscle cell. A preferred angiogenesis factor is VEGF for example. In certain embodiments of the method, the nucleic acid segment comprising an angiogenesis factor gene operatively linked to an SM22α promoter region is contained in a viral or plasmid vector and the vector is administered to a subject. In certain alternate embodiments, the transferring is done ex vivo and the method further comprises the steps of seeding a bioprosthetic graft or stent with the transfected cells to obtain a seeded graft or stent; and placing the seeded graft or stent into a coronary-or peripheral artery or vein of a subject.

The present invention may also be described in certain broad aspects as a method of inhbiting smooth muscle proliferation comprising the steps of obtaining a nucleic acid segment comprising a cell cycle regulatory gene operatively linked to an SM22α promoter region; transferring the nucleic acid segment into a primary smooth muscle cell ex vivo to obtain a transfected cell; seeding a bioprosthetic graft or stent with the transfected cell to obtain a seeded graft or stent; and placing the seeded graft or stent into a coronary or peripheral artery or vein of a subject, wherein expression of the cell cycle regulatory gene inhibits proliferation of a smooth muscle cell.

Nucleic Acid Hybridization

The nucleic acid sequences disclosed herein will also find utility as probes or primers in nucleic acid hybridization embodiments. As such, it is contemplated that oligonucleotide fragments corresponding to the sequence of SEQ ID NO:1 for stretches of between about 10 nucleotides to about 20, for example, oligonucleotides of 11, 12, 13, 14, 15, 16, 17, 18 or 19 nucleotides, or up to about 30 nucleotides inclusive of all sizes from 20 to 30 inclusive will find particular utility. It is also understood that even longer sequences, e.g., up to 40, 50, 100, and even up to full length, being more preferred for certain embodiments. In addition, the sequences, particularly intron sequences, disclosed herein as SEQ ID NO:2 and SEQ ID NO:6 will find utility as probes and primers for the discovery and isolation of related sequences. The ability of such nucleic acid probes to specifically hybridize to SM22α genomic sequences will enable them to be of use in a variety of embodiments. For example, the probes can be used in a variety of assays for detecting the presence of complementary sequences in a given sample. However, other uses are envisioned, including the use of the sequence information for the preparation of mutant species primers, or primers for use in preparing other genetic constructions.

Nucleic acid molecules having stretches of 10, 20, 30, 50, or even of 100 nucleotides or so, complementary to SEQ ID NO:1, SEQ ID NO:2 and SEQ ID NO:6 will have utility as hybridization probes. These probes will be useful in a variety of hybridization embodiments, such as Southern and northern blotting in connection with analyzing SM22α structural or regulatory genes in diverse cell lines and developmental stages and in various species. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 10 and about 100 nucleotides, or even up to 1419 or more according to the complementary sequences one wishes to detect.

The use of a hybridization probe of about 10, 15, or even 17 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. For example, it is well established that a nucleotide of 17 bases is sufficient to selectively hybridize to a target sequence contained in a complex library such as a genomic library, for example, however smaller sequences are useful in less complex applications. Such fragments may be readily prepared by, for example, directly synthesizing the fragment by chemical means, by application of nucleic acid reproduction technology, such as the PCR™ technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of SM22α genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M–0.15M NaCl at temperatures of 50° C. to 70° C. Such conditions would be termed high stringency in that these conditions tolerate little, if any, mismatch between the probe and the template or target strand.

Of course, for some applications, for example, where one desires to prepare mutants employing a mutant primer strand hybridized to an underlying template or where one seeks to isolate SM22α-encoding sequences or promoters from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphate or peroxidase, instead of radioactive or other environmentally undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

The nucleic acid segments of the present invention, may be combined with other DNA sequences, such as polyadenylation signals, additional restriction enzyme sites, multiple cloning sites, coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

It will be understood that this invention is not limited to the particular nucleic acid and amino acid sequences of SEQ ID NO:1–SEQ ID NO:7. Therefore, DNA segments prepared in accordance with the present invention may also encode biologically functional equivalent promoters, proteins or peptides which have variant sequences, but essentially the same function. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

In particular, one may wish to isolate the SM22α promoter from another species such as from a human. As such, one would obtain a human genomic library from a commercial source, or one might create such a library from a human cell. One would then prepare a probe from the sequence of SEQ ID NO:1, for example by labeling the nucleic acid with a radioactive or fluorescent label. The genetic material from a series of clones would then be hybridized to the probe and positive hybridizations would be subjected to a series of more stringent conditions until only a manageable number of positive clones remained to be tested by sequence analysis or by other means known in the art.

Alternatively, one might use a set of oligonucleotides based on the sequences disclosed herein as SEQ ID NO:1 to design primers to be used in the PCR™ to amplify portions of an SM22α promoter, and the amplified DNA would then be used as a hybridization probe as above. The design and use of PCR™ primers is well known in the art and would not require undue experimentation in light of the present disclosure.

The GenBank accession number for the murine SM22α cDNA is L41154. The GenBank accession number for the murine SM22α gene is L41161.

BRIEF DESCRIPTION OF THE DRAWINGS

FIG. 3A-1, FIG. 3A-2, FIG. 3B-1, FIG. 3B-2, FIG. 3C-1, FIG. 3C-2 (Scanned images), FIG. 3D, FIG. 3D-1, and FIG. 3D-2. DNase I footprint analysis of the SM22α arterial SMC-specific promoter. (FIG. 3A-1, FIG. 3A-2, FIG. 3B-1, FIG. 3B-2, FIG. 3C-1, and FIG. 3C-2) Footprint analysis. Three overlapping genomic subfragments (bp −441 to −256 (FIG. 3A-1, FIG. 3A-2), bp −256 to −89 (FIG. 3B-1, FIG. 3B-2), and bp −89 to +41 (FIG. 3C-1, FIG. 3C-2)) spanning the 482-bp (bp −441 to +42) SM22α promoter were subjected to DNase I footprint analyses using nuclear extracts from the SMC line, A7r5 (which express high levels of SM22α mRNA) and NIH 3T3 cells. The sense (left panel) and antisense (right panel) strands of the three genomic subfragments were end-labeled and incubated in the absence (control) or presence of A7r5 and NIH 3T3 (3T3) of nuclear extracts before partial digestion with DNase I (concentrations varied from 5 U/ml to 22.5 U/ml). Standard Maxam and Gilbert purine (G+A) sequencing reactions were run in parallel. The six protected regions identified on both strands with A7r5 nuclear extracts were designated smooth muscle elements (SME-)-1–6, respectively, and are bracketed. DNase I hypersensitive sites are indicated with arrowheads. (FIG. 3D-1, FIG. 3D-2) Nucleotide sequence of the 441-bp SM22α arterial SMC-specific promoter (SEQ ID NOS:52 and 53). The six nuclear protein binding sites identified with A7r5 nuclear extracts are boxed. DNase I hypersensitive sites are indicated by arrowheads.

(FIG. 4A): Identification of nuclear protein complexes that bind to SME-1. Radiolabeled oligonucleotides corresponding to the SME-1 binding site were subjected to EMSAs using 10 μg of nuclear extracts prepared from primary rat aortic SMCs (VSMCs). Some binding reactions included 5–50 ng of the indicated unlabeled competitor oligonucleotides or 1 μl of the indicated antiserum. Three specific complexes were detected and are designated A, B, and C, to the left of the autoradiogram. (FIG. 4B): Identification of nuclear protein complexes which bind to SME-4. EMSAs were performed using a radiolabeled SME-4 oligonucleotide probe as described above. Four specific nuclear protein complexes were detected and are designated A–D to the left of the autoradiogram.

(FIG. 5A) EMSA performed with the radiolabeled SME-5 oligonucleotide probe and nuclear extracts prepared from primary rat aortic SMCs (VSMC), A7r5, WEHI (WE), and 70Z/3 (70Z) cells. Some binding reactions were pre-incubated with 1 μl of the indicated antiserum, or included the indicated unlabeled competitor oligonucleotides. Three nuclear protein complexes were identified and are designated A–C to the left of the autoradiogram. Complex A was ablated and supershifted (dashed arrow) by a-Sp1 antiserum. (FIG. 5B) EMSA performed with the radiolabeled SME-3 oligonucleotide probe and nuclear extracts prepared from primary rat aortic SMCs (VSMC), A7r5(A7) C3H10T½ (10T), NIH 3T3 (3T3), and EL4 cells. Some binding reactions included between 10–75 ng of the indicated unlabeled competitor oligonucleotides. Three specific binding activities, designated A–C, were identified as denoted to the left of the autoradiogram. Nuclear protein complexes that were ablated and supershifted by a-YY1-specific antisera are indicated with arrows to the left of the EMSA. Of note, complex C was present only in nuclear extracts prepared from SMC lineages (arrow). In addition, three unique nuclear protein complexes were present in non-SMC nuclear extracts but not in SMC extracts (dashed arrows).

(FIG. 8A) Effects of mutation of the SME-1/CArG and SME-4/CArG nuclear protein binding sites on SM22α promoter activity in arterial SMCs. (FIG. 8B) Effect of mutation of the SME-2, -3, -5, and -6 sites on SM22α promoter activity in arterial SMCs.

FIG. 11. Sequence analysis of bp −445 to −400, SEQ ID NOS:54 and 55, of the SM22α promoter reveals the presence of 2 potential zeste-binding sites with 5' ends at bp −435 and −421, respectively. Methylation interference assays revealed interference with A7r5 nuclear protein binding at several bases within the 20-bp span from −435 to −416. Protected bases are in bold print. Underlined bases indicate nucleotides that were mutated to determine their effect on nuclear protein binding. A-site designates the portion of the intervening sequence between the zeste-sites (Z1 and Z2) that was also mutated to determine its effect on nuclear protein binding.

DETAILED DESCRIPTION OF THE PREFERRED EMBODIMENTS

Figure 1A:
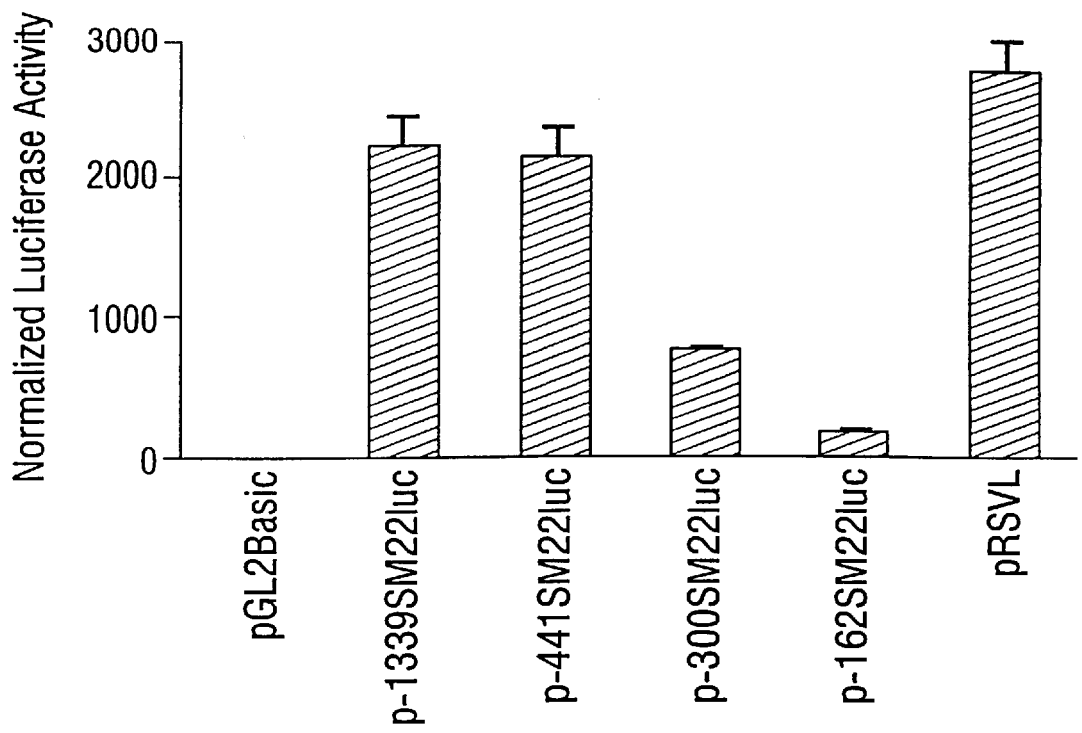
FIG. 1A. Identification and localization of transcriptional regulatory elements that control SM22α gene expression. The data are from transient transfection analyses of SM22α/luciferase reporter plasmids in the smooth muscle cell line, A7r5. 15 mg of SM22α/luciferise reporter plasmid and 5 mg of the pMSVβgal reference plasmid were transiently transfected into replicate cultures of A7r5 cells. Cells were harvested 60 h after transfection, and cell extracts were assayed for both luciferase and β-galactosidase activities. Luciferase activities (light units) were corrected for variations in transfection efficiencies as determined by β-galactosidase activities. Data are expressed as normalized light units ±S.E.M. in the smooth muscle cell line, A7r5.

The present invention arises from the isolation and characterization of a smooth muscle cell specific promoter region that in its naturally occurring state, controls the expression of the SM22α gene. The inventors have shown that this isolated promoter region may be operatively joined to a heterologous structural gene and will control the expression of that gene specifically in smooth muscle cells and other myogenic cell lineages including an embryonic skeletal muscle cell. An important element of the present invention is that, like other known smooth muscle cell promoters, the SM22α promoter is cell cycle independent and is thus not down-regulated when the cell enters the proliferative state. The promoter sequence of the present invention will be useful in the expression of heterologous genes in a smooth muscle cell, in the discovery of trans and cis acting transcriptional control elements that affect smooth muscle cell gene expression and as a probe to isolate SM22α genes and promoters. In particular, the present invention will find use in the prevention of restenosis following balloon angioplasty or other arterial injury, in the promotion of angiogenesis in graft or stent implants and in the treatment or prevention of asthma among other smooth muscle cell proliferative diseases.

SM22α is expressed exclusively in smooth muscle-containing tissues of adult animals and is one of the earliest markers of differentiated smooth muscle cells (SMCs). SM22α is a 6.2 kb single copy gene composed of five exons. SM22α mRNA is expressed at high levels in the aorta, uterus, lung, and intestine, and in primary cultures of rat aortic SMCs, and the SMC line, A7r5. In contrast to genes encoding SMC contractile proteins, SM22α gene expression is not decreased in proliferating SMCs. Transient transfection experiments demonstrated that 441-bp of SM22α 5' flanking sequence was necessary and sufficient to program high level transcription of a luciferase reporter gene in both primary rat aortic SMCs and A7r5 cells. DNA sequence analyses revealed that the 441-bp promoter contains two CArG/SRF boxes, a CACC box, and one potential MEF-2 binding site, cis-acting elements which are each important regulators of striated muscle transcription. Taken together, these studies have identified the murine SM22α promoter as an excellent model system for studies of developmentally regulated, lineage-specific gene expression in SMCs.

As disclosed herein, the murine SM22α cDNA and gene have been isolated and structurally characterized. Using the murine SM22α cDNA as a molecular probe, the tissue distribution and cell cycle-regulated pattern of SM22α gene expression have been defined. In addition, it has been demonstrated that the immediate 5' flanking region of the SM22α gene is necessary and sufficient to direct high-level lineage-restricted expression of the SM22α gene in both primary vascular SMCs and the SMC line, A7r5. Finally, it has been demonstrated that the minimal SM22α promoter lacks a binding site for the bHLH family of myogenic transcription factors. These data are relevant to understanding the underlying transcriptional program that regulates SMC differentiation.

The unique contractile properties of SMCs and their ability to reversibly modulate their phenotype from primarily contractile to primarily synthetic, distinguishes this myogenic lineage from both the skeletal and cardiac muscle cell lineages. However, in contrast to the striated muscle lineages (for review see Olson, 1990; Tapscott et al., 1991; Olson, 1993; Olson et al., 1994), relatively little is currently understood about the cis-acting sequences and trans-acting factors that regulate gene expression in SMCs, due, in part, to the poorly understood lineage relationships of SMCs, which appear to develop from multiple locations throughout the embryo, as well as to the relative paucity of SMC-specific markers (Gonzalez-Crussi, 1971; Lelievre et al., 1975; Murphy et al., 1978; Hirakow et al., 1981; Pardanaud et al, 1989; Poole et al., 1989; Hood et al., 1992). The data disclosed herein demonstrate that the level of SM22α protein expression is regulated at the level of gene expression. However, in contrast to the smooth muscle myosin heavy chain, and possibly the γ-enteric actin gene, which are expressed exclusively in SMCs (Rovner et al., 1986; Sawtell et al. 1989; Aikawa et al., 1993; Frid et al., 1993; Miano et al., 1994), SM22α is expressed in other myogenic cell lineages including the embryonic skeletal muscle cell lineage C2C12. In this regard, it is noteworthy that the SM22α gene is expressed in undifferentiated skeletal myoblasts, which do not express myofibrillar protein isoforms, and that SM22α gene expression is not down-regulated in conjunction with other SMC contractile proteins during serum-induced SMC proliferation. Taken together, these data suggest, that the SM22α gene is not regulated in a coordinated manner with other smooth muscle contractile proteins. Therefore, the isolated SM22α promoter of the present invention contains cis-acting sequences that regulate SM22α gene expression in SMCs and serves as a valuable and unique tool for targeting gene expression to both contractile/arrested and synthetic/proliferative SMCs in the arterial wall in vivo.

This differential pattern of SM22α gene expression in several myogenic lineages suggests that distinct transcriptional programs have evolved to permit the regulated expression of a single gene in multiple cell lineages. However, it is noteworthy that Olson and coworkers (Lilly et al., 1995) recently reported that a null mutation of the MADS box transcription factor D-MEF2 gene in Drosophila resulted in failure of somatic, cardiac and visceral muscles to differentiate. These data suggest that this evolutionarily conserved family of transcription factors may play a critical role in coordinating muscle differentiation across lineages. Thus, it will be of interest to determine the functional role of the A/T-rich potential MEF-2/rSRF (8/10 bp sequence identity) binding site located within the minimal murine SM22α promoter. In this respect, the SM22α promoter may serve as a useful target with which to dissect the functional role of the four individual MEF-2/rSRF family members expressed in vertebrate species (versus the single D-MEF-2 gene in Drosophila) in the smooth muscle lineage. Similarly, two consensus CArG box/SRF binding sites were identified in the minimal SM22α promoter. This motif, which has been identified in multiple skeletal and cardiac-specific transcriptional regulatory elements (Custafson et al., 1988), is also present in the smooth muscle α-actin promoter (Carroll et al., 1988; Min et al., 1990; Blank et al., 1992) suggesting that it may play a role in the coordinate regulation of genes expressed in SMCs. Finally, a consensus CACC box was identified in the minimal SM22α promoter. This nuclear protein binding site is present in multiple skeletal and cardiac-specific transcriptional regulatory elements, where it has been demonstrated to function in conjunction with other lineage-specific nuclear protein binding sites (Parmacek et al., 1990; Parmacek et al., 1994; Jaynes et al., 1988; Devlin et al., 1989; Edmondson et al., 1992).

Another family of transcription factors that have been implicated in SMC development are the homeodomain proteins. In vertebrate species, homeobox proteins are generally involved in morphogenesis and establishment of body plan (reviewed in (Carroll, 1995; Shashikant et al., 1991). The mesoderm-specific homeodomain protein, MHox, which is most closely related to the paired family of homeodomain proteins, is first expressed during murine development in mesodermal cells within the lateral plate mesoderm and visceral arches beginning at day 8.5. Subsequently, it is expressed abundantly in the uterus, heart and skeletal muscle leading to the suggestion that MHox may play a role in SMC (and striated muscle) pattern formation (Cserjesi et al., 1992). However, mice carrying a null mutation in the MHox gene only exhibit defects in skeletal organogenesis resulting from a defect in the formation and growth of chondrogenic and osteogenic precursors (Martin et al., 1995). The finding that only a subset of embryonic structures derived from MHox-expressing cells is affected by this mutation has led to the suggestion that other homeobox proteins expressed in SMCs can functionally substitute for MHox (Gottesdiener et al., 1988). Several potential candidates have been suggested including the closely-related homeobox protein S8 and the more distantly-related homeobox protein Gax, both of which are expressed abundantly in mesodermal derivatives (Gorski et al., 1993; Martin et al., 1995). Finally, it has been suggested that protein-protein interactions between homeodomain proteins and MADS box transcription factors (see above) may modulate the transcriptional activity of the MADS box proteins (Grueneberg et al., 1992). For example, the human MHox homologue Phox1, enhances the DNA-binding activity of SRF in vitro and functionally synergizes with SRF in vivo, suggesting that MHox (or a functionally-related homeodomain protein) could establish cell identity, in part, by determining which genes are activated in response to generic inductive signals which are transduced by ubiquitously-expressed transcription factors such as SRF (Grueneberg et al., 1992).

Current developmental paradigms suggest that tissue-specific gene expression is ultimately regulated by the expression of lineage-specific or lineage-restricted transcription factors (Olson, 1990; Tapscott et al., 1991; Olson, 1993; Olson et al., 1994). Interestingly, sequence analyses of the minimal SM22α promoter failed to reveal a consensus bHLH myogenic transcription factor/E-box binding site. Consistent with this observation, myogenic bHLH family members, including MyoD, myogenin, myf-5 and MRF-4/herculin/myf-6, are not expressed in SMCs and null mutations of the MyoD, myogenin and myf-5 genes, respectively, had no effect on smooth muscle cell specification or differentiation in vivo (Hasty et al., 1993; Rudnicki et al., 1993). Similarly, the minimal SM22α promoter lacked a consensus binding site for GATA-4, a transcription factor that has been demonstrated to transactivate multiple cardiac-specific transcriptional regulatory elements in non-muscle cell lines (Ip et al., 1994; Grepin et al., 1994). Taken together, these studies suggest that potentially novel SMC-specific transcription factors may play a key role in regulating SMC-specific transcription. Future studies utilizing the SM22α promoter as a model system should provide fundamental insight into the molecular mechanisms that regulate SMC-specific transcription and differentiation.

In one aspect, the present invention provides a process of directing and regulating gene expression in a smooth muscle cell. In accordance with that process, a gene operatively joined to an SM22α promoter is delivered to a smooth muscle cell and the smooth muscle cell is then maintained under physiological conditions and for a period of time sufficient for the gene to enter the smooth muscle cell, for the gene to be transcribed and in certain embodiments, for the product of that gene to be expressed. Delivery is preferably by transfection with an a plasmid or a high expression plasmid, adenovirus, p21 virus, raus sarcoma virus, or other virus vector construct capable of transfecting a smooth muscle cell, and comprising an SM22α promoter operatively joined to a coding sequence that encodes the gene product.

The use of adenovirus as a vector for cell transfection is well known in the art. Adenovirus vector-mediated cell transfection has been reported for various cells (Stratford-Perricaudet, et al., 1992). An adenovirus vector of the present invention is replication defective. A virus is rendered replication defective by deletion of the viral early region 1 (E1) region. An adenovirus lacking an E1 region is competent to replicate only in cells, such as human 293 cells, which express adenovirus early region 1 genes from their cellular genome. Thus, such an adenovirus cannot replicate in cells that do not provide the early gene product of the E1 region. In a preferred embodiment, an adenovirus vector used in the present invention is lacking both the E1 and the E3 early gene regions. Thus, it is most convenient to introduce the coding sequence for a gene product at the position from which the E1 and/or E3 coding sequences have been removed (Karlsson et al., 1986). Preferably, the E1 region of adenovirus is replaced by the coding DNA sequence or gene. However, the position of insertion within the adenovirus sequences is not critical to the present invention. Techniques for preparing such replication defective adenoviruses are well known in the art as exemplified by Ghosh-Choudhury et al., McGrory et al., 1988, and Gluzman et al., 1982.

A wide variety of adenovirus vectors can be used in the practice of the present invention. An adenovirus vector can be of any of the 42 different known serotypes of subgroups A–F. Adenovirus type 5 of subgroup C is the preferred staring material for production of a replication-defective adenovirus vector. Adenovirus type 5 is a human adenovirus about which a great deal of biochemical and genetic information is known, and it has historically been used for most constructions employing adenovirus as a vector.

In order to replicate the virus, the vector is cotransfected into 293 cells together with a plasmid carrying the complete adenovirus type 5 genome. Preferred plasmids may also confer ampicillin and tetracycline resistance due to insertion of the appropriate sequences into the virus genome. The molecular strategy employed to produce recombinant adenovirus is based upon the fact that, due to the packaging limit of adenovirus, the plasmid cannot efficiently form plaques on its own. Therefore, homologous recombination between the desired construct and the co-transfected plasmid within a transfected cell results in a viable virus that can be packaged and form plaques only on 293 cells.

Co-transfection is performed in accordance with standard procedures well known in the art. By way of example, 293 cells are cultured in Dulbecco's modified Eagle's medium containing 10% fetal calf serum in a humidified 5% $CO_2$ atmosphere. Confluent 10 cm dishes are split into three 6 cm dishes. On the following day, the cells are cotransfected in calcium phosphate with HeLa DNA as carrier. Six hours after addition of the DNA to the cells, a 15% glycerol stock is used to boost transfection efficiency and the cells are overlaid with 0.65% Noble agar in DMEM containing 2% FCS, 50 mg/ml penicillin G, 10 mg/ml streptomycin sulfate, and 0.25 mg/ml fungizone (GIBCO, Grand Island, N.Y.). Monolayers are incubated for approximately 10 days until the appearance of viral plaques.

These plaques are picked, suspended in DMEM containing 2% FCS, and used to infect a new monolayer of 293 cells. When greater than 90% of the cells show infection, viral lysates are subjected to a freeze/thaw cycle and designated as primary stocks. Recombinant virus with the correct structure is verified by preparation of vital DNA from productively-infected 293 cells, restriction analysis, and Southern blotting. Secondary stocks are subsequently generated by infecting 293 cells with primary virus stock at a multiplicity of infection of 0.01 and incubation until lysis.

The particular cell line used to propagate the recombinant adenoviruses of the present invention is not critical to the present invention. Recombinant adenovirus vectors can be propagated on, e.g., human 293 cells, or in other cell lines that are permissive for conditional replication-defective adenovirus infection, e.g., those which express adenovirus E1 gene products "in trans" so as to complement the defect in a conditional replication-defective vector. Further, the cells can be propagated either on plastic dishes or in suspension culture, in order to obtain virus stocks thereof.

When the vector is to be delivered to an animal subject, a preferred method is to percutaneously infuse an adenovirus vector construct into a blood vessel that perfuses smooth muscle cells (WO 9411506, Barr et al., 1994, both incorporated herein by reference) by intravenous or intra-arterial injection. Methods of delivery of foreign DNA are known in the art, such as containing the DNA in a liposome and infusing the preparation into an artery (LeClerc et al., 1992, incorporated herein by reference), transthoracic injection (Gal et al., 1993, incorporated herein by reference). Other methods of delivery may include coating a balloon catheter with polymers impregnated with the foreign DNA and inflating the balloon in the region of arteriosclerosis, thus combining balloon angioplasty and gene therapy (Nabel et al., 1994, incorporated herein by reference).

After delivery of an adenovinis vector construct to a smooth muscle cell, that cell is maintained under physiological conditions and for a period of time sufficient for the adenovirus vector construct to infect the cardiac cell and for cellular expression of a coding sequence contained in that construct. Physiological conditions are those necessary for viability of the SMOOTH muscle cell and include conditions of temperature, pH, osmolality and the like. In a preferred embodiment, temperature is from about 20° C. to about 50° C., more preferably from about 30° C. to about 40° C. and, even more preferably about 37° C. pH is preferably from a value of about 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other physiological conditions needed to sustain smooth muscle cell viability are well known in the art.

It should also be pointed out that because the adenovirus vector employed is replication defective, it is not capable of replicating in the cells that are ultimately infected. Moreover, it has been found that the genomic integration frequency of adenovirus is usually fairly low, typically on the order of about 1%. Thus, where continued treatment is required, it may be necessary to reintroduce the virus every 6 months to a year. In these circumstances, it may therefore be necessary to conduct long term therapy, where expression levels are monitored at selected intervals.

An adenovirus vector construct is typically delivered in the form of a pharmacological composition that comprises a physiologically acceptable carrier and the adenovirus vector. An effective expression-inducing amount of such a composition is delivered. As used herein, the term "effective expression-inducing amount" means that number of virus vector particles necessary to effectuate expression of a gene product encoded by a coding sequence contained in that vector. Means for determining an effective expression-inducing amount of an adenovirus vector construct are well known in the art. An effective expression-inducing amount is typically from about $10^7$ plaque forming units (pfu) to about $10^{15}$ pfu, preferably from about $10^8$ pfu to about $10^{14}$ pfu and, more preferably, from about $10^9$ to about $10^{12}$ pfu.

As is well known in the art, a specific dose level for any particular subject depends upon a variety of factors including the infectivity of the adenovirus vector, the age, body weight, general health, sex, diet, time of administration, route of administration, rate of excretion, and the severity of the particular disease undergoing therapy.

In that adenovirus is a virus that infects humans, there may be certain individuals that have developed antibodies to certain adenovirus proteins. In these circumstances, it is possible that such individuals might develop an immunological reaction to the virus. Thus, where an immunological reaction is believed to be a possibility, one may desire to first test the subject to determine the existence of antibodies. Such a test could be performed in a variety of accepted manners, for example, through a simple skin test or through a test of the circulating blood levels of adenovirus-neutralizing antibodies. In fact, under such circumstances, one may desire to introduce a test dose of on the order of $1\times10^5$ to $1\times10^6$ or so virus particles. Then, if no untoward reaction is seen, the dose may be elevated over a period of time until the desired dosage is reached, such as through the administration of incremental dosages of approximately an order of magnitude.

In another aspect, the present invention relates to pharmaceutical compositions that may comprise an adenovirus vector gene construct dispersed in a physiologically acceptable solution or buffer. A composition of the present invention is typically administered parenterally in dosage unit formulations containing standard, well known, nontoxic, physiologically acceptable carriers, adjuvants, and vehicles as desired. The term parenteral as used herein includes intravenous, intramuscular, intraarterial injection, or infusion techniques.

Injectable preparations, for example, sterile injectable aqueous or oleaginous suspensions are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminant, such as defective interfering adenovirus particles or endotoxins and other pyrogens such that it will not cause any untoward reactions in the individual receiving the vector construct. A preferred means of purifying the vector involves the use of buoyant density gradients, such as cesium chloride gradient centrifugation.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The following techniques and materials were used in the practice of the examples unless otherwise indicated.

Isolation of Murine SM22α cDNA Clones

The coding region of the murine SM22α cDNA was isolated by performing low stringency PCR™ using murine uterine RNA and synthetic 5' and 3' oligonucleotide PCR™ primers constructed from the previously published sequence of the rat SM22α cDNA (Nishida et al., 1993). The 5' PCR™ primer was constructed to be identical to the first 34-bp of the rat SM22α cDNA with the addition of a 5' EcoRI site (5' AT C G A AT T C C G C TA C T C T C C T T C C A G C-CCACAAACGACCAAGC 3', SEQ ID NO:10). The 3' primer was constructed to include the reverse complement of bp 759 to 782 of the rat SM22α cDNA with an additional 3' HindIII restriction site (5' ATCAAGCTTGGTGG-GAGCTGCCCATGTGCAGTC 3', SEQ ID NO:11). PCR™ reaction products were subcloned into EcoRI/HindIII-digested pGEM7Z (Promega, Madison, Wis.) as described elsewhere (Parmacek et al., 1989). The nucleotide sequence of the murine SM22α cDNA was confirmed by sequencing of the full-length murine SM22α genomic clone. MacVector DNA sequencing software (Kodak/IBI, Rochester, N.Y.) was used for DNA sequence analyses.

To isolate the 3' untranslated region of the SM22α cDNA, $5\times10^5$ recombinant clones from an oligo-(dT) primed λgt11 C2C12 myotube cDNA library were screened with the [$^{32}$P]-labeled murine SM22α cDNA probe (bp 29–811) as described previously (Parmacek et al., 1992). Twelve clones were purified to homogeneity and analyzed by Southern blot analyses as described (Parmacek et al., 1992). Two independent clones, each of which contained a poly(A) tail, were subcloned into EcoRl-digested pGEM7Z and their nucleotide sequences determined. The nucleotide sequence of the 5'-untranslated region was determined from the sequence of the SM22α genomic clone. The 5'-untranslated region was localized on the genomic clone by Southern blot hybridizations, in addition to RNase protection and primer extension analyses as described below.

Isolation of Murine SM22α Genomic Clones

Approximately $1\times10^6$ recombinant phage from a murine 129SV Lambda FIX II genomic library (Stratagene, La Jolla, Calif.) were screened with the 783-bp murine SM22α cDNA probe (bp 29–811) labeled with [α-$^{32}$P]dCTP, and three positive clones were purified to homogeneity as described previously (Pannacek et al., 1992). One clone (SM22-13a) was found to include the entire coding region of the SM22α gene and 9-kb of 5' flanking sequence and was used for all subsequent subcloning and sequencing experiments.

Southern Blot Analyses

High molecular weight DNA was prepared from the tails of strain 129SV mice as described previously (Parmacek et al., 1989). Southern blotting and hybridization to the radiolabeled 783-bp murine SM22α cDNA probe were performed as described previously (Parmacek et al., 1989). Low stringency washing conditions were 2×SSC, 0.1% SDS at 50° C. High stringency washing conditions were 0.1×SSC, 0.1% SDS at 68° C.

Northern Blot Analyses

Tissues were isolated from 12-week old 129SV mice (Jackson Laboratories) as described previously (Parmacek et al., 1989). Animals were housed and cared for according to NIH guidelines in the University of Chicago Laboratory Animal Medicine Veterinary Facility. RNA was prepared from organ samples and from cultures of primary rat aortic SMCs, the rat SMC line A7r5, and non-smooth muscle cell lines including murine NIH 3T3 cells, murine C3H10T½ cells, monkey COS-7 cells, murine C2C12 myoblasts and myotubes, human HepG2 cells, and murine EL-4 cells by the single step guanidinium isothiocyanate protocol (Chomczynski, 1993). Northern blotting was performed using 10 mg of RNA per sample as described previously with the exception that 36 mg/ml of ethidium bromide was added to the RNA resuspension buffer in order to permit quantitation of the 28S and 18S ribosomal RNA subunits in each lane. Probes included the 783-bp (bp 29–811) murine SM22α cDNA and the 754-bp (bp 659–1404) murine calponin cDNA probe. Quantitative image analyses were performed using a Molecular Dynamics PhosphorImager (Sunnyvale, Calif.).

Primer Extension, 5' RACE, and RNase Protection Analyses

A 25-mer oligonucleotide probe constructed to include the reverse complement of base pairs +80 to +104 of the SM22α gene (5' TGCCGTAGGATGGACCCTTGTTGGC 3', SEQ ID NO:12) was 5' end labeled with [$\gamma$-$^{32}$P]ATP and T4 polynucleotide kinase. 40 mg of mouse uterine RNA was hybridized to 2×10$^6$ DPM of labeled probe and primer extension reactions performed at 42° C., 50° C. and 56° C. as described previously (Parmacek et al., 1992). 5' RACE was performed using murine uterine RNA and a synthetic antisense cDNA probe corresponding to bp 234 to 258 of the murine SM22α cDNA according to the manufacturer's instructions (Perkin Elmer, Norwalk, Conn.). RNase protection analyses were performed by subcloning the −441 to +41 murine SM22α genomic subfragment including a synthetic 3' HindIII linker into PstI/HindIII-digested pGEM4Z and performing in vitro transcription of the antisense strand of the genomic subfragment with T7 polymerase of the NcoI-linearized plasmid (NcoI cuts at bp −88 of the genomic clone) in order to obtain an antisense cRNA probe corresponding to bp −88 to +44. Of note, the HindIII linker shares sequence identity with the SM22α cDNA resulting in a cRNA probe with sequence identity initiated at bp +44 (not +41) of the SM22α genomic clone. The 142-bp probe was labeled with [$\alpha$-$^{32}$P]UTP and RNase Protection Analyses were performed using the RPAII™ kit (Ambion, Austin, Tex.) according to the manufacturer's instructions. Antisense cRNA probe radiolabeled by incorporation of α-[$^{32}$P]-UTP is synthesized by in vitro transcription from linearized pBluescriptIIKST7-lacZ, which contains the lacZ gene upstream of the T7 RNA polymerase promoter, using the MaxiScript™ kit (Ambion, Austin, Tex.). Band intensity is quantified by PhosphorImager™, as previously for southern analyses described above.

Cell Culture

The rat cell line A7r5 which was derived from embryonic thoracic aorta was grown in Dulbecco's Modified Essential Media (GIBCO) supplemented with 10% fetal bovine serum (GIBCO) and 1% penicillin/streptomycin. The human hepatocellular carcinoma cell line Hep G2 was grown in Modified Eagle's Medium supplemented with 10% fetal bovine serum and 0.1 mM MEM non-essential ammo acids (GIBCO). Murine lymphoma-derived EL4 cells were grown in Dulbecco's modified Eagle's Media supplemented with 10% horse serum (GIBCO). Murine NIH 3T3 cells, C3H10T½ cells, C2C12 myoblasts and myotubes were grown as described previously (Parmacek et al., 1990: Parmacek et al., 1994). Primary cultures of rat aortic SMCs were isolated from 12–16 week old Sprague Dawley rats (Charles River Laboratories, Wilmington, Mass.) using the method described previously (Chang et al., 1995). Virtually all cells isolated using this method stain positive with anti-smooth muscle actin monoclonal antiserum. In all studies, only early passage (passage 2 or 3) rat aortic SMCs were utilzed. For the cell cycle analyses, SMCs from the third passage were placed in serum-free medium (50% Dulbecco's minimal essential medium (DMEM), 50% Ham's F-12, L-glutamine (292 mg/ml), insulin (5 mg/ml), transferrin (5 mg/ml), selenious acid (5 ng/ml)) for 72 hrs in order to synchronize the cells in $G_0/G_1$ as described previously (Chang et al., 1995). Following 72 hrs of serum starvation, cells were stimulated to proliferate by incubation in medium containing 45% DMEM, 45% Ham's F-12 and 10% FBS. Mouse WEHI B-cells and mouse 70Z/3 pre-B lymphocytes were grown as described previously (Morrisey et al., 1996).

DNase I Footprinting

Nuclear extracts were prepared from the smooth muscle cell line, A7r5 (which express high levels of SM22α mRNA (Solway et al., 1995)) and NIH 3T3 cells as described previously (Parmacek et al., 1992). Three overlapping genomic subeagrents (bp −441 to −256, bp −256 to −89, and bp −89 to +41) spanning the 482-bp SM22α promoter were analyzed. DNase I footprint analyses were performed with 100–150 mg of nuclear extracts prepared from the smooth muscle cell line, A7r5, or NIH 3T3 fibroblasts and the end-labeled sense and antisense strands of the murine SM22α promoter as described previously (Parmacek et al., 1994). Standard Maxam and Gilbert (G+A) sequencing reactions were run in parallel to identify the protected sequences.

Electrophoretic Mobility Shift Assays (EMSAs)

Nuclear extracts were prepared from low passage number primary rat aortic SMCs, A7r5 cells, NIH 3T3 cells, C3H10T½ cells, C2C12 myotubes, WEHI, 70Z/3 and EL4 cells as described by Dignam et al. (Dignam et al., 1983). EMSAs were performed in 0.25×TBE (1×TBE is 100 mM Tris, 100 mM boric acid and 2 mM EDTA) as described previously (Ip et al., 1994). The following complementary oligonucleotides (corresponding to each nuclear protein binding site identified by DNaseI footprint analysis or nuclear protein binding sites containing the specific mutations indicated (mutated nucleotides are underlined)) were synthesized with BamHI and BglII overhanging ends:

SME-1- 5' AAGGAAGGGTTTCAGGGTCCTGCCCAT-
AAAAGGTTTTTCCCGGCCGC 3'           (SEQ ID NO:21);

μSME-1- 5'AAGGAAGGGTTTCAGGGTCCTGCCCAT<u>AGA</u>
<u>TCT</u>TTTTTCCCGGCCGC 3'           (SEQ ID NO:22);

SME-2- 5' CCGCCCTCAGCACCGCCCCGCCCCGAG-
GCCCGCAGCATGTCCG 3'               (SEQ ID NO:23);

μSME-2- 5' CCGCCCTCAGCACCGC
<u>GGATC</u>CCCGACCCCCGCAGCATCT
CCG 3'                            (SEQ ID NO:24);

SME-3- 5' CTCCAAAGCATGCAGAGAATGTCTCCG-
GCTGCCCCCG 3'                     (SEQ ID NO:25);

μSME-3- 5' CTC<u>GGATCC</u>ATGC<u>TAGC</u>AATG<u>AAT</u>
<u>T</u>CGGCTGCCCCCG 3'             (SEQ ID NO:26);

SME-4- 5' TCCAACTTGGTGTCTTTCCCCAAATATG-
GAGCCTGTGTGGAGTG 3'               (SEQ ID NO:27);

μSME-4- 5' TCCAACTTGGTGTCTTTCCCCAA<u>GGAT</u>
<u>CC</u>AGCCTGTGTGGAGTG 3'        (SEQ ID NO:28);

μSRF/SME-4- 5' TCCAACTTGGTGTCTTTCCCC
<u>GG</u>ATATGGAGCCTGTGTGGAGTG 3'  (SEQ ID NO:29);

μYY1/SME-4- 5' TCCAACTTGGTGTCTTTCCCCAAAT
<u>T</u>AGGAGCCTGTGTGGAGTG 3'      (SEQ ID NO:30);

SME-5- 5' GGGCAGGGAGGGGCGCCA
GCG 3'                            (SEQ ID NO:31);

μSME-5- 5' GGGCAGG<u>TA</u>CC<u>G</u><u>AAT</u>TCA
   GCG 3'                                    (SEQ ID NO:32);

SME-6- 5' GGACGGCAGAGGGGTGACATCACTGC-
   CTAGGCGGCCG 3'                            (SEQ ID NO:33);

μCREB/SME-6- 5' GGACGGCAGAGGGG<u>AT</u>CCAT
   G<u>CC</u>TGCCTAGGCGGCCG 3'                (SEQ ID NO:34);

μYY1/SME-6- 5' GGACGGCAGAGGGG
   <u>AT</u>CCATCACTGCCTAGGCGGCCG 3'           (SEQ ID NO:35);

Sp1-5' CTGGCTAAAGGGGCGGGGCTTGGC
   CAGCC 3'                                  (SEQ ID NO:36);

CREB/TCRα-5' CTCCCATTTCCATGACGTCA
   TGGTTA 3'                                 (SEQ ID NO:37).

For cold competition studies, 5 to 100 ng of unlabeled competitor oligonucleotide was included in the binding reaction mixture. For antibody supershift studies, 1 μl of either rabbit preimmune, affinity purified rabbit or mouse IgG (Santa Cruz), α-SRF rabbit polyclonal antiserum (Santa Cruz, sc-335X), α-Sp1 rabbit polyclonal IgG (Santa Cruz, sc-059X), α-YY1 rabbit polyclonal IgG (Santa Cruz, sc-281X), α-CREB-1 mouse monoclonal IgG$_2$ (Santa Cruz, sc-271), α-ATF-1 mouse monoclonal IgA (Santa Cruz, sc-243), α-AP2 rabbit polyclonal IgG (Santa Cruz, sc-184X), or α-GATA-4 rabbit polyclonal IgG (Ip et al., 1994) was incubated with the indicated nuclear extract at 4° C. for 20 minutes prior to the binding reaction as described previously (Ip et al., 1994).

Plasmids

To assess the function of each of the six nuclear protein binding sites identified within the SM22α promoter, a series of SM22α mutant promoter-luciferase reporter plasmids were generated by PCR™-mediated site directed mutagenesis as described previously (Morrisey et al., 1996). The rous sarcoma virus (RSV) LTR-driven luciferase reporter plasmid, pRSVL, and the pMSVβgal reference plasmid have been described previously (Parmacek et al., 1992). The promoterless pGL2-Basic plasmid (Promega, Madison, Wis.) served as the cloning backbone for all of the luciferase reporter plasmids described herein. The p-5000/I1SM22luc plasmid, contains 5-kb of SM22α 5' flanking sequence, the untranslated SM22α first exon, the SM22α first intron and the first 12-bp of exon 2 of the SM22α gene subcloned 5' of the luciferase reporter gene. It was constructed by first subcloning the 8.5 kb BamHI/HindIII SM22α genomic subfragment (containing 5-kb of 5' flanking sequence, exon 1 and 3.5-kb of intron 1) into BglII/HindIII digested pGL2-Basic vector. Next, a 488-bp PCR™-generated HindIII-linkered SM22α genomic subfragment, including at its 5' end the SM22α intron 1 HindIII restriction site (see FIG. 5A), and running to bp +76 of the SM22 cDNA (which includes 12-bp of exon 2) was subcloned into the HindIII-digested vector and its correct orientation (5' to 3' relative to the luciferase reporter gene) confirmed by DNA sequence analysis. The p-5000SM22luc plasmid, containing 5-kb of SM22α 5' flanking sequence subcloned 5' of the luciferase reporter gene, was constructed by first subcloning the 2.2-kb BamHI/EcoRI SM22α genomic subfragment (corresponding to bp −5000 to −2800) into BamHI/EcoRI-digested pBluescript IIKS (Stratagene La Jolla, Calif.). Next, the 1250-bp EcoRI/NcoI SM22α genomic subfragment corresponding to bp −1338 to −89 and the 130-bp PCR™-generated genomic subfragment containing bp −88 (including the NcoI site at its 5' end) to +41 (including a HindIII linker at its 3' end) was ligated into the EcoRI/HindIII-digested vector. Then, the 1.4-kb EcoRI SM22α genomic subfragment (corresponding to bp −2800 to −1339) was subcloned into the EcoRI-digested plasmid and its orientation confirmed by DNA sequence analysis. Finally, the resulting SM22α genomic subfragment corresponding to bp −5 kb to +41 was excised from the Bluescript phagemid with BamHI and HindIII and subcloned into BglII/HindIII-digested pGL2-Basic. The p-1338SM22luc plasmid containing the 1379-bp SM22α genomic subfragment (bp −1338 to +41) subcloned 5' of the luciferase reporter in the pGL2-Basic vector, was constructed using the 1250-bp EcoRI/NcoI SM22α genomic subfragment (bp −1338 to −89) and the 130-bp (bp −88 to +41) PCR™-generated genomic subfragments described herein. The p-441SM22luc plasmid contains the 482-bp (bp −441 to +41) PstI/HindIII SM22α genomic subfragment subcloned into BglII/HindIII-digested pGL2-Basic plasmid. The p-300SM22luc and p-162SM22luc luciferase reporter plasmids, respectively, contain the PCR™-generated bp −300 to +41, and −162 to +41 SM22α genomic subfragments (including synthetic XhoI (5' end) and HindIII (3' end) linkers), subcloned into XhoI/HindIII-digested pGL2-Basic vector. All PCR™-generated genomic subfragments were confirmed by dideoxy DNA sequence analysis.

The following SM22α mutant promoter-luciferase reporter plasmids were generated and named according to the specific nuclear protein binding site (or sites) within the promoter that was mutated (mutated nucleotides within each nuclear protein binding site are underlined):

p-441SM22μSME-1

5' AAGGAAGGGTTTCAGGGTCCTGCCCATA<u>GA</u>
      <u>TCT</u>TTTTTCCCGGCCGC 3'               (SEQ ID NO:38);

p-441SM22μSME-2

5' CCGCCCTCAGCACCGC
      <u>GGAT</u>CCCCGACCCCCGCAGCATCT
      CCG 3'                                 (SEQ ID NO:39);

p-441SM22μSME-3

5' CT<u>CGGAT</u>CCATGC<u>TAG</u>AATG<u>AAT</u>TCGG
      CTGCCCCCG 3'                           (SEQ ID NO:40);

p-441SM22μSME-4

5' TCCAACTTGGTGTCTTTCCCCAA<u>GGAT</u>
      <u>CC</u>AGCCTGTGTGGAGTG 3'              (SEQ ID NO:41);

p-441SM22μSRF/SME-4

5' TCCAACTTGGTGTCTTTCCCC
      <u>GG</u>ATATGGAGCCTGTGTGGAGTG 3'        (SEQ ID NO:42);

p-441SM22μYY1/SME-4

5' TCCAACTTGGTGTCTTTCCCCAAAT
      <u>TA</u>GGAGCCTGTGTGGAGTG 3'            (SEQ ID NO:43);

p-441SM22μSME-5

5' GGGCAGG<u>TA</u>CC<u>G</u><u>AAT</u>TCAGCG 3'  (SEQ ID NO:44);

p-441SM22μCREB/SME-6

5' GGACGGCAGAGGGG<u>AT</u>CCAT<u>GC</u>CTGCC
      TAGGCGGCCG 3'                          (SEQ ID NO:45);

p-441SM22μYY1/SME-6

5' GGACGGCAGAGGGG<u>AT</u>CCATCACTGCC
      TAGGCGGCCG 3'                          (SEQ ID NO:46).

In addition, several SM22α promoter-luciferase reporter plasmids were subcloned that contain mutations in two cis-acting sequences in the SM22α promoter sequence. p-441SM22μCArG contains the mutations described above in the SME-1 and SME-4 sites, and p-441SM22μSME2/5 contains the mutations described above in the SME-2 and SME-5 sites. Each PCR™-generated SM22α promoter mutant was confirmed by DNA sequence analyses as described previously (Parmacek et al., 1992).

To identify functionally important cis-acting elements that control the expression of the SM22α gene in vivo, four transgenic vectors were cloned each of which encodes the bacterial lacZ reporter gene under the transcriptional control of the native or mutated SM22α promoter fragments. The p-5000SM22-lacZ, p-441SM22-lacZ plasmid, the p-441SM22μCArG-lacZ, and p-280SM22-lacZ plasmids, contain the 5-kb SM22α promoter, the 441-bp SM22α promoter, the 441-bp SM22α promoter with mutations in SME-1 and SME-4 (that abolish binding of SRF), and the 280-bp SM22α promoter, respectively, subcloned immediately 5' of the bacterial lacZ reporter gene in a modified pBluescript IIKS (Stratagene) plasmid.

Transfections and Luciferase Assays $1\times10^6$ passage three primary rat aortic SMCs, C2C12 myotubes and A7r5 cells, respectively, were split and plated 24 hours prior to transfection and transfected with either 50 or 100 μg of Lipofectin reagent (Life Technologies, Gaithersburg, Md.), 15 μg of luciferase reporter plasmid and 5 μg of the pMSVβgal reference plasmid as described previously (Parmacek et al., 1992; Ip et al., 1994; Solway et al., 1995; Samaha et al, 1996). $1\times10^6$ NIH 3T3 or COS-7 were transfected with 20 μg of Lipofectin reagent, 15 μg of the luciferase reporter plasmid and 5 μg of the pMSVβgal reference plasmid as described previously (Ip et al., 1994; Forrester et al., 1991). $1\times10^6$ Hep G2 cells were transfected using 360 μg of Lipofectamine reagent (Life Technologies, Gaithersburg, Md.), 26 μg of luciferase reporter plasmid and 9 μg of the pMSVβgal reference plasmid. Following transfection, cell lysates were prepared, normalized for protein content and luciferase and β-galactosidase assays were performed as described previously (Parmacek et al., 1992). All studies were repeated at least three times to assure reproducibility and permit the calculation of standard errors. Luciferase activities (light units) were corrected for variations in transfection efficiencies as determined by assaying cell extracts for β-galactosidase activities. Data are expressed as normalized light units±S.E.M.

Transgenic Mice

Transgenic mice were produced harboring the p-5000SM22-lacZ, p-441SM22-lacZ, p-441SM22μCArG-lacZ and p-280SM22-lacZ transgenes according to standard techniques as described previously (Metzger et al., 1993). To identify transgenic founder mice, Southern blot analysis was performed using the radiolabeled lacZ probe and high molecular weight DNA prepared from tail biopsies of each potential founder. The number of copies per cell were quantitated by comparing the hybridization signal intensity (DPM) to standards corresponding to 1, 10 and 100 copies/cell using a Molecular Dynamics PhosphorImager™. At least four independent founder lines containing each transgene were identified as described previously (Parmacek and Leiden, 1989). Transgenic embryos (less than ED 15.5) and tissue sections from adult mice were fixed, stained for β-galactosidase activity and counter-stained with hematoxylin and eosin as described previously (Lin et al., 1990). Of note, 0.02% NP-40 was added to PBS during the fixation of whole mount embryos. In addition, to visualize the arterial system of mouse embryos, following staining for β-galactosidase activity, embryos were dehydrated in methanol for 24 h and cleared in 2:1 (V/V) benzyl benzoate:benzyl alcohol for 2 h.

EXAMPLE 1

Isolation and Structural Characterization of the Murine SM22α cDNA

Murine SM22α cDNA clones were isolated using the polymerase chain reaction in conjunction with synthetic oligonucleotide primers derived from the previously published sequence of the rat SM22α cDNA (Nishida et al., 1993). The nucleotide sequence of the full-length murine SM22α cDNA is designated herein as SEQ ID NO:8. The murine SM22α cDNA encodes a 201-amino acid polypeptide, SEQ ID NO:9, with a predicted molecular mass of 22.5 kDa. It is composed of a 76-bp 5' untranslated region, a 603-bp open reading frame, and a 403-bp 3' untranslated region. Of note, 23-bp 5' of the poly(A) tail there is an A/T rich sequence (AATATA) which may function as the polyadenylation signal.

A comparison of the coding sequences of the murine and human SM22α cDNAs (Shanahan et al., 1993) demonstrated that the two sequences are 91% and 97% identical at the nucleotide and amino acid levels, respectively. In addition, a comparison of the coding sequences of the murine SM22α cDNA and the murine smooth muscle thin filament regulatory protein, calponin (Strasser et al., 1992), demonstrated that these two sequences are 23% identical and 32% conserved at the amino acid level. Interestingly, the protein sequence encoded by the murine SM22α CDNA exhibits partial sequence identity with the sequence of the Drosophila muscle protein mp20 (Lees-Miller et al., 1987) across the entire cDNA, suggesting that these two proteins may have evolved from a common ancestral gene. Two domains were particularly well conserved between these proteins. One domain with 14/19 amino acid identity (corresponding to amino acids 104–122 of the murine SM22α protein) may represent a calcium binding domain oriented in an EF hand conformation (Kretsinger, 1980). The second C-terminal conserved domain with 13/24 amino acid identity (corresponding to amino acids 158–181 of the murine SM22α protein) is a domain of unknown function.

SM22α is Encoded by a Single Copy Gene

The finding of a putative calcium binding domain oriented in an EF hand conformation suggested that SM22α might be related to other members of the troponin C supergene family of intracellular calcium binding proteins including slow/cardiac troponin C, fast skeletal troponin C, calmodulin, myosin light chain and parvalbumin (Kretsinger, 1980). In order to determine whether SM22α is encoded by a single copy gene in the murine genome and whether SM22α is related to other troponin C supergene family members, the murine SM22α cDNA was used to probe Southern blots containing murine genomic DNA under both high and low stringency conditions. Under high stringency conditions, the murine SM22α cDNA probe hybridized to one or two BamHI, EcoRI, HindIII, PstI and XbaI bands, suggesting that SM22α is a single copy gene in the murine genome. Interestingly, no additional bands were demonstrated under low stringency conditions, suggesting that although the SM22α gene may have one EF hand calcium binding domain, it is not closely related to other members of troponin C supergene family.

EXAMPLE 2

Expression of the SM22α Gene

Previous studies have suggested that SM22α protein is expressed solely in smooth muscle-containing tissues of the adult and may be one of the earliest markers of the smooth muscle cell lineage (Gimona et al., 1992; Duband et al., 1993; Nishida et al., 1993). To determine the in vivo pattern of SM22α gene expression, the SM22α cDNA was hybridized to Northern blots containing RNAs prepared from 12-week old murine tissues. The murine SM22α cDNA probe hybridized to one predominant mRNA species of approximately 1.2-kb. SM22α mRNA is expressed at high levels in the smooth muscle-containing tissues of aorta, small intestine, lung, spleen and uterus. In addition, prolonged autoradiographic exposures revealed very low, but detectable, levels of SM22α mRNA in heart, kidney, skeletal muscle and thymus.

In order to determine the cell-specificity of SM22α gene expression, the SM22α cDNA probe was hybridized to northern blots containing RNAs prepared from rat aortic vascular SMCs, the rat SMC line A7r5, murine NIH 3T3 and C3H10T½ fibroblasts, the SV40-transformed monkey kidney cell line COS-7, murine C2C12 myoblasts and myotubes, the human hepatocellular carcinoma cell line Hep G2 and the murine lymphoid cell line EL4. High levels of SM22α mRNA were detected in primary rat aortic vascular SMCs and the smooth muscle cell line A7r5. Of note, detection of a second 1.5 kb species of mRNA represents cross hybridization of the SM22α probe to the murine calponin mRNA. In addition, SM22α mRNA was expressed in both undifferentiated C2C12 myoblasts and terminally-differentiated C2C12 myotubes. Finally, a faint hybridization signal was detectable in NIH 3T3, C3H10T½, and Hep G2 cells after a 3-day autoradiographic exposure. Quantitative PhosphorImager™ analysis of thee low level hybridization signals revealed that SM22α mRNA is expressed in these three non-myogenic cell lines at less than 1.5% the intensity of SM22α gene expression in A7r5 and primary SMCs. Thus, in addition to primary SMCs and SMC lines, SM22α mRNA is expressed in other embryonic skeletal muscle cell lineages such as C2C12 myoblasts and myotubes, but not in other non-myogenic cell lineages.

SM22α is Expressed in Both Cell Cycle Arrested and Proliferating SMCs

Within the tunica media of the arterial wall the vast majority of vascular SMCs are maintained in a non-proliferating, quiescent state and express contractile proteins (Owens et al., 1986; Rovner et al., 1986; Taubman et al., 1987; Ueki et al., 1987; Gimona et al., 1990; Shanahan et al., 1993; Ross, 1993; Forrester et al., 1991). However, in response to vascular injury, SMCs migrate from the tunica media to the intimal layer, proliferate and assume a "synthetic phenotype" (Ross, 1986; Schwartz et al., 1986; Zanellato et al., 1990; Ross, 1993; Forrester et al., 1991; Schwartz et al., 1992; Liu et al., 1989). Previous studies have demonstrated that many genes encoding vascular SMC contractile proteins are down-regulated during this process (Owens et al., 1986; Rovner et al., 1986; Ueki et al., 1987; Gabbiani et al., 1981). Thus, the SM22α gene may be unique in that its expression is not differentially regulated during progression through the cell cycle. In order to address this question, cultures of low passage number primary rat aortic SMCs were synchronized in the $G_0/G_1$ stage of the cell cycle by serum starvation for 72 hrs. FACS analyses revealed that under these conditions approximately 90% of cells are arrested in $G_0/G_1$ (Chang et al., 1995). The cells were then serum-stimulated and RNA was prepared from replicate cultures at the time of serum stimulation ($t_0$), and at 8 hrs, 12 hrs, 16 hrs, and 24 hrs post-stimulation. After serum stimulation, the arrested vascular SMCs begin to pass through the $G_1/S$ checkpoint of the cell cycle at approximately 12 hrs and by 24 hrs post-stimulation greater than 50% of cells are in the S and $G_2/M$ phases of the cell cycle (Chang et al., 1995). A northern blot analysis demonstrated no differences in SM22α gene expression in cell cycle arrested versus proliferating SMCs as assessed by quantitative PhosphoroImager™ analysis of the hybridization signal. Thus, in contrast to other smooth muscle contractile proteins, such as smooth muscle myosin heavy chain (Rovner et al., 1986), smooth muscle α-actin (Owens et al., 1986) and calponin, SM22α appears to be constitutively expressed at high levels in both quiescent and proliferating vascular SMCs.

EXAMPLE 3

Isolation and Structural Characterization of a SM22α Genomic Clone

A full length murine SM22α genomic clone of 20-kb was isolated by screening a murine 129SV genomic library with a SM22α cDNA probe under high stringency conditions. Exons were identified by hybridization with specific cDNA fragments and their boundaries confirmed by DNA sequence analysis. The nucleic acid sequence of the genomic clone is designated herein as SEQ ID NO:1, containing exon 1, SEQ ID NO:2, containing exons 2, 3 and 4, and SEQ ID NO:6, containing exon 5. There is approximately a 4 kb gap between SEQ ID NO:1 and SEQ ID NO:2, and approximately a 450 base gap between SEQ ID NO:2 and SEQ ID NO:6. The amino acid sequences are encoded by exons 2, 3 and 4 and are designated herein as SEQ ID NO:3, SEQ ID NO:4, SEQ ID NO:5 and SEQ ID NO:7. The murine SM22α gene is composed of five exons spanning 6.2-kb of genomic DNA.

The transcriptional start site of the SM22α gene was identified by RNase protection, primer extension and 5' RACE PCR™ analyses. Primer extension analyses utilizing an antisense synthetic oligonucleotide corresponding to bp 80–104 of the SM22α cDNA resulted in a major extended product of 104-bp (arrow) which was generated at reaction temperatures up to 56° C. In addition, 5' RACE PCR™ was performed utilizing an antisense oligonucleotide primer corresponding to bp 234–258 of the SM22α cDNA. DNA sequence analyses of eight random 5' RACE clones revealed a transcriptional start site 76-bp 5' of the initiation codon in seven of eight clones and 72-bp 5' of the initiation codon in one of eight clones. RNase protection analyses were also performed using an antisense cDNA probe corresponding to bp −88−+44 of the SM22α genomic sequence as deduced by DNA sequence and Southern blot analyses. These analyses revealed a major protected fragment of 44-bp (arrow) corresponding to a transcriptional start site 76-bp 5' of the initiation codon. In addition, a second, minor (20% relative signal intensity) protected fragment of 54-bp was also demonstrated. Taken together, these data allowed the identification of the major transcriptional start site of the murine SM22α gene 76-bp 5' of the initiation codon.

The complete coding sequence and 1339-bp of 5' flanking sequence of the SM22α gene was determined and each of the splice junctions conforms to the consensus splice donor-acceptor patterns as described by Breathnach and Chambon (Breathnach et al., 1981). In order to identify potential transcriptional regulatory elements, 1339-bp of 5' sequence flanking the cap site was searched for a variety of transcriptional regulatory elements using MacVector DNA sequencing software (Kodak/IBI). The nucleotide sequence TTTAAA, (bases 1312 to 1317 of SEQ ID NO:1) which might function as a TATA box was present 29-bp 5' of the start site. A consensus CAAT box was not identified in the immediate 5' flanking region of the SM22α gene. A computer homology search for previously described muscle-specific and/or skeletal or cardiac muscle lineage-restricted transcriptional regulatory elements revealed five consensus E boxes/bHLH myogenic transcription factor binding sites (CANNTG [Olson, 1990; Tapscott et al., 1991; Lassar et al., 1989]) located at bps −534, −577, −865, −898, −910, and −1267, three consensus GATA-4 binding sites (WGATAR [Evans et al., 1988]) located at bps −504, −828, −976, and two AT-rich, potential MEF-2/rSRF binding sites (YTAWAAATAR, SEQ ID NO:13 [Gossett et al., 1989]) located at bps −407 (TTtAAAATcG, SEQ ID NO:14, small letters denote mismatches from the consensus MEF-2 sequence) and −770 (TTcAAAATAG, SEQ ID NO:15). In addition, functionally important nuclear protein binding sites which have been identified in previously characterized skeletal and cardiac-specific transcriptional regulatory elements included two consensus CArG/SRF binding sites (Minty et al., 1986) located at bps −150 and −273 and one CACC box (Dierks et al., 1983) located at bp −104. Finally, four AP2 (CCCMNSSS, SEQ ID NO:16 [Mitchell et al., 1987]), one Sp1 (KRGGCKRRK, SEQ ID NO:17 [Dynan et al., 1983]), and two NF-IL6 (TKNNGNAAK, SEQ ID NO:18 [Akira et al., 1990]) binding sites were located in the 5' flanking region.

EXAMPLE 4

Identification of the cis-Acting Transcriptional Regulatory Elements that Control SM22α Gene Expression In order to identify the functionally important cis-acting sequences that regulate transcription of the SM22α gene in SMCs, a series of transient transfections were performed using SM22α-luciferase reporter constructs and primary rat aortic vascular SMCs and the SMC line, A7r5, both of which express high levels of SM22α mRNA. Transfection of A7r5 cells with the plasmid p-5000/I1SM22luc, containing 5-kb of 5' flanking sequence and the entire 4-kb SM22α intron 1 sequence (the initiation codon is located in exon 2), resulted in a 250–300-fold induction in luciferase activity as compared to the promoterless control plasmid, pGL2-Basic (FIG. 1A, lanes 1 and 2). This level of transcriptional activity was comparable to that obtained following transfection of A7r5 cells with the RSV-containing luciferase reporter plasmid, pRSVL (FIG. 1A, lanes 2 and 8). In order to determine whether this transcriptional activity was due to the immediate 5' flanking region of the SM22α gene, or alternatively, was due to a transcriptional regulatory element located within the first intron of the SM22α gene, the activities of the p-5000/I1SM22luc and p-5000SM22luc plasmid were compared (FIG. 1A, lanes 2 and 3). Transfection of A7r5 cells with the p-5000SM22luc plasmid, containing only 5-kb of 5' flanking sequence, resulted in high-level transcription of the luciferase reporter gene comparable (on a molar basis) to levels obtained with the p-5000/I1SM22luc plasmid. Thus, the 5' flanking region of the SM22α gene contains cis-acting sequence elements required for high-level transcription in A7r5 cells.

Figure 1B:
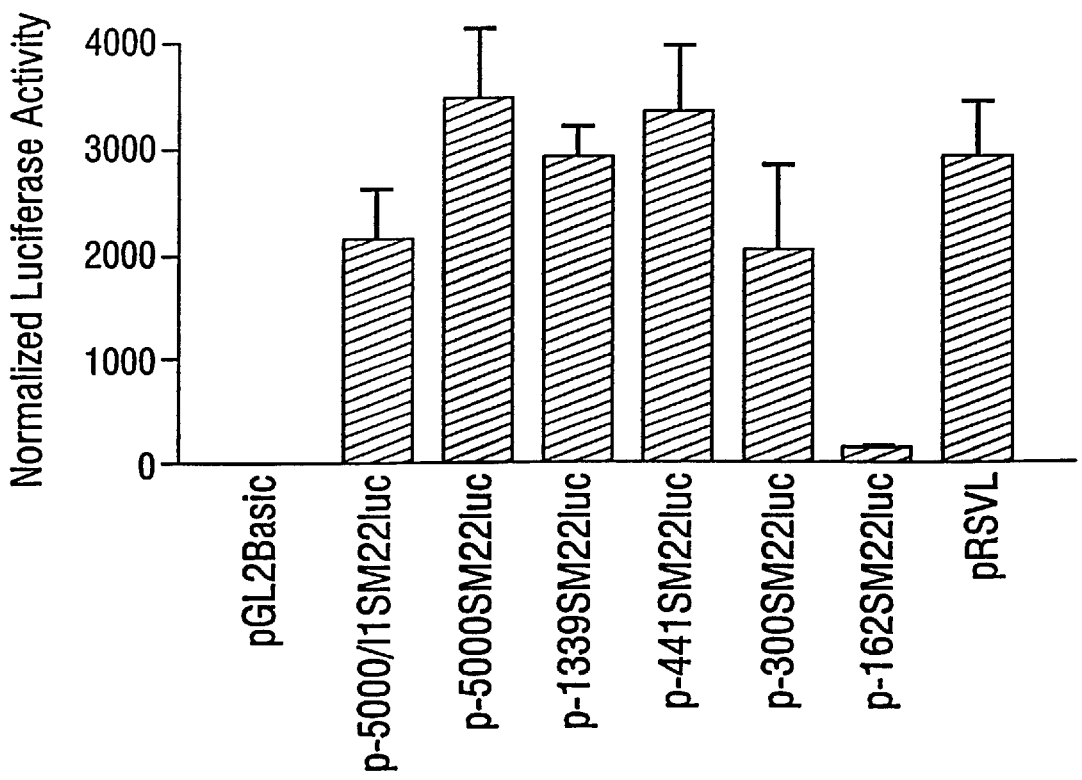
FIG. 1B. Transient transfection analyses of SM22α/luciferase reporter plasmids in primary rat aortic SMCs. Transient transfection analyses were performed using a series of SM22α/luciferase reporter plasmids and primary rat aortic SMCs as described in FIG. 1A. Data are expressed as normalized light units ±S.E.M.

To further localize the 5' flanking elements of the SM22α gene that direct high-level expression in SMCs, a series of 5' deletion mutants were transfected into both A7r5 cells (FIG. 1A) and primary cultured rat aortic vascular smooth muscle cells (FIG. 1B). In both A7r5 cells and primary vascular SMCs, the p-441SM22luc plasmid, containing 441-bp of 5' flanking sequence, increased transcription of the luciferase reporter to levels comparable to the p-5000SM22luc plasmid and the p-1338SM22luc plasmids (FIG. 1A lanes 3, 4, 5 and FIG. 1B lanes 2, 3). However, transfection of both A7r5 cells and primary vascular SMCs with the luciferase reporter plasmids p-300SM22luc and p-162SM22luc containing 300-bp and 162-bp, respectively, of 5' flanking sequence resulted in 50% and 90% reductions in normalized luciferase activities as compared with those obtained with the p-441SM22luc plasmid (FIG. 1A lanes 5, 6, 7 and FIG. 1B lanes 3, 4, 5). These data demonstrated that 441-bp of SM22α 5' flanking sequence, containing the endogenous SM22α promoter, is sufficient to direct high-level transcriptional activity in both A7r5 cells and primary rat aortic SMCs.

EXAMPLE 5

Cellular-Specificity of the SM22α Promoter

Figure 2:
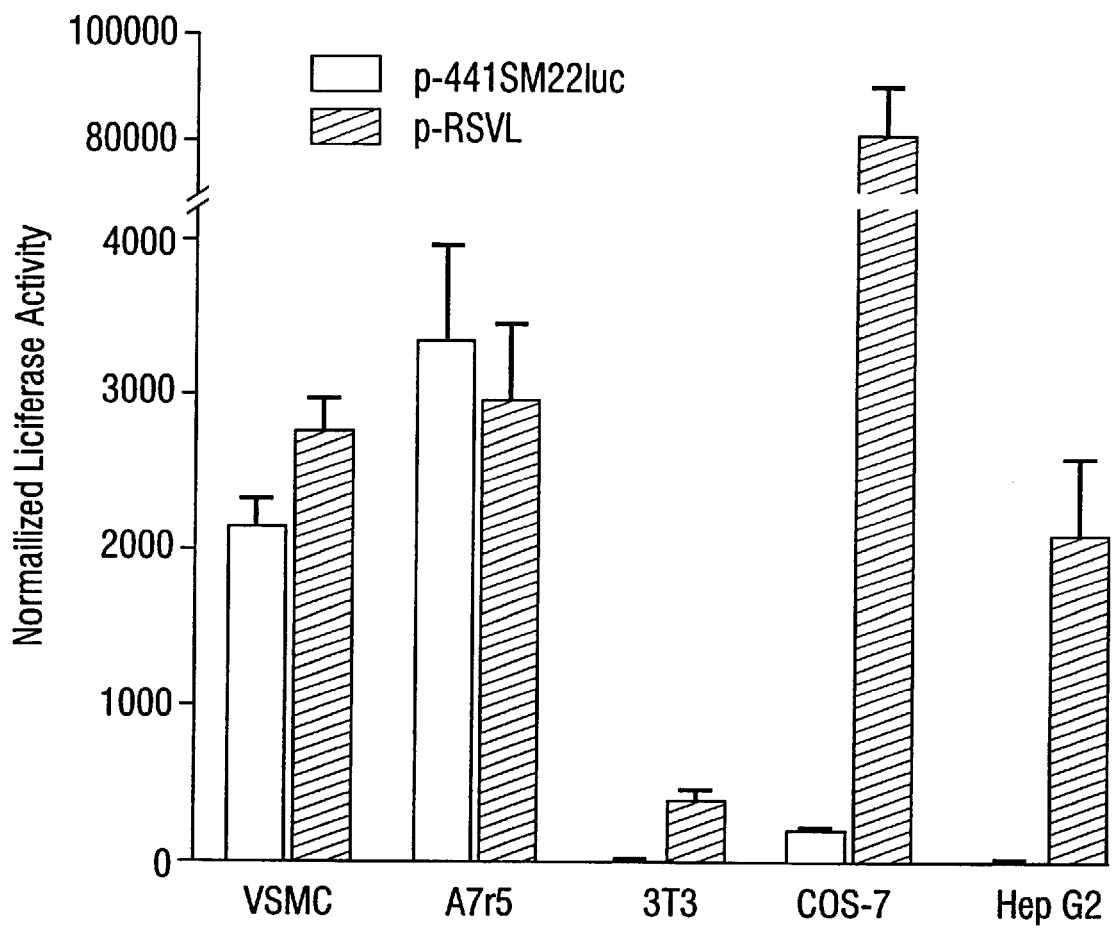
FIG. 2. Cellular-specificity of the 441-bp SM22α promoter. The p-441SM22luc (black bar) and pRSVL (hatched bar) plasmids were transiently transfected into primary rat aortic SMCs (VSMC), A7r5, NIH 3T3 (3T3), COS-7, and Hep G2 cells and the normalized luciferase activities for each respective plasmid was determined as described for FIG. 1A. Data are expressed as normalized luciferase light units ±S.E.M.

In order to characterize the cellular-specificity of the SM22α promoter sequence, the transcriptional activities of the 441-bp SM22α promoter containing plasmid, p-441SM22luc, was compared to the positive control plasmid containing the rous sarcoma virus LTR, pRSVL, in primary rat vascular SMCs, the smooth muscle cell line A7r5, NIH 3T3 fibroblasts, COS-7, and Hep G2 cells. Consistent with the lineage-restricted pattern of SM22α mRNA expression demonstrated in these cell lines, the promoter-containing plasmid, p-441SM22luc, was active in primary rat aortic SMCs and A7r5 cells, increasing transcription of the luciferase reporter gene approximately 2500-fold and 540-fold, respectively, over that induced by tansfection with the promoterless pGL2-Basic plasmid (FIG. 2). This level of promoter activity was comparable to levels obtained following transfection of these cells with the RSV LTR-driven positive control plasmid (FIG. 2). In contrast, the 441-bp SM22α promoter was inactive in NIH 3T3, COS-7 and Hep G2 cells (FIG. 2).

DNA sequence analyses revealed that this 441-bp promoter contains two CArG/SRF boxes (Minty et al., 1986), a CACC box (Dierks et al., 1983), and one A/T-rich, potential MEF-2/rSRF binding site (Gossett et al., 1989), cis-acting elements which have each been demonstrated to be involved in the transcriptional programs that regulate skeletal and cardiac muscle-specific gene expression. However, unlike most previously described skeletal muscle-specific transcriptional regulatory elements, this sequence lacked a canonical E box binding site for the myogenic bHLH transcription factors (Tapscott et al., 1991; Lassar et al., 1989). Thus, the endogenous 441-bp SM22α promoter contains all of the cis-acting sequence elements required to recapitulate the smooth muscle lineage-restricted pattern of SM22α gene expression demonstrated in vivo.

EXAMPLE 6

Generation of SM22α-βgal Transgenic Mice

A reporter construct was first prepared in which the 441-bp minimal SM22α promoter was subcloned immediately 5' of the bacterial β-galactosidase reporter gene (lacZ). The transgenic vector was generated from a pBluescript-KS phagemid containing AscI restriction sites flanking the polylinker sequence. This construct is referred to herein as −441SM22lacZ. The transgene was microinjected into oocytes that were transplanted into pseudo-pregnant hosts as described in Metzger et al., 1993 (incorporated herein by reference). To identify transgenic founder mice, Southern blot analysis was performed using the radiolabeled lacZ probe and high molecular weight DNA prepared from tail snips of each potential founder pup. The radiolabeled lacZ cDNA probe hybridized to the expected 4.2 kb BamHI-digested band in 4 of 17 pups analyzed. The four founders contained between 5 and 160 copies per cell as assessed by comparing the hybridization signal intensity (DPM) to standards corresponding to 1, 10 and 100 copies per cell using a Molecular Dynamics PhosphorImager™.

The F1 –441SM22lacZ #14 male was crossed with a CD-1 female and E11.5 embryos from this litter were isolated, genotyped (using PCR™), fixed and stained for β-galactosidase activity. Transgenic embryos were easily distinguished from their non-transgenic litter mates by the obvious blue staining along their distal somites. This pattern correlated with the transient pattern of SM22α gene expression observed in the developing somites. In ED11.5 embryos, the endogenous SM22α gene is expressed throughout the primitive heart tube, developing somites, dorsal aorta and the forming branch arteries (Li et al., 1996a). Whole mount staining of ED11.5 embryos demonstrated high level β-galactosidase activity throughout the developing arterial system. Blue staining was observed throughout the dorsal aorta, the carotid and vertebral arteries, the cerebral arteries, the umbilical arteries and the aortic arches. A high power section through the iliac artery, demonstrated that expression of the lacZ transgene was restricted to 1–2 layers of cells underlying the arterial endothelium. In addition, β-galactosidase activity was detected within the myotomal component of the developing somites and within the bulbo-truncus region (future outflow tract) and at low levels within the bulbo-cordis region (future right ventricle) of the primitive heart. β-galactosidase activity was not detected within the future left ventricle, left atrium or right atrium at this stage of embryonic development. Surprisingly, although the SM22α gene is expressed at high levels in smooth muscle cells lining the pulmonary airways, as well as within the gastrointestinal and genitourinary tracts, no β-galactosidase activity was detected in the developing lung buds, gastrointestinal mucosa, or the uterine or bladder mucosa during late murine embryogenesis or postnatal development. Thus, the 441 bp SM22α promoter is necessary and sufficient to activate transcription in vascular SMC's in a lineage-restricted fashion in transgenic mice. In addition, this minimal promoter element contains cis-acting sequences required to activate transcription of the SM22α gene in the developing somites. These data also demonstrate that SM22α gene expression is regulated at the level of transcription.

It is noteworthy that the normalized luciferase activity obtained with the 300-bp promoter was still 100-fold above that obtained with promoterless control plasmids in these transient transfection assays. To determine whether a 280-bp SM22α promoter fragment (bp −280–+41) was sufficient to direct arterial SMC-specific gene expression, the inventors produced eight independent lines of transgenic mice in which the lacZ gene was placed under the transcriptional control of the 280-bp SM22α promoter. These mice contained between 2 and 34 copies of the transgene per cell. The 280-bp of 5' flanking sequence was sufficient to direct high level β-galactosidase activity (blue staining) to arterial SMCs and the myotomal component of the somites of ED11.5 mice. Of note, virtually identical patterns of transgene expression were demonstrated in 4 independent lines analyzed at ED11.5 in which copy numbers varied between 2 and 34 copies per cell. Interestingly, dense blue staining was detected within the cardiac outflow tract (a neural crest derivative) while a somewhat patchy pattern of blue staining was present in the developing arterial system (which is derived from lateral mesoderm and neural crest). Higher power sections confirmed that virtually every cell within the cardiac outflow tract stained blue. Interestingly, dense blue staining was detected within the mesenchymal cells that compose the aorticopulmonary spiral septum which is present at ED11.5. In addition, most, but not all, cells underlying the epithelium of the developing arteries stained blue. Taken together, these data demonstrate that the 280-bp SM22α promoter is sufficient to program lineage-restricted transcription in arterial SMCs and the developing somites. However, in contrast to the endogenous pattern of SM22α gene expression, the 441-bp (and 280-bp) SM22α promoter does not contain the cis-acting elements that control SM22α transcription in either visceral (gastrointestinal, uterine, bladder, and bronchial) or venous SMCs nor in the primitive heart tube. Finally, it is noteworthy that the inventors observed virtually the same arterial SMC-specific pattern of expression using the 5000-bp SM22α promoter in transgenic mice. These data strongly suggest that distinct transcriptional programs distinguish tissue-restricted subsets of SMCs (even within the vasculature).

Xgal Tissue Staining

The lung, heart, liver, kidney, spleen, testis or ovary, and skeletal muscle are excised from euthanized animals, and stained to reveal β-galactosidase activity. If β-galactosidase activity is evident in non-transgenic mice, the transgenic lines are generated using a nuclear localizing β-galactosidase isoform to minimize false-positive staining (Hughes and Blau, 1990). To reveal β-galactosidase activity, tissues are washed in PBS, then fixed in 1.25% glutaraldehyde (lung is fixed as below). After washing in $Ca^{+2}$- and $Mg^{+2}$-free buffer, tissues are incubated overnight in the dark in Xgal solution (50 mM Tris HCl pH 7.5, 2.5 mM potassium ferriferrocyanide, 15 mM NaCl, 1 mM $MgCl_2$, 0.5 mg/ml Xgal), then paraffin embedded; 4 micron sections are counterstained with eosin.

Data Analysis

The tissue and cellular distribution of Xgal staining, reflecting SM22α promoter transcriptional activity, is recorded for each transgenic line studied, and compared qualitatively among experimental conditions. Quantitative assessment of lung and tracheal SM22α promoter transcriptional activity is also performed by RNase protection assay for lacZ mRNA, which is compared among study groups using ANOVA followed by multiple range testing. To test whether potential differences in lacZ mRNA levels might stem from different amounts of smooth muscle among groups, airway smooth muscle area vs. circumference curves is compared between groups as described by James et al. (James et al., 1989); pulmonary arterial area vs. circumference curves are likewise compared.

EXAMPLE 7

Expression of SM22α in Lung

SM22α mRNA by is detected in the lungs by in situ hybridization. A digoxigenin-labeled cRNA corresponding to the reverse complement of mouse SM22α cDNA bp 644 to 1007 was prepared by in vitro transcription (MaxiScript™ Kit, Ambion, and Genius™ 4 Kit, Boehringer Mannheim). In situ hybridization was performed on a lung specimen obtained at autopsy from a patient without lung disease. Hybridized probe is detected immunohistochemically with an anti-dioxigenin antibody linked to alkaline phosphatase.

The SM22α cRNA binds selectively to airway smooth muscle and to pulmonary vascular smooth muscle; black anthracotic pigment was also evident in this specimen (typical of urban dwellers).

EXAMPLE 8

Adenovirus Mediated Expression of a Constitutive Rb Gene Product

The Rb protein inhibits cell cycle progression in many mammalian cell types (Hollingsworth et al., 1993), and has been shown to be an important regulator of vascular smooth muscle proliferation (Chang et al., 1995). In its unphosphorylated state, the Rb gene product binds and inactivates certain cellular transcription factors that are required for cell cycle progression (Chen et al., 1989) and upon phosphorylation, the transcription factors are released and the cell progresses through the proliferation cycle. A gene encoding a phosphorylation deficient Rb gene product has been constructed and shown to constitutively inhibit smooth muscle cell cycle proliferation (Chang et al., 1995) when transfected into rat aortic smooth muscle cells in a replication defective adenovirus vector. Further, the Chang et al. (1995) reference also shows that replication deficient adenovirus vectors can be used to express heterologous genes in rat carotid arteries in vivo upon direct exposure of isolated segments of injured artery to the adenovirus. A similar study was done in isolated porcine arteries and again the adenoviral transferred constitutive Rb gene product was shown to be expressed and to inhibit smooth muscle cell proliferation.

The inventors propose that this Rb gene product may also be expressed under the control of the smooth muscle specific promoter disclosed herein, thus directing expression of the Rb gene product specifically in smooth muscle cells. This offers the advantage of administration of the virus vector by a less invasive method such as intravenous injection. It is also contemplated that other cell cycle control gene products, such as p53 for example, would be effective in this method of preventing restenosis.

EXAMPLE 9

Identification of Smooth Muscle Specific Trans-Acting Transcription Factors

Identification of Nuclear Protein Binding Sites in the SM22α Promoter

To identify nuclear protein binding sites within the 441-bp SM22α promoter, DNase I footprint analyses were performed with nuclear extracts prepared from the SMC line, A7r5 (which express high levels of SM22α mRNA (Solway et al., 1995)), and the non-muscle cell line, NIH 3T3. Six nuclear protein binding sites were identified on both the sense and antisense strands with nuclear extracts prepared from the SMC line, A7r5. The six nuclear protein binding sites were designated smooth muscle elements (SME)-1–6, respectively (FIG. 3D). Two footprinted regions, SME-1 (bp −279 to −256) and SME-4 (bp −171 to −136), contain embedded SREs, or CArG boxes (CCWWWWWWGG, SEQ ID NO:47) (FIG. 3D, gray boxes embedded in SME-1 and SME-4), that have been shown previously to bind the MADS box transcription factor, SRF, and play an important role in regulating transcription of the genes encoding skeletal and cardiac α-actin (Minty and Kedes, 1986; Moss et al., 1994; Muscat et al., 1992). Of note, fine differences in the digestion patterns between nuclear extracts prepared from A7r5 and NIH 3T3 cells could be distinguished over the SME-4 site (FIG. 3B, compare lanes 4–5 and 6–7; FIG. 3B, compare lanes 11–12 and 13–14). Several studies suggest that nucleotides embedded within and/or flanking CArG boxes regulate binding of ternary complex factors (TCFs), including members of the ets and homeodomain families of transcription factors. Thus, the finding that a PEA3 motif (bp −295 to −289), which has been demonstrated to bind in vitro to ets family members, lies 23-bp 5' of the SME-1 motif is noteworthy. Similarly, SME-4 spans a GGAG motif (bp −142 to bp −139) which has been demonstrated to bind to TCFs in the ets family of transcription factors (Johansen and Prywes, 1995). Moreover, the SME-4 motif contains the embedded motif ATATGG (bp −146 to bp −141) which has been demonstrated to bind homeobox transcription factors including Csx/Nkx2.5 (Chen et al., 1996).

The SME-2 nuclear protein binding site (bp −249 and bp −216) contains consensus binding motifs for the ubiquitously expressed transcription factors, Sp1 (KRGGCKRRK) (SEQ ID NO:17) and AP2 (CCCMNSSS SEQ ID NO:16) (FIG. 3D, SME-2, gray boxes). Fine differences in the digestion patterns between nuclear extracts prepared from A7r5 and NIH 3T3 cells could be distinguished over this site (FIG. 3B, compare lanes 4–5 and 6–7; FIG. 3B, compare lanes 11–12 and 13–14). The SME-3 nuclear protein binding site (bp −215 to bp −186), which is flanked by DNase I hypersensitive sites at both its 5' and 3' borders, was protected only by nuclear extracts prepared from A7r5 and not by extracts prepared from NIH 3T3 cells (FlG. 3B, compare lanes 4–5 and 6–7; FIG. 3B, compare lanes 11–12 and 13–14). This nuclear protein binding site has not been described previously. The SME-5 nuclear protein binding site (bp −86 to bp −66) once again contains consensus Sp1 and AP2 motifs (FIG. 3C). The SME-6 nuclear protein binding site (bp −59 to −35), lies immediately 5' of the non-consensus TATA box (TTTAA 1312 to 1316 of SEQ ID NO:1), and contains nucleotide sequences that have been demonstrated previously to bind the cyclic AMP response element (CRE) binding proteins (for review see (Lalli and Sassone-Corsi, 1994)) (FIG. 3C). Of note, an AT-rich sequence (bp −408 to −415) with 8/10 bp sequence identity with the consensus MEF2 binding motif (Gossett et al., 1989) was not protected with either A7r5 or NIH 3T3 nuclear extracts. Taken together, these studies demonstrated six nuclear protein binding sites within the murine SM22α promoter (FIG. 3D). Three of these binding sites (SME-2, SME-3 and SME-4) demonstrated differential patterns of digestion when incubated with nuclear extracts prepared form A7r5 and NIH 3T3 cells.

Characterization of Trans-acting Factors that Bind to the SM22α Promoter

Figure 4A:
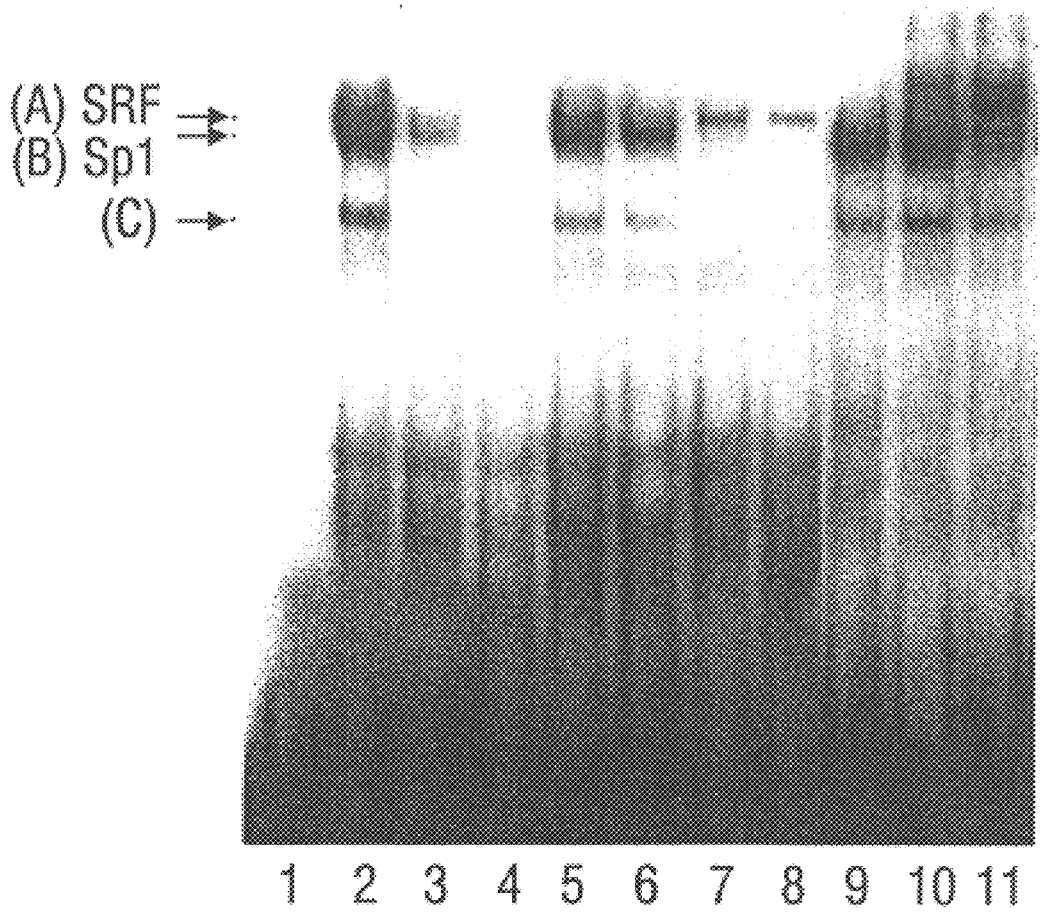
FIG. 4A and FIG. 4B (Scanned images). Electrophoretic mobility shift assays (EMSAs) of the SME-1/CArG and SME-4/CArG nuclear protein binding sites of the arterial SMC-specific SM22α promoter.

To assess the number, specificity, and identity, of nuclear proteins that bind to the arterial SMC-specific SM22α promoter, a series of electrophoretic mobility shift assays (EMSAs) were performed. To determine whether the SME-1/CArG and SME-4/CArG bind common, overlapping, or distinct, sets of trans-acting factors, EMSAs were performed using radiolabeled SME-1 and SME-4 oligonucleotide probes. The radiolabeled SME-1 oligonucleotide probe bound three specific nuclear protein complexes, designated A–C (FIG. 4A, lane 2), as determined by addition of specific and non-specific unlabeled competitor oligonucleotides to the binding reactions (lanes 2–4). Of note, unlabeled SME-4 oligonucleotide competed for binding of complex A, but failed to compete for complexes B and C (FIG. 4A, lanes 5 and 6). Unlabeled Sp1 oligonucleotide competed for binding of complex B (that co-migrated with complex A), as well as, complex C (FIG. 4A, lanes 7 and 8). Antibody supershift studies confirmed that complex A (arrow) contains SRF (or an antigenically related protein) and complex B (arrow) contains Sp1 (or an antigenically related protein) (FIG. 4A, lanes 9–12).

Figure 4B:
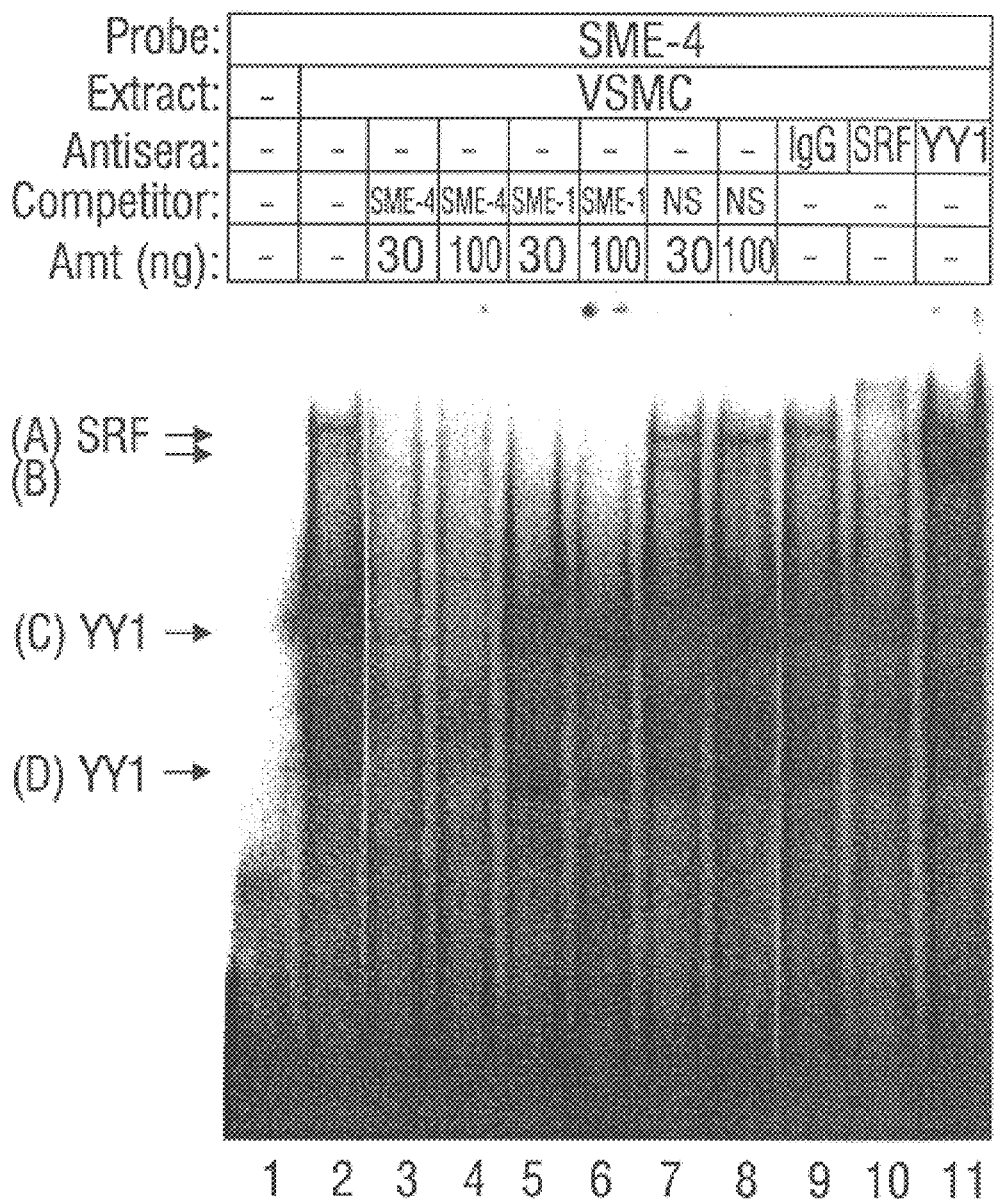

EMSAs performed with the radiolabeled SME-4 oligonucleotide probe demonstrated four specific nuclear protein complexes, designated A–D (FIG. 4B, lane 2), as determined by addition of specific and non-specific competitor oligonucleotides (lanes 3–4 and 7–8). Addition of unlabeled SME-1 oligonucleotide competed only for binding of complexes A and B (FIG. 4B, lanes 5 and 6). Antibody supershift studies revealed that both of these low-mobility nuclear protein complexes contained a protein identical, or antigenically-related, to SRF (FIG. 4B, lane 10, arrow, SRF), while complexes C and D contained a protein identical, or antigenically-related, to YY1 (FIG. 7B, lane 11, arrow, YY1). Taken together, these data demonstrate that, as expected, SRF (or an SRF-containing protein complex) binds to both the SME-1 and SME-4 sites. Of note, the demonstration of two low mobility SME-4 binding activities containing SRF (FIG. 4A, complexes A and B) suggests that one, or both, of these complexes may contain additional trans-acting factors. In addition, SME-1 bound Sp1 (FIG. 4B, complex B) and one potentially novel nuclear protein complex (FIG. 4B, complex C) that does not bind to SME-4. Conversely, SME-4 binds the ubiquitously expressed and potentially negative regulatory factor, YY1 (Gualberto et al., 1992; Lee et al., 1992; Lee et al., 1994) (FIG. 4A, complexes C and D), while SME-1 does not.

Figure 5A:
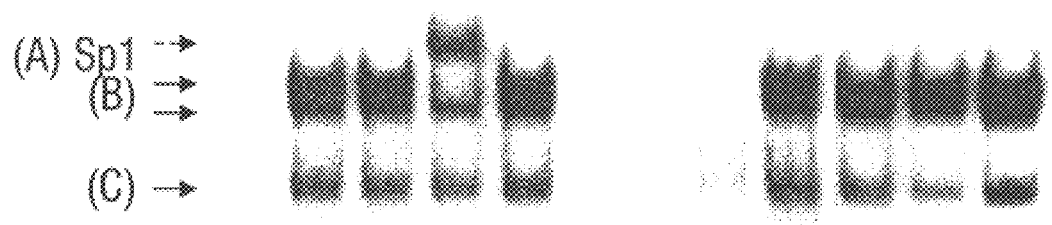
FIG. 5A and FIG. 5B (Scanned images). EMSAs of the SME-5 (FIG. 5A) and SME-3 (FIG. 5B) nuclear protein binding sites of the arterial SMC-specific SM22α promoter.

Both the SME-2 and SME-5 sites are GC-rich motifs that contain potential Sp1 and AP2 motifs (FIG. 3D). EMSAs performed with nuclear extracts prepared from primary rat aortic SMCs and radiolabeled oligonucleotides corresponding to the SME-2 and SME-5 (FIG. 5A) nuclear protein binding sites, respectively, revealed identical band-shift patterns suggesting that these two motifs might bind a common set of trans-acting factors. Each probe bound three specific nuclear protein complexes, designated A–C (FIG. 5A, lane 2), as determined by addition of unlabeled specific and non-specific oligonucleotide competitors (FIG. 5A, lanes 6 and 9). Unlabeled SME-2 oligonucleotide competed for binding of each nuclear protein complex that bound the radiolabeled SME-5 probe and visa versa (FIG. 5A, lane 8). Moreover, an oligonucleotide containing a consensus Sp1 motif competed for binding of complexes A–C (FIG. 5A, lane 7). Antibody supershift studies revealed that complex A (arrow) was ablated and supershifted (dashed arrow) by pre-incubation with Sp1-specific antiserum (FIG. 5A, lane 3), but not by control murine IgG, or α-AP2 antiserum (lanes 3 and 5). Each of these nuclear protein complexes were also present in nuclear extracts prepared from non-SMC lineages including the lymphoid lines, WEHI and 70Z/3 (FIG. 5A, lanes 11 and 12). These data demonstrate that the SME-2 and SME-5 nuclear protein binding sites each bind three ubiquitously expressed nuclear protein complexes, at least one of which contains a protein that is identical, or antigenically related, to Sp1.

Figure 5B:
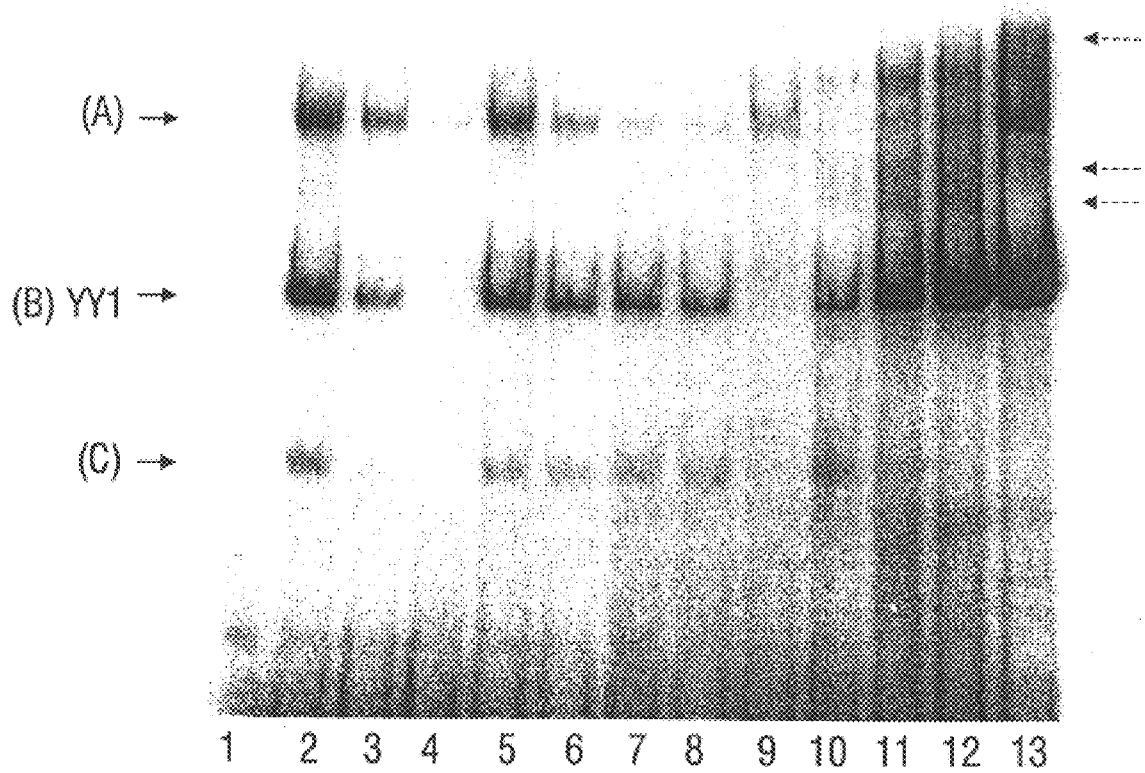

As discussed above, SME-3 was protected from DNase I digestion by nuclear extracts prepared from A7r5 cells, but not by extracts prepared from NIH 3T3 cells, suggesting that this previously undescribed motif might bind one or more SMC lineage-specific trans-acting factors. EMSAs performed with the radiolabeled SME-3 oligonucleotide probe revealed three specific binding activities, designated A–C (FIG. 5B, lane 2), as determined by addition specific and non-specific competitor oligonucleotides (FIG. 5B, lanes 3–6). Antibody supershift studies revealed that complex B and C contained YY1 (or an antigenically related protein) (FIG. 5B, lane 10). None of the nuclear protein complexes were supershifted by control IgG or α-Sp1 antiserum. To determine whether any of these nuclear protein complexes were expressed in a lineage-restricted fashion, EMSAs were performed with the SME-3 probe and nuclear extracts prepared from primary rat aortic SMCs, the SMC line, A7r5, C3H10T½ and NIH 3T3 fibroblasts, and the mouse T cell line, EL4. Interestingly, complex C, which was ablated by pre-incubation with α-YY1 antiserum, was present only in primary rat aortic SMCs and the SMC line A7r5 (FIG. 5B, lane 2 and 7), but was absent in C3H10T½, NIH 3T3, and EL4 nuclear extracts (FIG. 5B, lanes 11–13). Moreover, three faint complexes (dashed arrows) were identified in C3H10T½, NIH 3T3 and EL4 cells, but were not present in SMC extracts (FIG. 5C, lanes 4–7). Taken together, these data suggest that the SME-3 nuclear protein binding site, a motif which has not been described previously, binds YY1 and one or more, as yet, unidentified SMC-specific and/or lineage restricted trans-acting factors. In addition, the radiolabeled SME-3 probe binds three nuclear protein complexes that are present in several non-SMC lines, but not in primary vascular SMCs or the SMC line, A7r5.

Figure 6A:
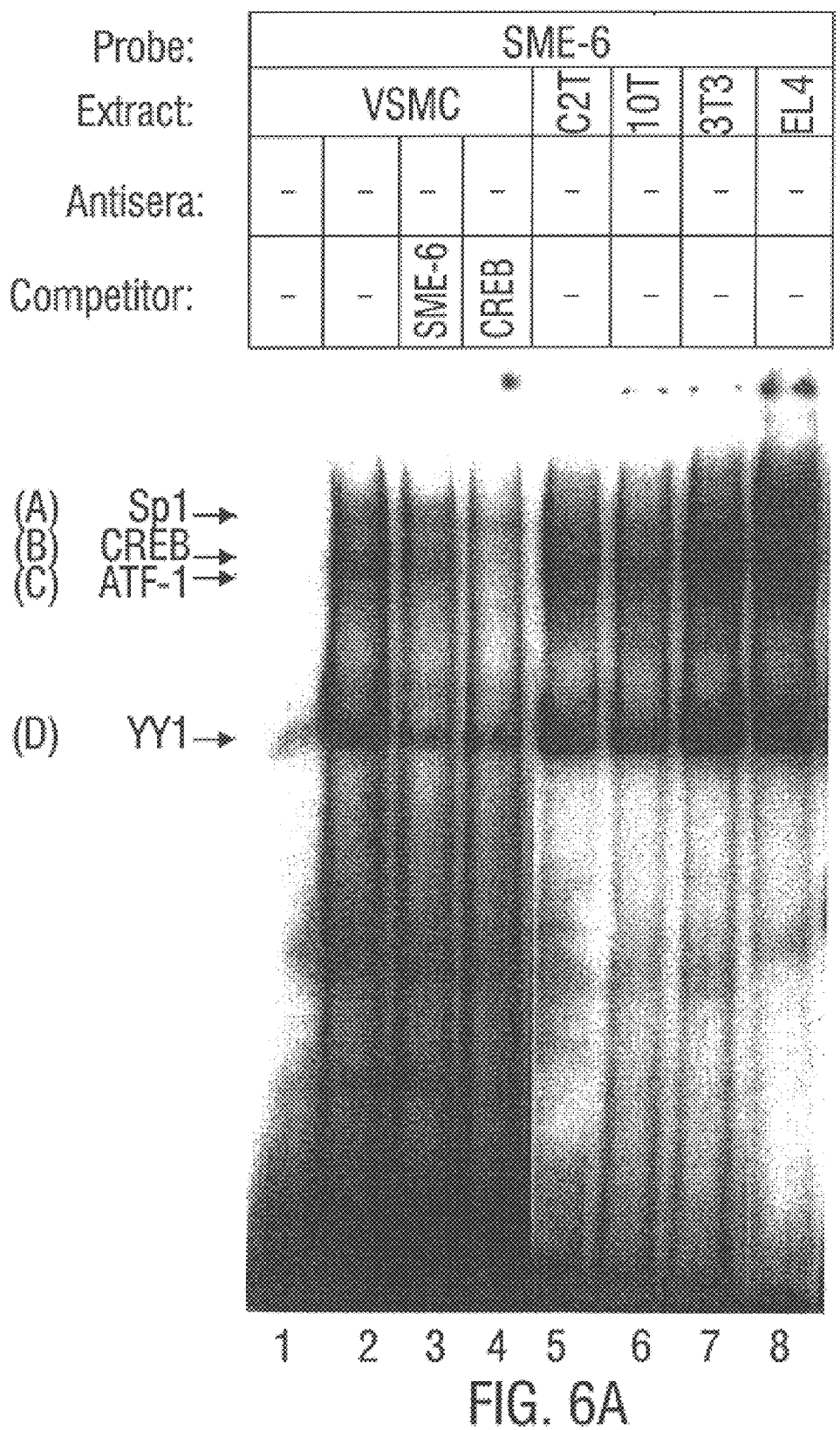
FIG. 6A, FIG. 6B (Scanned images). EMSA of the SME-6/CRE nuclear protein binding site of the arterial SMC-specific SM22α promoter. (A) EMSA performed with the radiolabeled SME-6 oligonucleotide probe and nuclear extracts prepared from primary rat aortic SMCs (VSMC), A7r5 (A7), C2C12 myotubes (C2T), C3H10T½ (10T), NIH 3T3 (3T3) and EL4 cells. Some binding reactions included the indicated unlabeled competitor oligonucleotides or the indicated antiserum. Four specific nuclear protein complexes, designated A–D, are denoted to the left of the autoradiogram. The complexes that were ablated and/or supershifted by α-CREB-1, α-ATF-1, α-Sp1 and α-YY1 antiserum are shown to the left of the autoradiogram.
Figure 6B:
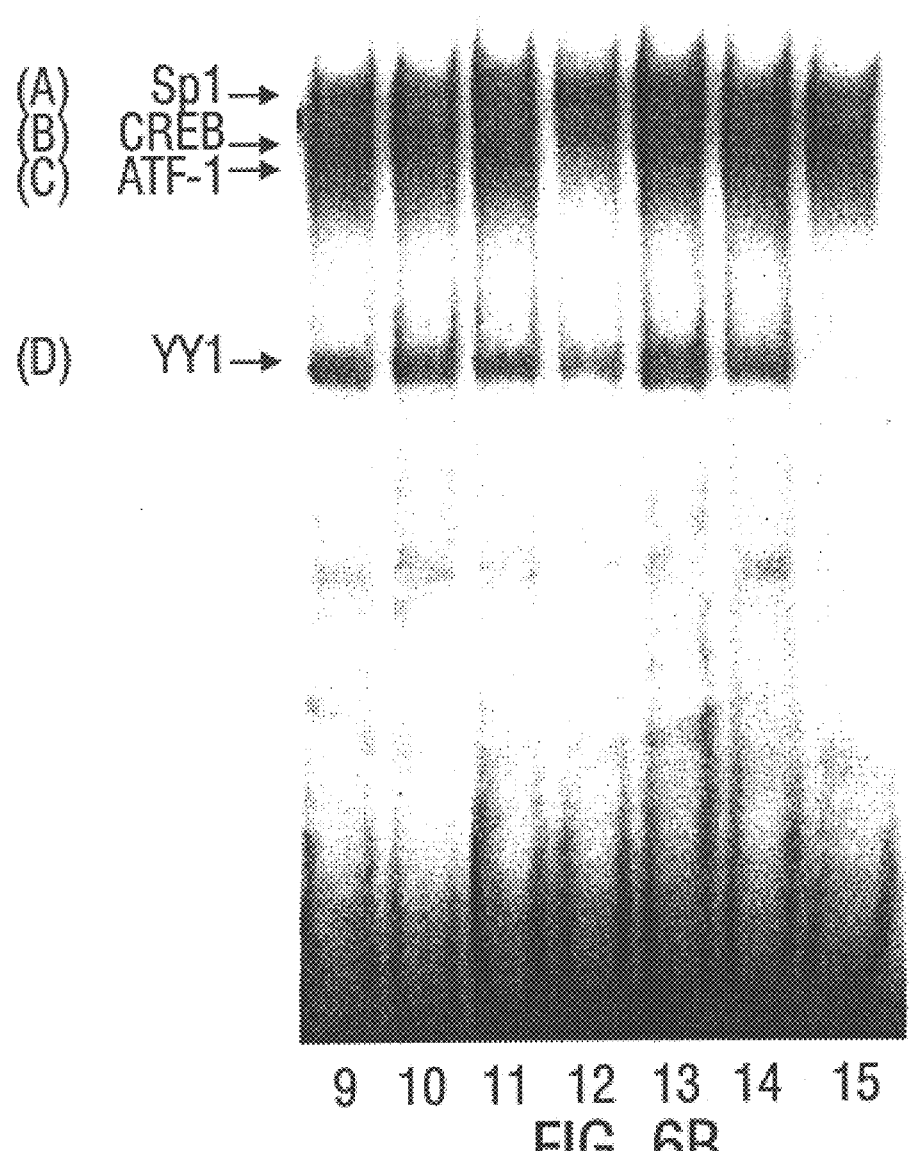

EMSAs performed with a radiolabeled oligonucleotide corresponding to the SME-6 nuclear protein binding site revealed four specific nuclear protein complexes, designated A–D, respectively (FIG. 6, lane 2). Each of these complexes were competed with unlabeled SME-6 oligonucleotide (FIG. 6, lane 3). Moreover, addition of an unlabeled consensus CRE oligonucleotide derived from the T cell receptor α enhancer competed exclusively for binding of complexes B and C (FIG. 6, lane 4). Pre-incubation of the binding reactions with α-CREB-1 antiserum ablated and supershifted complex B (FIG. 6, lane 11, arrow, CREB-1), while complex C was ablated by addition of α-ATF-1 antiserum (FIG. 6, lane 12, arrow, ATF-1). In addition, complex A (FIG. 6, arrow, Sp1) was ablated and supershifted by pre-incubation with α-Sp1 antiserum. Finally, complex D was ablated by the addition of α-YY1 antiserum (FIG. 6, lane 15, arrow, YY1). In contrast, none of the four complexes were ablated or supershifted following pre-incubation with control rabbit or murine IgG (FIG. 6, lanes 9 and 10), or antisera that recognize GATA-4 (FIG. 6, lane 13) or SRF (FIG. 6, lane 14). Interestingly, EMSAs performed with the radiolabeled SME-6 oligonucleotide probe and nuclear extracts prepared from the non-SMC lines, C2C12 myotubes, C3H10T½ and NIH 3T3 fibroblasts, and EL4 T cells, revealed fine differences in the mobilities of several nuclear protein complexes (and/or novel complexes), as well as, increased intensity in each of the SME-6 binding activities (FIG. 6, lanes 5–8). Taken together, these data revealed that the SME-6 motif binds CREB-1 and ATF-1, each of which are expressed in primary vascular SMCs, as well as, the ubiquitously expressed transcription factors, Sp1 and YY1.

Figure 7:
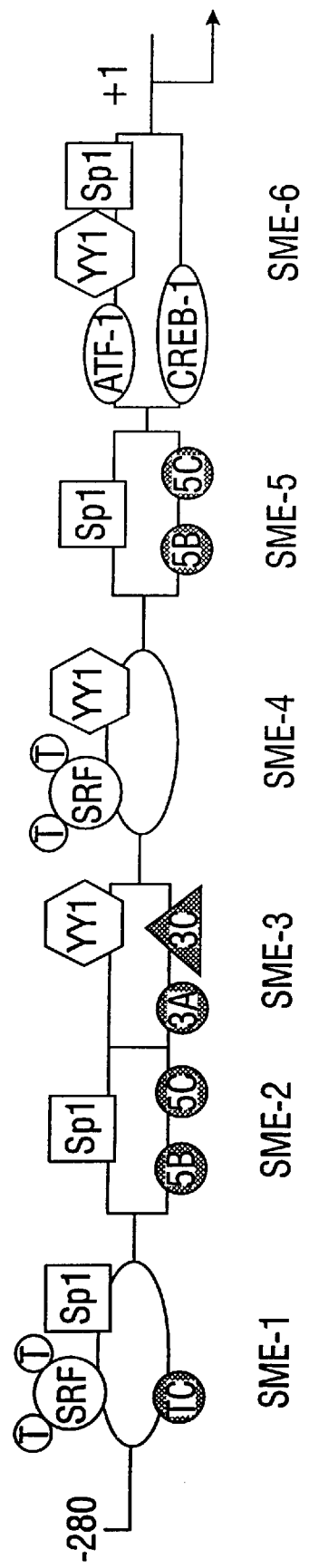
FIG. 7. Schematic representation of the cis-acting elements and the trans-acting factors identified by DNase I footprint and EMSAs analyses that bind to the SM22α promoter. Six nuclear protein binding sites were identified by DNase I footprint analysis in the 441-bp arterial SMC-specific SM22α promoter that were designated SME-1–6, respectively. Trans-acting factors identified by EMSA that bind to each nuclear protein binding site are shown above or below each cis-acting element. Binding sites for SRF and ternary complex factors (T) (SME-1 and SME-4), Sp1 (SME-1, -2, -5, -6), YY1 (SME-3, -4, -6), CREB-1 (SME-6) and ATF-1 (SME-6) were identified. Of note, nuclear protein complexes that could not be positively identified by antibody supershift reactions are shown in gray below the nuclear protein binding site to which they bind.

In summary, as shown in FIG. 7, the arterial SMC-specific SM22α promoter contains six nuclear protein binding sites, designated smooth muscle element (SME)1–6, respectively. SME-1/CArG binds SRF (and ternary complex factors), Sp1 and one unidentified nuclear protein complex that is not cross-competed by SME-4/CArG oligonucleotides. SME-2 binds three specific nuclear protein complexes at least one of which contains Sp1, each of which also binds to the SME-5 site. SME-3, a motif that has not been described previously, binds YY1 and two unidentified nuclear protein complexes, one of which includes a potentially novel lineage-restricted trans-acting factor. In addition, the SME-3 motif binds several trans-acting factors which are present in nuclear extracts prepared from non-SMCs but which are not present in SMC extracts. SME-4/CArG binds nuclear protein complexes containing SRF and YY1-related proteins. Of note, two high mobility complexes were ablated and supershifted by pre-incubation with a-SRF antiserum suggesting that one, or both, of these nuclear protein complexes may contain accessory factors. Finally, SME-6 binds CREB-1, ATF-1, YY1, and Sp1.

EXAMPLE 10

Functional Characterization of the SM22α Promoter

Figure 8A:
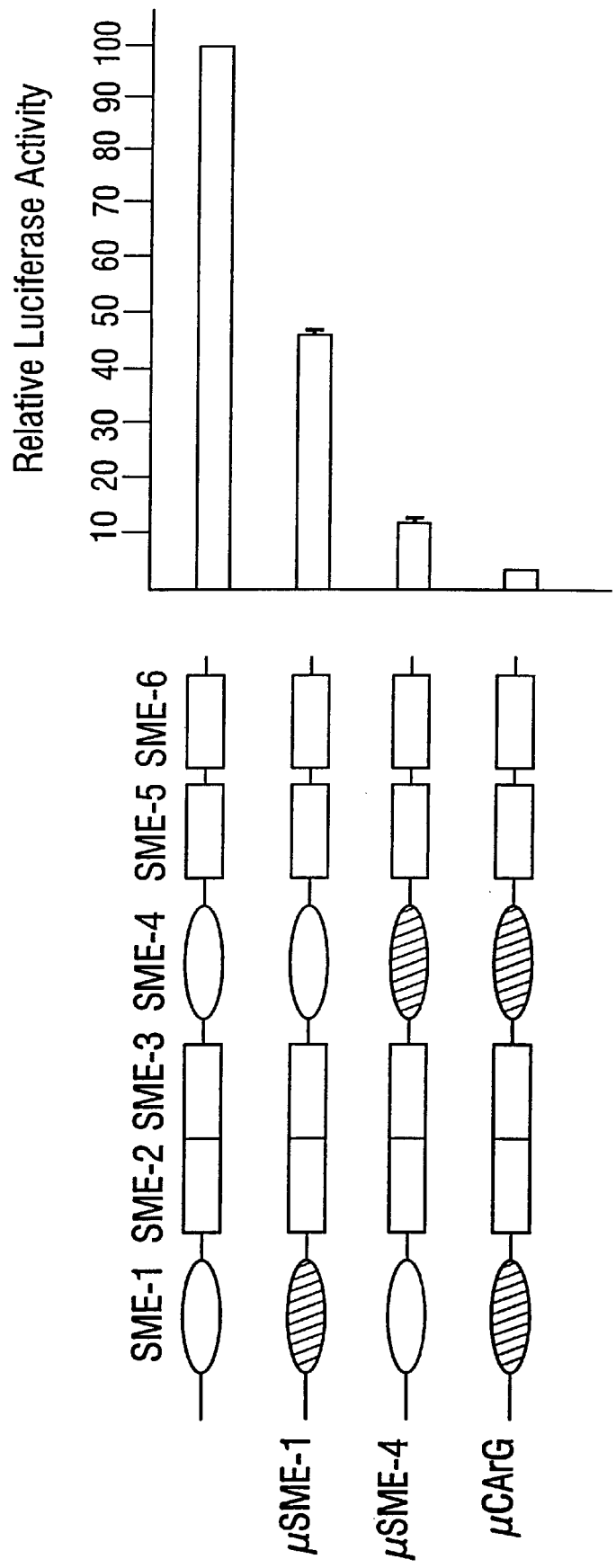
FIG. 8A and FIG. 8B. Functional analysis of the cis-acting elements that control transcription of the SM22α promoter in arterial SMCs. Mutations were introduced into the 441-bp SM22α promoter as described below. The mutant promoters were subcloned into the pGL2-Basic luciferase reporter plasmid, and the resulting plasmids were transfected into primary rat aortic SMCs. A schematic representation of the SM22α promoter and the mutated cis-acting elements (indicated by black) are shown to the left of the graph. Luciferase activities, corrected for differences in transfection efficiencies, are shown as a percent of the luciferase activity observed with the p-441SM22luc plasmid ±S.E.M. Each transfection was repeated at least three times.

To characterize the functional significance of each of the cis-acting elements within the SM22α promoter, specific mutations that abolish binding of one or more trans-acting factors to nuclear protein binding sites located within the SM22α promoter were created within the context of the p-441SM22luc reporter plasmid. The effect of each mutation was assessed by transient transfection analysis of each mutant SM22α promoter luciferase reporter plasmid into primary rat aortic SMCs. To assess the function of the SME-1/CArG and SME-4/CArG sites, each of which bind SRF, mutations were created that abolish SRF binding to SME-1, and SRF and YY1 binding to SME-4, respectively. Of note, these mutations did not affect binding of any other nuclear protein complex (demonstrated by EMSA) to SME-1 or SME-4. Transfection analyses revealed that mutation of the SME-1 site resulted in a 55% reduction in normalized luciferase activity compared to that obtained with the p-441SM22luc plasmid (FIG. 8A, lane 2). Remarkably, a two nucleotide substitution in the SME-4 site that abolished SRF binding activity resulted in a 88% reduction in normalized luciferase activity compared to that obtained with the wild type SM22α promoter (FIG. 8A, lane 3). Moreover, the p-441SM22μCArG plasmid, which contains mutations in both SME-1 and -4 that inhibit binding of SRF, completely abolished transcriptional activity of the SM22α promoter in primary rat aortic SMCs and the SMC-line A7r5 (FIG. 8A, lane 4). These data demonstrate that the SME-1 and -4 nuclear protein binding sites are required for activity of the SM22α promoter in arterial SMCs in vitro. Moreover, these data suggest that SM22α promoter activity is critically-dependent upon the SME-4 site, SRF, and/or trans-acting factors that interact with SRF.

Figure 8B:
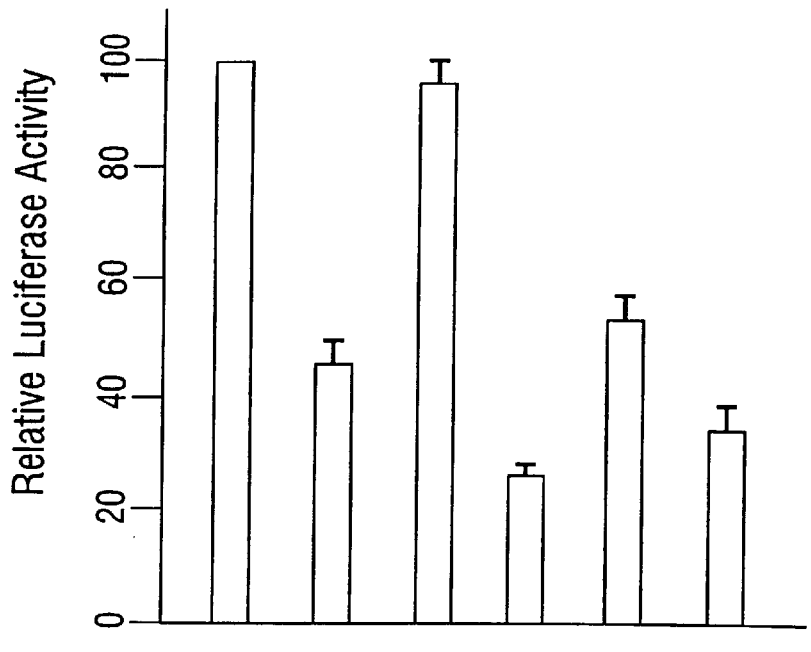
Figure 8B:
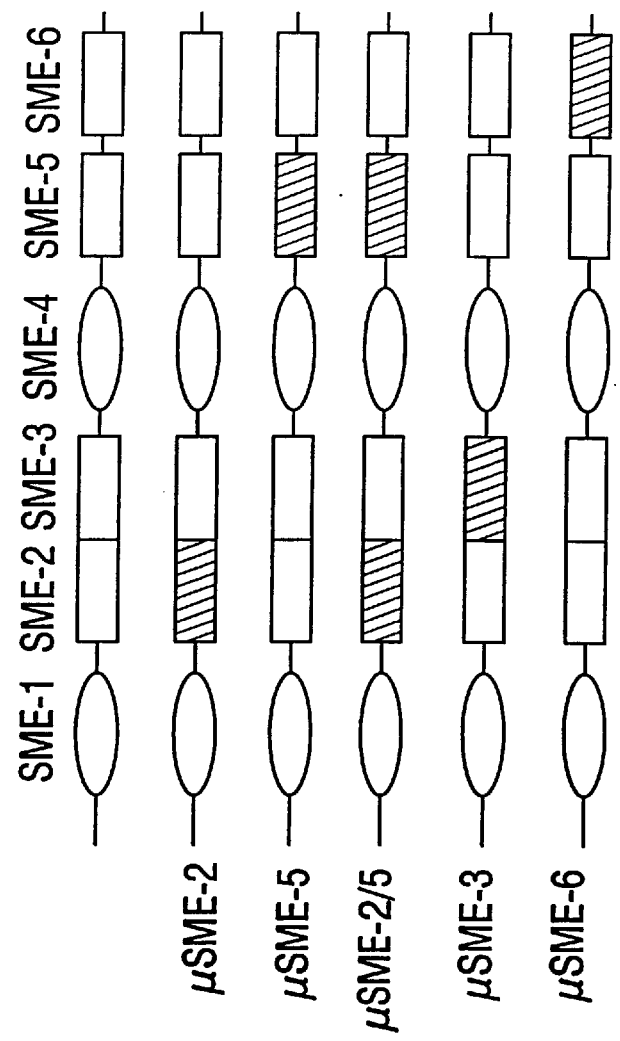
Figure 9:
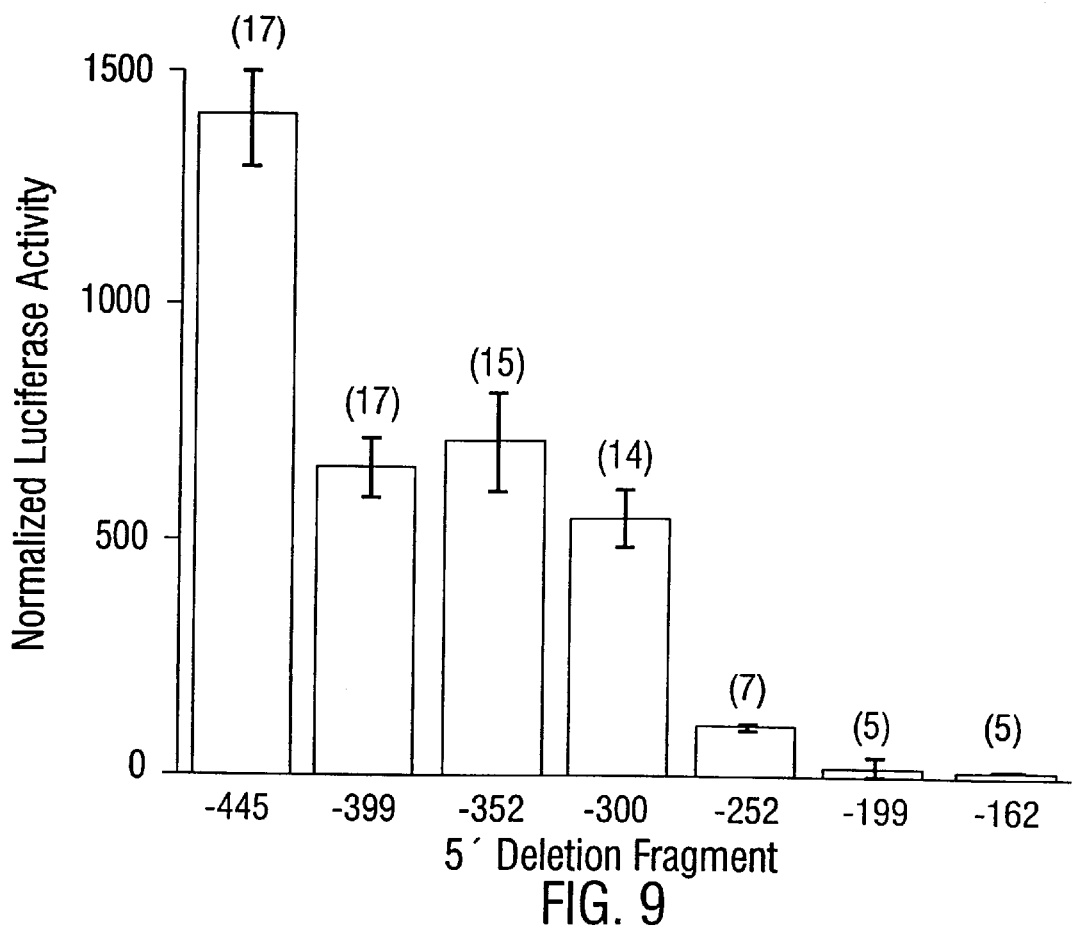
FIG. 9. Analysis of 5' deletions from the SM22α promoter as measured by normalized luciferase activity. Deletion of bp −445 through −400 (column −399) reduces luciferase activity by approximately 50% compared to the complete SM22α promoter (column −445). Further deletions of bp −445 through −301 (columns −352 and −300) does not further reduce luciferase activity. Deletion of bp −445 through −163 (columns −252, −199 and −162) nearly eliminated all measurable SM22α activity.
Figure 10:
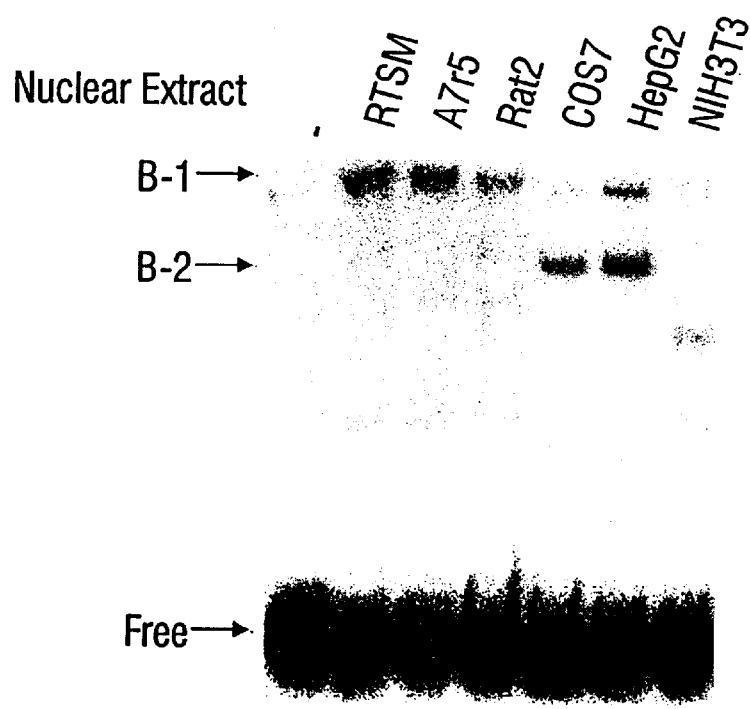
FIG. 10 (Scanned image). EMSA analysis of DNA region encompassing a cis-acting, positive transcriptional regulatory element. A radiolabeled double-stranded oligonucleotide corresponding to bp −445 to −389 specifically binds nuclear proteins extracted from either A7r5 SMCs or cultured rat tracheal SMCs (band B-1).
Figure 12:
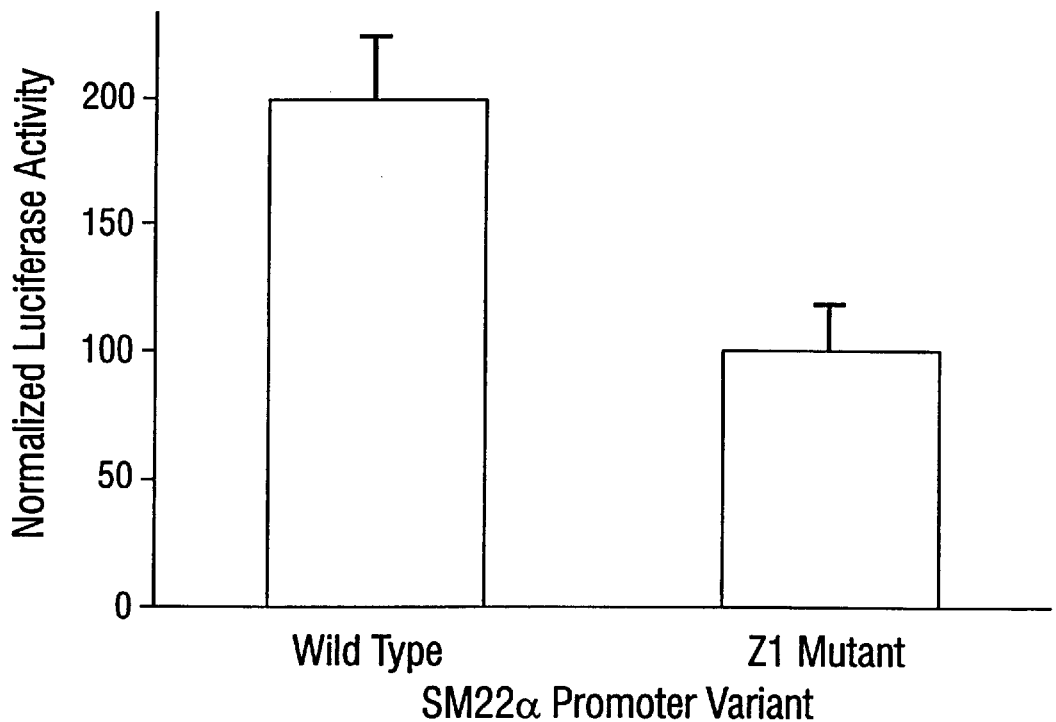
FIG. 12. Transient transfection assays demonstrate that mutation of the Z1 zeste-binding site of the 441-bp SM22α promoter reduces transcriptional activity to approximately one-half of the wild type 441-bp SM22α promoter in A7r5 SMCs (as assessed by normalized luciferase activity), confirming the importance of the Z1 site as an important positive transcriptional regulatory sequence within the SM22α promoter.
Figure 13:
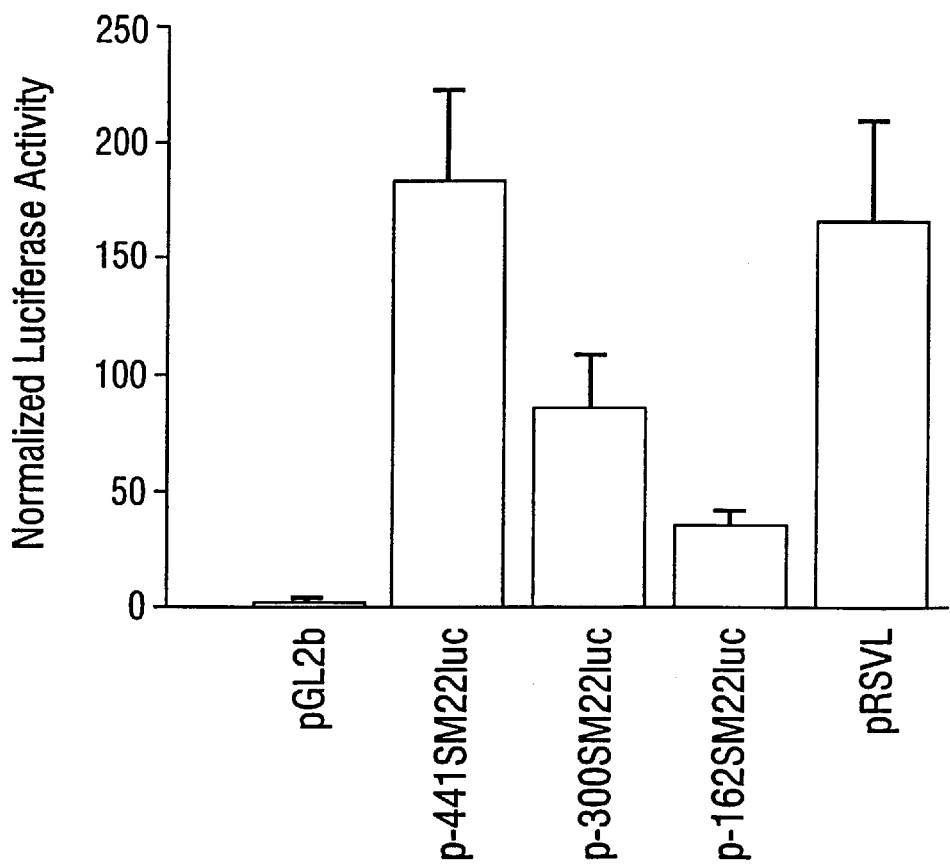
FIG. 13. Normalized luciferase activity of recombinant vectors containing the 482-bp (p-441SM22luc), the 341-bp (p-300SM22luc) or the 201-bp (p-162SM22luc) SM22α promoter and transfected into cultured rat tracheal SMCs compared to the luciferase activity of the highly active LTR promoter, of the RSV virus, present in the recombinant vector pRSVL. Activity of the 482-bp SM22α promoter is equivalent to the activity of the LTR promoter.
Figure 14:
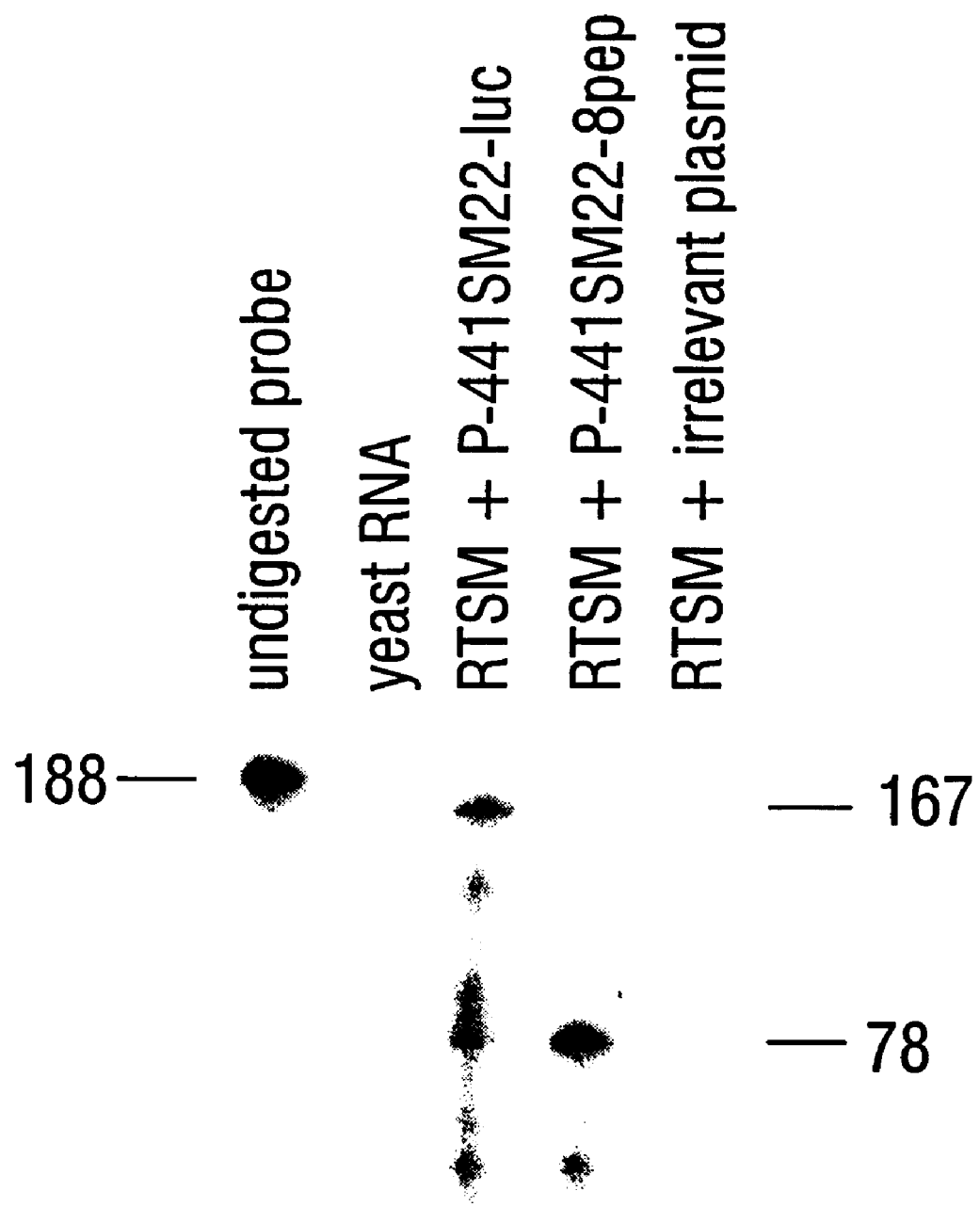
FIG. 14 (Scanned image). Ribonuclease protection assay (RPA) detects the presence of protected fragments of 167 and 78 nucleotides in RNA from cultured rat tracheal SMCs transfected with p-441SM22luc and p-441SM22-8pep, respectively, indicating that luciferase-encoding mRNA and MIRICRKK, SEQ ID NO:19,-encoding mRNA is present and the promoter is active.

To assess the functional significance of each of the other (non-CArG containing) nuclear protein binding sites in the SM22α promoter, mutations that abolish binding of one or more trans-acting factor to each site were created within the context of the 441-bp SM22α promoter containing plasmid, p-441SM22luc. Because the SME-2 and SME-5 nuclear protein binding sites, each bind a nuclear protein complex containing Sp1, in addition to two other common nuclear protein complexes (FIG. 5A, lanes 5 and 7), mutations were created within the context of the p-441 SM22-luc plasmid that abolish binding of each trans-acting factor to SME-2, SME-5, and both SME-2 and SME-5. Transfection of each of these plasmids and the p-441 SM22-luc plasmid into primary rat aortic SMCs demonstrated that mutation of the SME-2, SME-5, and SME-2 and SME-5, resulted in 58%, 6% and 70% respective reductions in normalized luciferase activities (FIG. 8B lanes 2–5). These data suggest that within the context of the SM22α promoter, the SME-2, and -5 nuclear protein binding sites are required for full promoter activity, but may be functionally redundant.

Mutation in the SME-3 site which abolishes binding of all three SME-3 binding activities (including the potentially novel lineage-restricted trans-acting factor) resulted in a 50% reduction in transcriptional activity compared to that observed with the native SM22α promoter (FIG. 8B, lane 5). These data suggest either that activity of the SM22α promoter in arterial SMCs is not critically dependent on this potentially novel lineage-restricted trans-acting factor, or alternatively, that an additional nuclear protein binding site for this lineage-restricted trans-acting factor exists in the 441-bp SM22α promoter (that was not detected by DNase I footprint analyses and EMSAs). To assess the functional significance of the SME-6 nuclear protein binding site, and to determine whether the CRE located within SME-6 is required for promoter activity, the −441SM22μCREB/SME-6 plasmid, which abolishes binding specifically of each of the CRE-related complexes (but not YY1) was compared to the p-441SM22luc reporter plasmid. The single mutation within the CREB motif reduced transcriptional activity by approximately 60% (FIG. 8B, lane 6). In contrast, mutations within SME-6 that do not abolish CRE binding activities did not significantly decrease transcriptional activities. These data suggest that CREB family members may play an important functional role in transcription of the SM22α gene in VSMCs.

The Arterial SMC-specific SM22α promoter is CArG-dependent In vivo

As shown above, mutations of the SME-1/CArG and SME-4/CArG elements that inhibited binding of SRF to the SM22α promoter, totally abolished SM22α promoter activity in arterial SMCs in vitro. To determine whether SME-1 and -4 are required for activity of the SM22α promoter in arterial SMCs (and the myotomal component of the somites) in vivo, transgenic mice were produced containing a transgene, designated −441SM22μCArG, that encodes the bacterial lacZ reporter gene under the transcriptional control of a mutant SM22α promoter containing mutations in both SME-1 and SME-4 that abolish binding of SRF (as described above). Thirteen independent −441SM22μCArG transgenic lines were produced with copy numbers ranging between 1 and 730 copies per cell. In contrast to the −441SM22lacZ transgenic mice that expressed the lacZ transgene in the arterial SMCs and within the myotomal component of the somites (FIG. 1A), in 12 out of 13 independent −441SM22μCArG lines, β-galactosidase activity could not be detected in either the arterial SMCs or within the myotomal component of the somites at ED11.5. Of note, in one line harboring the −441SM22μCArG transgene (that contained 5 copies per cell), blue staining was detected exclusively within the cardiac outflow tract, but not within the SMCs of the dorsal aorta or branch arteries, the somites, or any other tissue. Given the low frequency at which this pattern of lacZ expression was observed, it is likely that it resulted from integration of the transgene near a cryptic enhancer element. These data demonstrate that the SME-1 and SME-4 nuclear protein binding sites located within arterial SMC-specific SM22α promoter are required for SM22α promoter activity in vivo. Moreover, these data suggest strongly that SRF plays an important role in regulating activity of the SM22α promoter in vivo.

EXAMPLE 11

Spatial and Temporal Patterns of Activation of the Arterial SMC-Specific SM22α Promoter During Embryonic Development The SM22α gene is expressed in the developing vasculature at least as early as (and probably earlier tan) embryonic day (ED) 9.5 in the mouse, demonstrating that it is one of the earliest developmental markers of the SMC lineage.

As transcriptional activation precedes mRNA and protein expression, the study of SM22α provide an opportunity to examine SMC-specific transcription at its earliest stages after (and potentially during) migration of mesodermal stem cells from the lateral plate mesoderm and neural crest to locations throughout the embryo. Utilizing the −441SM22lacZ lines of transgenic mice, described earlier, that contain the 441-bp SM22α promoter linked to the bacterial lacZ reporter gene, the spatial and temporal pattern of SM22α transcriptional activation during early embryogenesis, ED6, ED7.5, ED8.5, ED9.5, ED10.5, and ED11.5 is determined as confirmed by PCR™, and embryonic sections are fixed in 37% formaldehyde, 25% glutaraldehyde in PBS and stained with X-gal as previously described (Lin et al., 1990). The cells in which the SM22α promoter is transcriptionally active are stained blue. In these studies, the non-transgenic litter mates of the transgenic mice serve as negative controls, and these embryos are assayed for β-galactosidase activity as described above. Sections are analyzed to determine the spatial location and cell type in which SM22α transcriptional activation is initially detectable (particular emphasis is placed on examining the lateral plate mesoderm and neural crest in ED6, ED7.5 and ED8.5 embryos). As both cardiac myocytes and some SMCs are derived from the lateral plate mesoderm, to distinguish cardiac myocytes from SMCs, the pattern of staining in whole mount −441SM22lacZ transgenic ED6-ED9.5 embryos is compared to a staged series of embryos that were hybridized previously to the early cardiac lineage-restricted transcription factor GATA-4 cRNA probe which is first detectable in the promyocardial tissues of ED7.5 embryos (Ip et al., 1994). Taken together, this series of studies explore the earliest stages of SMC development, and follow SMCs as they arise from lateral plate mesoderm (which gives rise to the dorsal aorta and branch arteries) and neural crest precursors (which give rise to the cardiac outflow tract). Moreover, because the 441-bp SM22α promoter is active exclusively within arterial, but not visceral, SMCs these studies determine at what embryonic stage tissue-restricted subsets of SMCs can be distinguished.

Functional Assessment of cis-acting Sequences by Transient Transfection Analyses In order to determine the functional significance of each cis-acting element within the SM22α promoter, each nuclear protein binding site identified by DNase I footprint analyses and characterized by EMSAs is mutated within the context of the native 441-bp SM22α promoter and the transcriptional activity of each mutated promoter plasmid tested by transient transfection analyses in primary rat aortic SMCs and A7r5 cells. In addition, to determine whether common, overlapping, or distinct cis-acting elements control activity of the SM22α promoter in arterial SMCs and embryonic skeletal muscle cells, C2C12 myotubes (which express SM22α mRNA (Solway et al., 1995)) are also transfected as described previously (Parmacek et al., 1994). Prior to mutagenesis, mutations in each nuclear protein binding site are analyzed by EMSAs to confirm that the mutation abolishes nuclear protein complex binding. Mutations are created within the context of the p-441SM22luc plasmid by gapped heteroduplex oligonucleotide-mediated or PCR™-mediated site directed mutagenesis as described previously (Parmacek et al., 1994). To assess the activity of potentially redundant elements (for example SME-1 and SME-4 each bind SRF), double mutants are generated. Transient transfections of primary rat aortic SMCs and the SMC line, A7r5, are then performed and the luciferase activity of each mutated promoter plasmid compared to that obtained following transfection with the native SM22α promoter-containing luciferase reporter plasmid, p-441SM22-luc (see FIG. 4A and FIG. 4B). The promoterless pGL2-Basic plasmid serves as a negative control and the pGL2-Control plasmid containing the SV40 promoter and transcriptional enhancer serves as a positive control. To assess transcriptional rates the results of representative luciferase assays are confirmed by performing RNase protection assays (Solway et al., 1995) on RNA isolated from duplicate representative transfections using probes complimentary to the 5' end of the firefly luciferase gene and the SM22α core promoter. In addition, transfection efficiencies are monitored by co-transfection with the pMSVβgal reference plasmid as described previously (Parmacek et al., 1992). Finally, after each of the nuclear protein binding sites located within the SM22α promoter have been characterized as described above, synthetic oligonucleotides corresponding to each of the functionally important nuclear protein binding sites are oligomerized in various copy numbers and combinations and inserted 5' of the minimal TATA containing SM22α promoter luciferase plasmid, designated p-40SM22luc, in order to determine whether the presence of randomly spaced, or oligomerized, nuclear protein binding sites, alone or in various combinations, is sufficient for SM22α promoter activity in arterial SMCs. These studies define a "modular promoter" that could be utilized to target gene expression to arterial SMCs.

Analyses of SM22α Promoter Mutants in Transgenic Mice

To confirm the functional importance of cis-acting sequences within the SM22α promoter in vivo, the activity of informative SM22α promoter mutants are assessed in transgenic mice. Because it is desirable to detect both qualitative (with respect to the tissue-restricted pattern of transgene expression), as well as quantitative differences in SM22α promoter activity, the bacterial lacZ gene has been utilized in each transgenic construct. Of note, until recently quantitative analysis of transgene expression has required the use of reporter genes such as firefly luciferase or bacterial chloramphenicol acetyltransferase because of the need for an ultra-sensitive assay that is linear over several orders of magnitude. However, an ultra-sensitive chemilluminescent β-galactosidase assay (Tropix) has been developed that has been used to quantitate β-galactosidase activity in tissues of transgenic mice. Transgenic constructs will be cloned by isolatgin the mutated SM22α promoter subfragments from the pGL2-Basic luciferase reporter plasmid by digestion with XhoI and HindIII and subcloning the promoter sequences into the pBS-lacZ transgenic plasmid (a pBluescript-based phagemid containing the lacZ gene inserted in the polylinker). Construction of each plasmid is confirmed by both restriction endonuclease mapping and DNA sequence analysis as described previously (Paquet et al., 1990; Parmacek et al., 1990; Parmacek et al., 1994; Parmacek and Leiden, 1989; Parmacek et al., 1992). Transgenic mice are produced as described previously (Metzger et al., 1993). Founder mice are identified by Southern blot analyses as described earlier. Each respective construct is represented by at least four founder mice. Of note, because transgene expression is affected by both the site of integration into the host genome and in some cases by copy number (no relationship between the copy number and β-galactosidase expression has been detected in the four −441SM22-lacZ lines of transgenic mice analyzed to date), transgenic offspring from at least four independent founders with each construct are analyzed.

F0 ED 11.5 transgenic mouse embryos are fixed and histochemically stained for β-galactosidase activity as described earlier. Whole embryos are stained through ED15.0 (the last day the fixative and stain will penetrate) and sections of adult mice are stained as described previously (Lin et al., 1990). These analyses determine the function of each cis-acting element (SME-1–6) in regulating the spatial and temporal pattern of SM22α gene expression in the developing mouse. To determine the quantitative effects of each mutation on SM22α promoter function, the normalized β-galactosidase activity of aortic homogenates prepared from 6 wk old transgenic mice in which the lacZ gene is under the transcriptional control of specific SM22α promoter mutants are compared to the β-galactosidase activity in aortic homogenates prepared from the 441SM22-lacZ lines of transgenic mice (positive control). Quantitative β-galactosidase assays are performed according to the manufacturer's directions (Tropix, Inc.) using an LKB/Wallace Bio-orbit Luminometer. β-galactosidase activity is normalized to protein content and expressed as percent of β-galactosidase activity obtained with the wild-type promoter as described previously (Parmacek et al., 1992). In each study, homogenates from non-transgenic litter mates serve as negative controls. These studies, coupled with earlier results described above, define the function of each of the six cis-acting elements within the 441-bp SM22α promoter both in vitro and in vivo. In addition, these studies address the question of whether distinct, common or overlapping cis-acting elements control transcription of the SM22α gene in arterial SMCs and the somites during murine embryogenesis. These studies also serve to identify negative cis-acting regulatory elements that restrict activity of the SM22α promoter to arterial SMCs and the somites by identification of transgenic mice in which β-galactosidase activity is expressed in non-muscle cell lineages.

EXAMPLE 12

Molecular and Biochemical Analyses of Trans-Acting Factors that Regulate SM22α Gene Expression These studies identify SMC lineage-specific or lineage-restricted transcription factors that bind to functionally important nuclear protein binding sites of the SM22α promoter. Electrophoretic mobility shift assays (EMSAs) are performed to determine the number and cell-specificity of trans-acting factors that bind to each functionally important nuclear protein binding site in the SM22α promoter. In addition, to aid in the functional characterization of each trans-acting factor, the precise contact residues of each nuclear protein complex and its cognate binding site are identified by methylation and uracil interference analyses. Finally, to facilitate the cloning and structural characterization of novel SMC-specific transcription factors, the number, lineage-specificity, and size of the proteins that compose each potentially novel nuclear protein complex are characterized by UV-crosslinking analysis. Of note, nuclear protein complexes that are identified by EMSAs often represent multi-protein complexes due to the non-denaturing electrophoresis conditions utilized. Therefore a nuclear protein complex that appears to be expressed in a ubiquitous fashion may in fact include lineage-restricted transcription factors.

Electrophoretic Gel Mobility Shift Assays (EMSAs)

The lineage specificity of the nuclear protein complexes that bind to SME-1–6 are analyzed by EMSAs as described (Ip et al., 1994; Parmacek et al., 1994; Parmacek et al., 1992). For these studies, nuclear extracts have been prepared from primary rat aortic SMCs, the rat SMC line, A7r5, murine C2C12 and So18 skeletal myoblasts and myotubes, primary rat cardiac myocytes (90–100% myocytic/10% fibroblasts), mouse NIH 3T3 and C3H10T½ cells and human umbilical vein endothelial cells. In addition, double-stranded oligonucleotide probes corresponding to each of the nuclear protein binding sites within the SM22α promoter (see FIG. 3D) have been synthesized and annealed. EMSAs are performed as described previously using both high and low ionic strength binding buffers (Ip et al., 1994; Parmacek et al., 1994; Parmacek et al., 1992). The specificity of band shifts (protein-bound DNA) will be determined by performing cold-competition studies using either unlabeled specific or non-specific mutated oligonucleotide competitors in the reaction mixture. A band shift that represents a specific DNA-protein interaction is competed only by specific unlabeled oligonucleotides. To identify SMC lineage-specific nuclear protein complexes, the binding patterns obtained with SMC (primary rat aortic SMCs and the SMC line A7r5) and non-SMC extracts are compared. Of note, it is also possible that the SMC lineage-specific pattern of SM22α transcription is controlled in whole, or part, by a transcription factor that is expressed exclusively in non-SMCs which binds to the SM22α promoter and suppresses transcription. Therefore, attention is also focused on determining whether a nuclear protein complex is expressed in non-SMC lineages. Finally, to determine whether any of the proteins that bind to previously described consensus motifs located within the SM22α promoter (ie., SME-2 contains a potential Sp1 binding site and SME-6 contains a potential CREB/ATF binding site) are antigenically-related, or identical, to known transcription factors, antibody supershift reactions are performed as described previously (Johansen and Prywes, 1993). In these studies, pre-immune serum are added to the reaction mixtures that do not contain specific antiserum to control for artifactual differences in band migration due to the addition of serum. The mobility of a nuclear protein complex that contains a protein which is recognized by the specific antibody will migrate more slowly (be "supershifted") than the DNA-protein complex alone. Alternatively, in some cases the binding of a nuclear protein complex which is recognized by the antisera is abolished.

Methylation and Uracil Interference Analyses

To perform methylation interference analyses, 12.5 pM of oligonucleotide corresponding either to the sense or anti-sense strands of each of the respective SM22α nuclear protein binding site is phosphorylated with $^{32}$P-γATP and T4 polynucleotide kinase, annealed together and free counts removed as described previously (Parmacek and Leiden, 1989). 5 ml (5×10$^6$ DPM) of oligonucleotide is then methylated in 0.05M DMS (which methylates guanine residues at the N-7 position and adenines at the N-3 position). The methylated probe is purified by sequential precipitations and EMSAs scaled up 5–10-fold are performed using the radiolabeled, methylated probes and SMC nuclear extracts. The wet gel is autoradiographically exposed overnight and bands corresponding to the complexes previously identified by EMSAs, as well as the unbound probe (at the bottom of the gel), are excised and the DNAs electroeluted. The resuspended DNA pellets are then cleaved with piperidine, lyophilized, and the protein-bound DNA, as well as the unbound free probe are electrophoretically separated on a 6% DNA sequencing gel. Guanosine (G) residues visible with the free probe and absent in the protein bound probe represent DNA-protein contact residues. Adenines can also be detected in this assay but these reactions are much weaker than the G reactions. In all cases, binding to both sense and antisense strands is examined.

In a complementary series of studies, uracil interference analyses are performed. To prepare $^{32}$P-labeled deoxyuracil-substituted probes (corresponding to each SM22α nuclear protein binding site), 8–12 cycles of PCR™ are performed using 0.2 pmol of template DNA, 20 pmol of one (either sense or antisense) [$^{32}$P]-end-labeled PCR™ primer, 20 pmol of the complementary unlabeled primer (primers are identical to the nucleotide sequences flanking each nuclear protein binding site), 5 μl of 2 mM dNTP mixture, 5 μl of 0.5 mM dUTP, 5 μl of 10×Taq buffer and 1 μl of Taq polymerase as described previously (Parmacek and Leiden, 1989). The two PCR™ reactions which differ with respect to radiolabeled oligonucleotide primer yield binding site probes that are specific for the individual strands. The PCR™ products are then purified as described above and the primer pairs annealed. Scaled-up EMSAs are then performed, the informative bands (and free probe) isolated, and DNA electroeluted from the wet gel slices as described above. The DNAs are then cleaved at the uracil residues by digestion with uracil-N-glycosylase for 1 h at 37° C. The resuspended DNA pellets are then cleaved with piperidine, lyophilized, and electrophoretically separated on a 6% DNA sequencing gel. Thymine residues visible with the free probe and absent in the protein bound probe represent DNA-protein contact. By sequentially identifying the precise contact residues of each respective nuclear protein complex identified by EMSAs by both methylation and uracil interference analyses, a targeted functional assessment of each nuclear protein complex that binds to each nuclear protein binding sites within the SM22α promoter can be undertaken. In addition, DNA-protein binding conditions may be optimized to selectively isolate and characterize a specific nuclear protein complex by UV crosslinking and/or oligonucleotide affinity chromatography.

UV-crosslinking Analysis

Functionally important trans-acting factors that bind to the SM22α promoter are biochemically characterized by UV-crosslinking to radiolabeled oligonucleotides as described by Chodosh et al. (1986). In these studies, a synthetic oligonucleotide (approximately a 40–50 mer) containing a SM22α promoter nuclear protein binding site (as deduced by the analyses described above) are annealed to a complementary 15-bp synthetic oligonucleotide derived from the 3' end of this 40–50 bp oligonucleotide. The hybridized complex are radiolabeled using the Klenow fragment of DNA polymerase I in the presence of BrdU and [α$^{32}$P]-dCTP. The labeled double-stranded oligonucleotide is purified by PAGE and used in a scaled-up EMSAs containing 105 counts of labeled probe and 20 μg of nuclear extract prepared from primary rat aortic SMCs (and non-SMCs) in the presence of 10 μg of poly-dI:dC. After 15 minutes at room temperature, the binding reactions is irradiated for periods between 5 and 30 minutes at 305 nm with an intensity of 7,000 microwatts/cm$^2$. Following irradiation, the reaction mixture will be treated with DNase I and micrococcal nuclease to digest unbound probe. The reaction mixture is then fractionated by SDS-PAGE and the size, number and lineage-specificity of binding proteins determined. Particular emphasis is placed on characterizing SMC-specific nuclear proteins by comparing the DNA binding proteins present in nuclear extracts prepared from SMCs to nuclear proteins present in striated muscle and non-muscle cells. SMC lineage-specific trans-acting factors identified in these studies, are isolated by either the λgt11 screening technique described by Singh et al. (1988) or by oligonucleotide-affinity chromatography as described by Tijan (Kodonaga and Tijan, 1986).

EXAMPLE 13

Functional Characterization of Transcription Factors that Regulate the SM22α Promoter in Arterial SMCs The purpose of these studies is to define the positive or negative regulatory function of each trans-acting factor on SM22α promoter activity in SMCs and to examine how combinatorial interactions between these factors regulate SM22α gene expression. To define the function of a specific trans-acting factor on SM22α promoter function, both loss of function and gain of function analyses are performed. Of note, because CArG elements have been identified in the promoters that control expression of several SMC-specific genes and two functionally important SRF binding sites have been identified in the SM22α promoter (SME-1 and SME-4), particular emphasis is placed on examining the molecular mechanisms underlying the functional activity of the SRF/SME complex in regulating activity of the SM22α. In addition, these studies identify those trans-acting factors that play important roles in regulating the SMC-specificity of SM22α gene expression. These studies begin to define the trans-acting factors that direct arterial SMC-specific gene expression and the molecular program(s) that underlies SMC diversity.

Mutational Analysis of SM22α Promoter

To define the function of specific nuclear protein complexes on SM22α promoter activity, transient transfection analyses are performed as described earlier. However, in these studies more subtle mutations are created in the SM22α promoter that abolish the binding of a specific trans-acting factor (without affecting binding of other factors). To define mutations that abolish binding of a single trans-acting factor, a series of EMSAs are performed as described above. These mutations are guided by the methylation and uracil interference analyses described above. For example, both SRF and YY1 (and two other unrelated nuclear protein complexes) bind to the SME-4 site in the SM22α promoter. EMSAs have revealed that a two nucleotide substitution in the SME-4 site (5 CTCCAACTTGGT-GTCTTTCCCC<u>GG</u>ATATGGAGCCTGTGTGGAGTG 3', SEQ ID NO: 48, mutated nucleotides are underlined) abolishes SRF binding activity, but does not alter other binding activities. In contrast, a distinct two nucleotide substitution (5' CTCCAACTTGGTGTCTTTCCCCAAAT<u>TA</u>GGAGCCTGTGTGGAGTG 3', SEQ ID NO:49) blocks YY1 binding activity, but does not affect any other binding activity. To create mutations that selectively abolish binding of SRF or YY1 to the SME-4 site within the context of the SM22α promoter, gapped heteroduplex oligonucleotide-mediated or PCR™-mediated site directed mutagenesis are performed as described previously (Parmacek et al., 1992). To determine the effect of SRF- versus YY1-binding (at the SME-4 site) on SM22α promoter activity, luciferase reporter plasmids under the transcriptional control of the SRF and YY1 SM22α promoter mutants, respectively, are transiently transfected into primary cultures of rat aortic SMCs and their activities compared to the native SM22α promoter containing plasmid, p-441SM22-luc. If, SRF (and SRF accessory factors) binding to SME-4 activates SM22α promoter activity, the normalized luciferase activity in cells transfected with the p-441SM22m4/SRF plasmid (which ablates SRF binding at the SME-4 site) is less than that obtained with the p-441SM22-luc plasmid. Similarly, if YY1 acts as a positive regulatory factor at the SME-4 site, the normalized luciferase activity in SMCs transiently transfected with the p-441SM22m4/YY1 plasmid (which ablates binding of YY1 at the SME-4 site) is less than that obtained in cells transfected with the p-441SM22-luc plasmid. Alternatively, if YY1 binding to the SME-4 site decreases SM22α promoter activity (i.e., YY1 functions as a negative regulatory factor), cells transfected with he p-441SM22m4/YY1 plasmid have increased levels of luciferase activity. In addition, multiple cis-acting elements are mutated within the context of the p-441SM22-luc plasmid to determine the function of trans-acting factors that bind to multiple cis-acting elements within the SM22α promoter. If a nuclear protein complex is identified that is expressed exclusively in non-SMC lineages (potentially a suppressive factor), then the nuclear protein binding site that binds this complex is mutagenized within the context of the p 441SM22luc reporter plasmid and its transcriptional activity compared to the native 441-bp promoter in non-SMC lines. As it is likely that several of the nuclear protein complexes identified by EMSA share common binding sites, these studies may only be capable of assigning functional activity to one of several nuclear protein complexes. However, elucidation of the precise contact residues between each nuclear protein complex and its cognate binding site can, in some cases, permit the assignment of functional activity to a specific nuclear protein complex. Finally, particularly informative promoter mutants are analyzed in vivo by breeding and histochemically and biochemically analyzing transgenic mice in which the bacterial lacZ is placed under the transcriptional control of the SM22α promoter mutants as described earlier.

Examination of the Molecular Mechanisms Underlying the Functional Activity of SRF and YY1 on SM22α Promoter Activity An alternative approach to determine the function of a transcription factor is to over-express a dominant negative form of the transcription factor and examine its effect on activity of a reporter plasmid. For example, it has been recently demonstrated that expression of a dominant negative mutant SRF protein, designated SRF pm1 (Johansen and Prywes, 1993), that contains a three amino substitution in the DNA-binding domain of SRF, blocks transcriptional activation of the α-skeletal actin and c-fos promoters. (Presumably this mutant protein functions in a dominant negative fashion by dimerizing with native SRF inhibiting the native protein from binding DNA and/or binding critical transcription factors that bind directly to SRF.) To determine whether SRF expressed in arterial SMCs activates transcription of the SM22α promoter, the pCGNpm1 eukaryotic expression plasmid, encoding a flu-epitope tagged SRF pm1 mutant protein (obtained from R. Prywes, Columbia University), and the p-441SM22-luc reporter plasmid are transiently co-transfected into primary rat aortic SMCs and the SMC-line, A7r5, at various molar ratios as described previously (Parmacek et al., 1994). Expression of the dominant negative protein in SMCs are confirmed by performing western blot analyses on representative cell lysates using a monoclonal antibody that recognizes the flu-epitope tag as described previously (Chang et al., 1995). The normalized luciferase activity are compared to that obtained in cells transfected with the p-441SM22-luc reporter plasmid and the pcDNA3 negative control expression plasmid. As a positive control, a luciferase reporter plasmid containing the c-fos promoter is co-transfected with and without the pCGNpm1 expression plasmid as described above. Finally, to prove that the dominant negative protein is acting specifically, as opposed to squelching transcription, the pCGNpm1 expression plasmid is transiently co-transfected into SMC cultures with several non-SRE-dependent promoters. The demonstration that SM22α promoter activity is down-regulated, or abolished, when a dominant negative SRF protein is expressed would suggest that SRF is activating transcription of the SM22α promoter in arterial SMCs.

The demonstration that the SM22α gene is expressed at high levels in medial SMCs, but the gene expression is down-regulated to non-detectable levels in "synthetic SMCs" located within atherosclerotic plaques (Shanahan et al., 1994), suggests that both positive and negative regulatory mechanisms control expression of the SM22α gene in arterial SMCs. EMSAs (see FIG. 4A and FIG. 4B) revealed that an oligonucleotide probe corresponding to the SME-4 binds both SRF (a positive regulatory factor when activated (Johansen and Prywes, 1995)) and YY1 (which can either activate or suppress transcription (Natesan and Gilman, 1995a)). In C2C12 skeletal myoblasts, it has been demonstrated that YY1 binds CArG box sequences (similar to those present in SME-4) in such a way that it antagonizes SRF action (Gualberto et al., 1992). Moreover, over-expression of YY1 in C2C12 myoblasts has been shown to inhibit differentiation of skeletal myoblasts to terminally differentiated myotubes (Lee et al., 1992). These data are consistent with the hypothesis that protein-protein and protein-DNA interactions that occur at the SM22α SME-4 nuclear protein binding site serve to activate transcription by binding transcriptional activators such as SRF (and associated proteins), or suppress transcription by binding preferentially to suppressive factors such as YY1. To test this hypothesis, the pcDNAYY1 expression plasmid, which encodes the mouse YY1 protein, is transiently co-transfected with the p-441SM22-luc reporter plasmid into primary rat aortic SMCs and the luciferase activity compared to that of cells transiently co-transfected with the p-441SM22-luc plasmid and the negative control expression plasmid, pcDNA3 (in the same molar ratios). To determine whether the suppressing (or activating) effect of YY1 is dependent upon its DNA-binding activity, the p-441SM22-luc plasmid is transiently co-transfected into primary rat aortic SMCs with the pcDNAmYY1 expression plasmid that encodes a mutant YY1 protein that cannot bind DNA. To determine whether the effect of YY1 on SM22α promoter activity is dependent on binding directly to the SM22α promoter (a direct effect versus an indirect effect), the YY1 expression plasmid is co-transfected with a luciferase reporter plasmid under the transcriptional control of the SM22α promoter which has been mutagenized to abolish YY1 binding activity. Finally, to determine whether YY1-induced suppression of SM22α promoter activity (if it exists) can be overcome by over-expression of SRF (suggesting a direct antagonism between YY1 and SRF) transient co-transfection studies is performed as described above except that expression plasmids encoding both YY1 and SRF are included and their ratios varied over a range of concentrations. The demonstration that over-expression of YY1 suppresses transcription from the SM22α promoter would suggest that, as in skeletal muscle cells, YY1 acts as a negative regulatory factor. Conversely, the demonstration that over-expression of YY1 increases SM22α promoter activity would suggest (but not prove) that, as with the c-fos promoter, YY1 acts as a positive regulatory factor (Natesan and Gilman, 1995b).

Transactivation of the Arterial SMC-specific SM22α Promoter in Non-SMCs

To identify transcription factor(s) that play important roles in regulating SMC-specificity of SM22α gene expression, transient co-transfections are performed in non SMC lineages such as NIH3T3 cells to elucidate the role of GATA-4/5/6 subfamily members in regulating cardiac-specific transcription as described previously (Ip et al., 1994; Morrisey et al., 1996). Of note, these studies are performed after SMC lineage-restricted transcription factor(s) are cloned and structurally characterized, or whenever a candidate regulator of the SMC lineage(s) is identified. For example, to determine whether the mesodermally-expressed homeodomain transcription factor MHox can transactivate the SM22α promoter in non-SMCs, NIH 3T3 cells are transiently transfected with the p-441SM22-luc reporter plasmid and the eukaryotic expression plasmid encoding the full-length MHox protein, pEMSVMHox (obtained from Eric N. Olson), in varying molar ratios (this ratio can vary greatly and must be empirically determined) as described previously (Parmacek et al., 1994). As a negative control, the −441SM22luc plasmid is co-transfected with the pEMSV expression plasmid lacking a cDNA insert and the normalized luciferase activities obtained following transfection with the pEMSVMHox and pEMSV expression plasmids compared. To confirm that activation of the SM22α promoter is CArG dependent, the MHox expression plasmid is co-transfected with the plasmid designated p 441SM22mCArG which contains mutations in both the SME-1 and SME-4 nuclear protein binding sites that abolish SRF binding. Next, to determine whether DNA-binding activity of the MHox protein is required to activate transcription of the SM22α gene, the cDNA encoding the (DN144Q)MHox mutant protein which cannot bind DNA (Gmgeneberg et al., 1992) is subcloned into the pEMSV expression vector and its ability to transactivate the p-441SM22luc reporter plasmid compared to the pEMSVM-Hox expression plasmid. If both the native and mutant MHox expression plasmids increase transcription of the luciferase reporter to equivalent levels, the ability of MHox (or related homeobox proteins) to activate transcription of the SM22α promoter does not require direct protein-DNA interaction. Of note, while typically co-transfection studies do not require that all of the transcription factors that activate a specific lineage-specific promoter be present in the recipient cell line (Ip et al., 1994), it is possible that NIH 3T3 cells do not express a specific transcription factor unrelated to SRF that is required for SM22α promoter function. In this case, other non-SMC cell lines which do not express MHox including COS-1, F9, and P19, are tested in co-transfection studies as described above.

EXAMPLE 14

Cloning and Characterization of Novel SMC-Specific Transcription Factors that Regulate Activity of the SM22α Promoter Current developmental paradigms suggest that lineage-specific gene expression is ultimately controlled by the expression of lineage-specific transcription factors (Olson, 1990; Olson, 1993; Olson et al., 1991; Olson and Klein, 1994; Tapscott and Weintraub, 1991). Preliminary characterization of these factors have revealed SMC-lineage restricted factors that bind to SME-3 and non-SRF related nuclear protein complexes that bind to SME-1 and SME-4 in conjunction with SRF. Novel SMC-specific transcription factors may be cloned using any of three complementary approaches. (1) Oligonucleotide affinity chromatography is performed to purify SMC-lineage restricted trans-acting factors that regulate activity of the SM22α promoter. Following purification, these factors are cloned and structurally characterized by raising antiserum against the purified protein and using these antibodies as probes to perform λgt11 library expression screening. (2) Alternatively, microsequence analysis of the purified protein factions are performed followed by oligonucleotide hybridization or PCR™-based library screening based on the partial amino acid sequence analysis. This approach offers the advantages of isolating transcription factors that bind to DNA only as a multi-protein complexes and each step of the protein purification procedure can be evaluated critically. However, it has the potential disadvantage of requiring large amounts of starting material and its success is to some extent dependent upon the level of protein expressed and the biochemical properties of the protein. (3) In a complementary seres of studies, a λgt11 mouse aortic cDNA is screened with a radiolabeled oligonucleotide probe corresponding to a particular SME as described originally by Singh et al. (Singh et al., 1988). While this approach is relatively straightforward, this cloning approach only detects transcription factors that bind as a single protein or homodimer. Finally, it is possible that a novel SMC-specific trans-acting factor regulates activity of the SM22α promoter via direct protein-protein rather than protein-DNA interactions. To identify these potential SMC-specific transcription factors, two alternative yeast screening selection strategies are employed.

Oligonucleotide Affinity Chromatography

Nuclear proteins that bind to the SM22α promoter are isolated by sequence-specific oligonucleotide affinity chromatography as originally described by Tijan and coworkers (Briggs et al., 1986; Kodonaga and Tijan, 1986). This approach has successfully been utilized to isolate several transcription factors which bind DNA as homodimers, heterodimers or multi-protein complexes (Briggs et al., 1986; Kodonaga and Tijan, 1986). The following protein purification strategy is modified empirically based on biochemical properties of the isolated protein. The key purification step in this strategy is oligonucleotide affinity chromatography which has been demonstrated to result in an 80-fold purification of protein (Kodonaga and Tijan, 1986). For the sake of clarity, only a strategy to isolate SME-3 binding factors (a SMC-lineage specific nuclear protein complex has been identified in EMSAs, see FIG. 5B) is presented. However, the protocol described with minor variations is used to isolate other functionally important lineage-restricted nuclear proteins that bind directly (as determined by EMSAS) to the SM22α promoter. 500 mg-1 g of A7r5 nuclear extract (which contains the lineage restricted SME-3 binding activity) is prepared as described previously (Parmacek et al., 1992). Ammonium sulfate fractionation are performed and the precipitated protein separated by Sephacryl S-300 gel filtration. In addition, if necessary additional purification steps including heparin sepharose chromatography and FPLC Mono Q (Pharmacia). Samples containing peak SME-3 binding activity are pooled and subjected to sequential DNA affinity chromatography as described by Kadonaga and Tijan (Kodonaga and Tijan, 1986). An SME-3 DNA affinity resin and a mutated SME-3 affinity resin are generated by covalently linking tandemly ligated copies of the 42-bp double-stranded SME-3 oligonucleotide sequence or the mutated SME-3 oligonucleotide sequence, respectively, to cyanogen bromide-activated Sepharose. (Of note, EMSAs and methylation interference analyses are performed in order to define an oligonucleotide sequence (derived from the SME-3 sequence) which binds exclusively to the SMC-specific nuclear protein complex of interest). This technique results in a matrix containing oligomers of the oligonucleotide ranging in size from 3–75 copies. The pooled fractions are mixed with nonspecific competitor DNA, such as calf thymus DNA or poly dI:dC, and applied to the mutated SME-3 affinity resin in order to remove proteins that non-specifically bind to the SME-3 oligonucleotide and column matrix. The column is then washed with 0.1 M KCl and eluted in a multiple step gradient (0.2 M KCl to 1.0 M KCl). The eluted fraction containing SME-3 binding activity is applied to the wild type SME-3 affinity resin, washed and eluted as described above. In all of the purification steps, SME-3 binding activity is assayed from column fractions by performing EMSAs with a radiolabeled SME-3 oligonucleotide probe. Of note, using this protocol, Tijan and coworkers (Jones et al., 1987; Kodonaga and Tijan, 1986) have demonstrated a cumulative gain in specific activity of approximately 30,000–50,000-fold/mg protein and a cumulative yield of approximately 0.002%. Thus, if one starts with 1 g of nuclear extract, one would expect approximately 20 mg of purified protein utilizing this strategy. If successful (i.e., purification to greater than 95% homogeneity), this amount of protein is sufficient for microsequence analysis and/or sufficient to raise a specific antisera directed against the putative SME-3-binding protein(s).

The recovery of SME-3 binding activity and the relative extent of purification is analyzed by SDS-PAGE and EMSAs. Following affinity chromatography, protein fractions which bind DNA are visualized by SDS-PAGE and silver staining as described previously (Samarel et al., 1987). To demonstrate which of the polypeptide species isolated by DNA affinity chromatography and visualized by PAGE represent SME-3 binding activity, approximately 2–3 mg of purified protein are separated by preparative SDS-PAGE and the region of the gel containing the major polypeptide species is excised and eluted from the polyacrylamide gel in 50 mM Tris, pH 7.9, 0.1 mM EDTA, 0.1% SDS, 5 mM DTT, and 150 mM NaCl. SDS is removed by acetone precipitation, and the precipitated protein is resuspended in TM buffer (50 mM Tris, pH 7.9, 12.5 mM MgCl2, 1 mM EDTA, 1 mM DTT, 20% glycerol) containing 0.1 M KCl, 0.1% NP40, and 6M guanidine HCl to denature the polypeptide chains as described previously (Kodonaga and Tijan, 1986). The guanidine HCl is removed by gel filtration to facilitate refolding of the polypeptide chains and recovery of DNA binding activities as determined by EMSA and DNase I footprinting is assessed. Of note, the net yield after these two steps is approximately 20% (Briggs et al., 1986; Jones et al., 1987; Kodonaga and Tijan, 1986). In the EMSAs, a control sample containing excised and renatured proteins from other regions of the gel, and also non-renatured protein are run as controls. Of note, several eukaryotic transcription factors including Sp1 (Briggs et al., 1986), AP-1 (Kodonaga and Tijan, 1986), and bacterial transcription factors including sigma factors (Helmann and Chamberlin, 1988) have been functionally reconstituted using this technique.

To more precisely characterize the SME-3 binding protein (s), the individual proteins of the SME-3 complex are purified as described above, and undergo amino acid sequence analysis. Tryptic peptides are generated, resolved by reverse phase HPLC, and sequenced using an Applied Biosystems gas phase sequencer. These sequences are compared against the GenBank and NBRF data basis to determine if they correspond to previously described proteins or genes. In addition, polyclonal rabbit anti-SME-3 antiserum are prepared as described previously (Ip et al., 1994). Antiserum is screened for activity by western blotting and immunoprecipitation of A7r5 nuclear extracts as described above. If this is not successful, synthetic peptides derived from the microsequence analyses of the SME-3 binding proteins are used to immunize rabbits. The sizes of the proteins identified by these western blotting and immunoprecipitation approaches are compared to those determined in the UV-crosslinking studies described above. In a complementary set of studies, it is determined if the antisera recognize the SME-3 binding activities by EMSA as described above. The demonstration that the antiserum raised against the SME-3-binding protein is able to specifically shift SME-3 nuclear protein complexes and pre-clear SME-3 binding activity from SMC extracts is strong evidence in favor of the authenticity of the SME-3-binding protein. Finally, to fully characterize each DNA binding protein, oligo-dT primed and random primed mouse aortic λgt11 cDNA libraries are screened, using the antisera raised against the SME-3 binding protein as described (Gottesdiener et al., 1988). In addition, PCR™-based screening of these libraries is performed with redundant synthetic oligonucleotide primers derived from the amino acid sequence analysis of the tryptic peptide fragments which are generated from the SME-3 microsequence analysis performed above as described (Wilkie and Simon, 1991).

λgt11 Library Screen

To clone cDNAs encoding proteins that bind to functionally important nuclear protein binding sites within the SM22α promoter, a large ($8\times10^6$ recombinants) randomly primed λgt11 cDNA library has been constructed using poly $A^+$RNA prepared from the aorta of 6 wk. old Balb/C mice. This library is screened for functionally important SMC-specific SM22α promoter binding activities using a radiolabeled multimeric oligonucleotide probe corresponding to the nucleotide sequence of the SME to which novel SMC-specific trans-acting factors bind using a modification of the procedure of Singh et al. (Singh et al., 1988) and Staudt et al. (Staudt et al., 1988). Of note, because nucleotides flanking CArG/SRE elements are often required to isolate factors that bind in conjunction with SRF (Johansen and Prywes, 1995), in order to isolate factors that bind to SME-1 or SME-4 the oligonucleotide probes utilized include 25-bp of 5' and 3' sequence flanking each embedded CArG motif. To isolate the novel SMC lineage-restricted SME-3 binding factors, a radiolabeled SME-3 probe is prepared by annealing of single stranded SME-3 oligonucleotides followed by ligation of overhanging BamHI and BglII ends and nick translation with $[\alpha^{32}P]$-dCTP. $1\times10^6$ phage from the library are plated, incubated for approximately 3.5 h at 41° C., overlaid with nitrocellulose filters that have been presaturated with 10 mM IPTG, and incubated an additional 3.5 h at 37° C. The filter-bound proteins are then denatured and renatured through guanidine HCl and HEPES binding buffers (this step is optional) and blocked with Blotto. Filter hybridization is performed for 1 h at 25° C. in a solution containing $2\times10^6$ DPM/ml of radiolabeled probe, TNE 50 (10 mM Tris, pH 7.5, 50 mM NaCl, 1 mM EDTA and 1 mM DTT) and denatured calf thymus DNA. Following hybridization, filters are washed in TNE 50, dried and autoradiography is performed to identify positively hybridizing clones. The specificity of binding is tested by hybridizing tertiary filters to radiolabeled SME-3 and mutant SME-3 (mutations which inhibited binding are confirmed by EMSAs), as well as, unrelated oligonucleotide probes. Only cDNA that bind to the specific oligonucleotide probe, but not to the mutant and non-specific probes are characterized further. Subsequently, each candidate SME-3 clone is purified to homogeneity by sequential screening with the same radiolabeled probes and the inserts subcloned into pGEM4Z (Promega).

To assess the binding specificity of the proteins encoded by these SME-3 candidate clones, lambda lysogens are made by infecting *E. coli* Y1089 with the SME-3 λgt11 candidate clones at 32° C. Fusion protein expression is induced by temperature shift to 44° C. and IPTG treatment and crude bacterial lysates are prepared as per Singh (Singh et al., 1988). Control lysates are identically prepared from Y1089 lysogens containing wild type λgt11. The SME-3 lysates are tested for SME-3 binding activities by EMSAs (including cold competition studies and EMSAs with mutant SME-3 oligonucleotide) as previously described. In addition, the lysates are subjected to SDS-PAGE and duplicate western blots are screened with either radiolabeled SME-3 oligonucleotide probe (as well as non-specific negative control probe) and with commercially available anti β-galactosidase antibody (Capel).

If the cDNA clone(s) are shown to encode proteins wvhich bind specifically to the SME-3 oligonucleotide, two types of studies are performed to attempt to determine whether they encode the SME-3 binding activities present in SMC nuclear extracts. First, rabbit antisera is raised against the recombinant SME-3 fusion protein and to show that these antisera are both able to recognize SMC nuclear proteins of the same size as those identified in the UV-crosslinking studies described above, and to specifically block the SME-3 binding activities in SMC nuclear extracts. Briefly, SME-3 fusion proteins are prepared from crude lysates of λgt11 lysogens by preparative SDS-PAGE (following staining with 0.1 M KCl) and bands cut from the gels, crushed, and mixed with adjuvant. 5–10 mg of this gel purified fusion protein (in crushed acrylamide) are injected into female rabbits subcutaneously at 2–3 week intervals. Seven days following immunization, serum is collected and extensively preabsorbed by incubation with extracts of wild type λgt11 lysogenized Y1089 in order to remove anti-β-galactosidase and anti-bacterial protein activities. Pre-immune and immune sera are used to probe duplicate western blots containing SDS-PAGE fractionated proteins from the SME-3 lysogens as well as wild type λgt11 lysogens. If specific antisera are not obtained following immunization with fusion proteins, synthetic immunogenic peptides designed from DNA sequence analysis of the cDNA clone(s) using the Hopp and Woods algorithm of the Wisconsin GCG software package (Madison, Wis.) are used to immunize rabbits and the resulting antisera assayed by western blotting as described above. Sera which recognize the SME-3 fusion protein, but not the wild type λgt11 proteins are then assayed for their ability to recognize SME-3 protein from SMCs by western blotting of SMC extracts and by immunoprecipitation of $^{35}$S-methionine labeled SMC nuclear extracts as previously described (Martin et al., 1993). The sizes of the proteins identified by these western blotting and immunoprecipitation approaches are compared to those determined in the UV-crosslinking studies described above. In a complementary set of studies, an attempt to determine whether the antisera recognize the SME-3 binding activity is made by EMSA. In these studies, the radiolabeled SME-3 oligonucleotide is incubated with SMC nuclear extract either in the presence of control (pre-immune) or specific antisera and the resulting complexes assayed by standard EMSA. If the antiserum recognizes one of the nuclear proteins, it should result in a specific further shift upwards in mobility in the gel ("a supershift"). The antisera are also used to preclear SMC nuclear extracts by immunoprecipitation. These pre-cleared extracts are then assayed for SME-3 binding activities by gel mobility shift assays using radiolabeled SME-3 probe. The specificity of preclearing is confirmed by simultaneously assaying the precleared nuclear extracts of another SME by EMSA. The demonstration that the antiserum raised against the recombinant fusion protein is able to specifically shift and preclear SME-3 binding activities from SMC extracts would be strong evidence in favor of the authenticity of the SME-3 candidate cDNA clones.

In a second set of studies, the SME-3 cDNAs are used as hybridization probes on northern blots containing RNA from neonatal and adult murine tissues as well as primary rat aortic SMCs (which contain less than 5% contaminating fibroblasts) in order to determine the number and sizes of mRNA species corresponding to these cDNAs. If this cDNA is a bona fide SMC-specific transcription factor which is regulated at the level of gene expression, it is expected that it would be expressed at high levels in SMC-enriched tissues such as the aorta and in primary rat aortic SMCs (it is extremely likely that the mouse and rat cDNA clones cross-hybridize). However, it is also possible that SME-3 candidate cDNA represents a ubiquitously expressed transcription factor which binds to the SME-3 binding site, or that the bona fide gene which encodes SME-3 mRNA respectively is expressed in multiple cell lineages and its activity in SMCs is regulated at the translational or post-translational level. Thus, the finding that SME-3 mRNA is not restricted to SMCs does not rule out its authenticity as a bona fide SME-3 binding factor which may bind specifically in vascular SMCs. Once the SME-3 cDNA clone(s) are authenticated in the studies described above, full length clones for DNA sequence analysis are isolated. Full length clones are either obtained directly or assembled from overlapping cDNAs obtained by screening the large oligo-dT primed and random hexamer-primed murine aortic λgt11 libraries with probes from the 5' and 3' ends of the SME-3 cDNA. cDNAs are subcloned into pGEM4Z and sequenced directly from double stranded plasmid DNA as described previously (Solway et al., 1995). cDNA sequences are analyzed using the MacVector software package (Oxford) and the GenBank and NBRF databases are searched in order to detect similarities with previously described proteins and genes.

If these approaches are unsuccessful in identifying SME-3 cDNA clones, an alternative cDNA expression cloning approach can be used. A large randomly primed cDNA library is constructed with poly A+ mouse aorta RNA in the commercially available pCDM8 vector. In this vector, transcription of cDNAs is under the control of a CMV promoter. In addition, the vector contains an SV40 origin of replication to allow high copy amplification in COS cells. Pools of 5,000 clones of this cDNA library are transfected into COS cells and nuclear extracts are prepared from the transfected cells after 72 h. These nuclear extracts along with control extracts from mock-transfected COS cells are assayed for SME-3 binding activity by EMSAs. If one or more pools are found to encode the SME-3 binding activity, cDNA clones encoding SME-3 are isolated by sib-selection using EMSAs. Of note, this approach was used by Orkin and co-workers to isolate the erythroid specific transcription factor, NF-E2 (Orkin, 1992). The success of this technique depends upon the untransfected COS cell nuclear extracts not displaying this potentially novel SME-3 binding activity.

Yeast Two Hybrid Screen

A number of studies suggest that interactions between MADS box transcription factors and lineage-restricted accessory proteins could establish cell identity, in part, by determining which genes are activated in response to generic inductive signals which are transduced by (Marais et al., 1993; Mueller and Nordheim, 1991; Pellegrini et al., 1995) ubiquitously-expressed transcription factors such as SRF (Cserjesi et al., 1994; Grueneberg et al., 1992). As discussed above, the SM22α promoter contains tandem binding sites for the MADS box transcription factor SRF (SME-1 and SME-4) suggesting that protein-protein interactions between SRF and other accessory factors expressed in SMCs could regulate SMC-specific transcription. One approach that has been successfully utilized to isolate cDNA clones that bind directly to a transcription factor is to perform a genetic screen in yeast (Fields and Song, 1989). Of note, an advantage of this strategy is that it is based on in vivo interactions between proteins when they are expressed in their native conformation. However, an inherent limitation of the yeast two hybrid screening strategy is that it is dependent upon functional complementation by a single cDNA (or deduced protein). Despite this limitation, similar strategies have successfully identified many functionally important protein partners (Dalton and Treisman, 1992; Grueneberg et al., 1992). Moreover, as described above, the alternative (and complementary) strategy of oligonucleotide affinity chromatography (which is not bound by this potential limitation), are also performed.

Initially, a modification of the yeast screening selection strategy employed by Dalton and Treisman to isolate SAP-1 from a HeLa cell cDNA library (Dalton and Treisman, 1992) is used. This strategy offers the advantage of isolating proteins that require both protein-protein interaction (with SRF) and specific protein-DNA binding (to the SME-1 or SME-4) to activate transcription. Because the yeast MADS box transcription factor MCM1 binds to some CArG/SRE elements (which would preclude their use in the library screen described below), it is first determined whether MCM1 binds to the SM22α SME-4 (or SME-1) site by EMSA and by two hybrid complementation studies in yeast as described (Nurrish and Treisman, 1995). Of, note 9 out of 10 nucleotides in the SME-4 CArG/SRE motif (5' CCAAATATGG 3', SEQ ID NO:50) are identical to the nucleotides that compose the skeletal α-actin CArG box (5' CCATATATGG, SEQ ID NO:51) which binds exclusively to SRF (and not to MCM1) (Nurrish and Treisman, 1995). To prepare the yeast indicator stain, double stranded oligonucleotides corresponding to the SME-4 nuclear protein binding site and 25-bp flanking the embedded CArG/SRE motif are subcloned into the XhoI site 5' of the CYC1 TATA box in the CYC1/LacZ reporter plasmid, pLGD-178 (Guarente et al., 1982). The SME-4/lacZ reporter gene is excised as an XhoI-NcoI fragment and inserted into the StuI site of pURA3 (Dalton and Treisman, 1992), thereby embedding the reporter gene in the *S. cerevisiae* URA3$^+$ coding region. Each URA3 disruption plasmid is digested with HindIII to release the URA3 reporter sequences and is cotransformed with a TRP1$^+$ marker plasmid (pRS314) into the URA3$^+$ *S. cerevisiae* strain S50 (HMLα, MATα, HMRa, his3-11, 15, trp1-1, ade2-1, leu2-3, 112, URA3$^+$ ho, can1-100) by spheroplast transformation as described (Hinnen et al., 1978). Several hundred Trp+ transformants are pooled, resuspended in minimal medium (minus amino acids) and selected for resistance to 5-fluorotic acid (5-FOA, Sigma). Individual colonies are picked from the 5-FOA plates, re-purified, streaked on ura- selective plates, and checked by Southern blot analysis to confirm disruption of the URA3$^+$ locus by the reporter gene. Next, the low copy plasmid, pSD.07 (Dalton and Treisman, 1992), that permits galactose-inducible expression of SRF and contains the TRP1+ marker are transformed into the Y.SME-4 cells creating the Y.SME-4/SD.07 indicator strain.

For these studies, a VP16-tagged rat aortic SMC cDNA library is prepared by cloning randomly primed mouse aortic cDNA into the BstX1 site of the yeast expression vector pSD.10 (this vector permits galactose-inducible expression of the fusion protein) as described previously (Solway et al., 1995). A culture of Y.SME-4/SD.07 is transformed with the VP16-tagged cDNA library, plated on nylon filters and grown on ura- trp- selective glucose medium for 32–38 hours at 30° C. Filters are then transferred to galactose plates for a further 18 h to induce expression of both the cDNA library and SRF. A colony color β-galactosidase activity assay is then performed as described by Breeden and Nasmyth to identify lacZ-positive (blue) colonies (Breeden and Nasmyth, 1987). Blue colonies are patched on selective medium containing 2% glucose, purified (by growth in ura- trp- selective broth) and plated. After 48 h at 30° C., single colonies are replica plated onto nylon filters and retested for colony color. To test whether the positive colonies require the presence of the VP16/cDNA fusion protein or SRF, cells are cured of the URA1+ cDNA (which is carried on the pSD.10 vector) or TRP1+ (which is carried on the SRF expression plasmid) plasmids and retested for β-galactosidase activity. Of note, this will serve to distinguish SMC cDNA clones that activate the reporter plasmid in the absence of SRF (approximately 25% of clones (Dalton and Treisman, 1992)) which is a potential artifact of the two-hybrid strategy. VP16/cDNA plasmids are then recovered from strains cured of the TRP1+ plasmid (SRF expression plasmid), transformed into bacteria, isolated and characterized as described.

Alternatively, a standard yeast two hybrid screen is performed. Of note, in contrast to the screening strategy described above, this strategy only isolates those trans-acting factors that bind to SRF in a non- DNA-dependent fashion. In these studies the yeast indicator strain HF7c (ura3-52, his3-200, lys2-801, ade2-101, trp1-901, leu2-3, 112, gal4-542, gal80-538, LYS2::GAL1-HIS3, URA3::GAL4-lacZ) (Clontech) which carries the GAL1-HIS3 and GAL4-lacZ reporters and the trp1, leu2 transformation markers are utilized. This strategy offers the potential advantage of utilizing "bait plasmids" that encode specific domains of the SRF protein (as opposed to the fill-length SRF protein) (Johansen and Prywes, 1993) thereby decreasing background from proteins that interact non-specifically with SRF. SRF domains that are subcloned into the pGBT9 plasmid (Clontech) include cDNAs encoding amino acids 168–222 (the TCF interaction domain), amino acids 1–406 (the entire SRF protein except the C-terminal activation domain), amino acids 406–476 (the C-terminal activation domain) and amino acids 1–508 (the entire SRF protein). Of note, if expression of these proteins is "toxic" to the yeast, or if the SRF activation domain activates transcription from the yeast reporter gene, bait plasmids containing specific mutations in the DNA-binding, homodimerization and transcription activation domains are tested (Johansen and Prywes, 1993; Johansen and Prywes, 1994). A GAL4 activation domain (AD)/mouse aortic cDNA fusion library is utilized that is cloned into the pGAD424 vector (Clontech). HF7c cells are co-transformed with the pGBT9 bait plasmid and the pGAD424 GAL4AD/mouse aortic cDNA expression library as described above and the transformed cultures plated on medium minus tryptamine and leucine to select for cells having both plasmids. In addition, because the HF7c indicator strain is auxotrophic for histidine, but carries a HIS3 gene under the control of the GAL1 UAS, transformation on medium minus histidine selects for plasmids that interact. A β-galactosidase filter assay is then performed as described above to confirm the presence of interacting proteins.

Finally, full-length cDNA clones encoding potentially novel SRF accessory proteins expressed in SMCs are isolated by screening a random primed mouse aortic λgt11 cDNA library using the radiolabeled SMC cDNA (isolated by the yeast screening strategies described) as a probe as described previously (Parmacek and Leiden, 1989; Solway et al., 1995). To determine if the putative accessory protein and SRF interact in mammalian cells, NIH 3T3 cells are transiently co-transfected with a luciferase reporter plasmid, pSME-4TKluc, that contains a multimerized SME-4 oligonucleotide positioned 5' of the minimal HSV TK promoter driving expression of the firefly luciferase gene (the p-441SM22luc plasmid which contains two CArG elements is also tested) and an expression plasmid, designated pVP16SMCDNA3, containing the VP16 activation domain fused in-frame to the open reading frame of the novel cDNA in the pcDNA3 eukaryotic expression plasmid. Of note, SRF is normally expressed in NIH 3T3 cells, yet the minimal SRE-linked HSV TK promoter is relatively inactive in these cells (Dalton and Treisman, 1992). Therefore, if the accessory protein and SRF functionally synergize in mammalian cells, co-transfection of the CArG-dependent luciferase reporter plasmid and the cDNA expression plasmid should increase transcription of the luciferase reporter gene above levels obtained following co-transfection of pSRETKluc and an unrelated VP16-linked cDNA expression plasmid. To determine whether activation requires DNA binding by SRF, co-transfection is repeated using a luciferase reporter plasmid that contains mutations in the multimerized CArG motifs. Finally, to examine the molecular mechanisms underlying the functional activity of the SMC accessory factor, EMSAs are performed using the in vitro translated protein isolate and SRF at different ratios. Taken together, these studies should identify and functionally characterize each transcription factor(s) expressed in SMCs that regulates activity of the SRF/SME complex. Moreover, these studies may directly isolate novel SMC-lineage restricted transcription factors that function in concert with SRF in regulating transcription of the SM22α gene.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aikawa, M., Sivam, P. N., Kuro-o, M., Kimura, K., Nakahara, K., Takewaki, S., Ueda, M., Yamaguchi, H., Yazaki, Y., Periasamy, M., and Nagai R. (1993) Circ. Res. 73, 1000–1012.

Akira, S., Isshiki, H., Sugita, T., Tanabe, O., Kinoshita, S., Nishio, Y., Nakajima, T., (1990) EMBO J., 1897–1906.

Ayme-Southgate, A., Lasko, P., French, C. and Pardue, M. L. (1989) J. Cell Biol. 108, 521–531.

Barr, E., Carroll, J., Kalynych, A. M., Tripathy, S. K., Kozarsky, K., Wilson, J. M. and Leiden, J. M. (1994) Gene Therapy 1, 51–58.

Belkin, A. M., Ornatsky, O. I., Kabakov, A. E., Glukhova, M. A., and Kotteliansky, V. E. (1988) J, Biol. Chem. 263, 6631–6635.

Blank, R. S., McQuinn, T. C., Yin, K. C., Thompson, M. M., Takeyasu, K., Schwarz, R. S., and Schwartz, R. J., and Owens, G. K. (1992) J. Biol. Chem. 267, 984–989.

Breathnach, R., and Chambon, P. (1981) Annu. Rev. Biochem. 50, 349–383.

Carroll, S. L., Bergsma, D. J., and Schwarz, R. J. (1988) J. Biol Chem. 261, 8965–8976.

Chang, M. W., Barr, E., Seltzer, J., Jiang, Y. Q., Nabel, G. J., Nabel, E. G., Parmacek, M. S. and Leiden, J. M. (1995) Science 267, 518–522.

Chaponnier, C., Kocher,O., Gabbiani, G. (1990) Eur. J. Biochem. 190, 559–565.

Chen, P.-L. et al. (1989) Cell 58, 1193.

Chodosh et al., (1986) Mol. Cell. Biol., 6, 4723–4733.

Chomczynski, P. (1993) Biotechniques 15, 532–537.

Devlin, B. H., Wefald, F. C., Kraus, W. E., Bernard, T. S., and Williams, R. S. (1989) J. Biol. Chem. 264, 13896–13901.

Dierks, P., man Ooyen, A., Cochran, M. D., Dobkin, C., Reiser, J., and Weissmann, C. (1983) Cell 32, 695–706.

Duband, J. L., Gimona, M., Scatena, M., Sartore, S., and Small, J. V. (1993) Differ. 55, 1–11.

Dynan, W. S., and Tijan, R. (1983) Cell 35, 79–87.

Edmondson, D. G., Cheng, T. C., Cserjesi, P., Chakroborty, T., and Olson, E. N. (1992) Mol. Cell. Biol. 12, 3665–3677.

Evans, T., Reitman, M., and Felsenfeld, G. (1988) Proc. Natl. Acad. Sci. (USA) 85, 5976–5980.

Forrester, J. S., Fishbein, M., Helfant, R. and Fagin, J. (1991) J. Am. Coll. Cardiol. 17, 758–769.

Frampton et al., (1990) Mol. Cell. Biol., 10, 3838–3842.

Frid, M. G., Printesva, O. Y., Chiavegato, A., Faggin, E., Scatena, M., Koteliansky, V. E., Pauletto, P., Glukhova, M. A., and Satore, S. (1993) J. Vasc. Res. 30, 279–292.

Gabbiani, G., Kocher, O., Bloom, W. S., Vandekerckhove, J. and Weber, K. (1984) J. Clin. Invest. 73, 148–152.

Ghosh-Choudhury and Graham (1987) Biochem. Biophys. Res. Comm. 147: 964–973.

Gimona, M., Sparrrow, M. P., Strasser, P., Herzog, M., and Small, J. V. (1992) Eur. J. Biochem. 205, 1067–1075.

Gimona, M., Herzog, M., Vandekerckhove, J. and Small, J. V. (1990) FEBS Letters 274, 159–162.

Glukhova, M. A., Kabakov, A. E., Frid, M. G., Ornatsky, O. I., Belkin, A. M., Mukhin, D. N., Orekhov, A. N., Koteliansky, V. E., and Smirnov, V. M. (1988) Proc. Natl. Acad. Sci. USA. 85, 9542–9546.

Gluzman et al., (1982) in Eukaryotic Viral Vectors (Gluzman, Y., Ed.) pp. 187–192, Cold Spring Harbor Press, Cold Spring Harbor, N.Y.

Gonzalez-Crussi, F. (1971) Am. J. Anat. 130, 441–460.

Gossett, L. A., Kelvin, D. J., Sternberg, E. A., and Olson, E. N. (1989) Mol. Cell. Biol. 9, 5022–5033.

Graham, F. L. and A. J. van der Eb. (1973). A new technique for the assay of infectivity of human adenovirus 5 DNA. Virology 52: 456–467.

Graham, F. L. and Prevec, L. Manipulation of adenovirus vectors. In: Murray E. J. (ed.), Methods in Molecular Biology, Gene Transfer and Expression Protocols, pp. 109–128. New Jersey: The Humana Press Inc, 1991.

Graham, F. L., J. Smiley, W. C. Russell and R. Nairn (1977). Characteristics of a human cell line transformed by DNA from human adenovirus type 5. J. Gen Virol. 36:59–72.

Grepin, C., Dagnino, L., Robitaille, L., Haberstroh, L., Antakly, T., and Nemer, M. (1994) Mol. Cell. Biol. 9, 5022–5033.

Gustafson, T. A., Miwa, T., Boxer, L. M. and Kedes, L. (1988) Mol. Cell. Biol. 8, 4110–4119.

Hasty, P., Bradley, A., Morris, J. H., Edmondson, D. G., Venuti, J. M., Olson, E. N., and Klein, W. H. (1993) Nature (London) 364, 501–506.

Hirakow, R. and Hirum, T. (1981) Anat. Embryol. 163, 299–306.

Hirano, T., and Kishimoto, T. (1990) EMBO J. 9, 1897–1906.

Hollingsworth, R. E., Hensey, C. E. and Lee, W.-H. (1993) Curr. Opin. Genet. Dev. 3, 55.

Hood, L. C. and Rosenquist, T. H. (1992) Anatomical. Record. 234, 291–300.

Ip, H. S., Wilson, D. B., Heikinheimo, M., Tang, Z., Ting, C. N., Simon, M. C., Leiden, J. M. and Parmacek, M. S. (1994) Mol. Cell. Biol. 14, 7517–7526.

James, A. L, Pare, P. D., and Hogg, J. C. (1989) Am. Rev. Respir. Dis. 139, 242–246.

Jaynes, J. B., Johnson, J. E., Buskin, J. N., Gartside, C. L., and Hauschka, S. D. (1988) Mol. Cell. Biol. 8, 62–70.

Kodonaga and Tijan, (1986) Proc. Natl. Acad. Sci. USA, 83, 5889–5893.

Kretsinger, R. H. (1980) CRC *Crit. Rev. Biochem.* 8, 119–174.
Lassar, A. B., Buskin, J. N., Lockshon, D., Davis, R. L., Apone, S., Hauschka, S. D., and and Weintraub, H. (1989) *Cell* 58, 823–831.
Lees-Miller, J. P., Heeley, D. H., Smillie, L. B. and Kay, C. M. (1987) *J. Biol. Chem.* 262, 2988–2993.
Leiden, J. M. (1994) *Mol. Cell. Biol.* 14, 1870–1885.
Lelievre, C. C. and Ledouarin, N. M. (1975) *J. Embryo. Exp. Morphol.* 34, 125–154.
Lilly, B., Zhao, B., Ranganayakulu, G., Paterson, B. M., Schulz, R. A., and Olson, E. N. (1995) *Science.* 267: 688–693
Liu, M. W., Roubin, G. S., King, S. B. (1989) *Circ.* 79, 1374–1387.
McGrory, W. J. et al. (1988). A simple technique for the rescue of early region I mutations into infectious human adenovirus type 5. *Virology* 163: 614–617.
Miano, J., Cserjesi, P., Ligon, K., Periasamy, M., and Olson, E. N. (1994) *Circ. Res.* 75, 803–812.
Miller 1992, Curr. Top. *Microbiol. Immunol.* 158:1.
Min, B., Foster, D. N., and Strauch, A. R. (1990) *J. Biol. Chem.* 265, 16667–16675.
Minty, A., and Kedes, L. (1986) *Mol. Cell. Biol.* 6, 2125–2136.
Miskimins et al. (1985) *Proc. Natl. Acad. Sci. USA,* 82, 6741–6744.
Mitchell, P. J., Wang, C., and Tijan, R. (1987) *Cell* 50, 847–851.
Morrisey, Ip, H. S., Lu, M. M. and Parmacek, M. S. (1996) *Dev. Biol.,* 177:309–322.
Mosse, P. R., Campbell, G. R., Wung, Z. L., Campbell, J. H. (1985) *Lab Invest.* 53, 556–562.
Murphy, M. E. and Carlson, E. C. (1978) *Am. J. Anat.* 151, 345–375.
Nabel, E. G., Pompili, V. J., Plautz, G. E. and Nabel, G. J. (1994) *Cardiovascular Research* 28, 445–455.
Nishida, W., Kitami, Y., and Hiwada, K. (1993) *Gene* 130, 297–302.
Olson, E. N. (1990) *Genes Dev.* 4, 1454–1461.
Olson, E. N. (1993) *Circ. Res.* 72, 1–6.
Olson, E. N. and Klein, W. H. (1994) *Genes Dev.* 8, 1–8.
Orkin, (1990) *Cell,* 63, 665–672.
Owens, G. K., Loeb, A., Gordon, D., and Thompson, M. M. (1986) *J. Cell Biol.* 102, 343–352.
Owens, G. K. (1992) *J. Biol. Chem.* 267, 984–989.
Pardanaud, L., Yassine, F., and Dieterlen Lievre, F. (1989) *Development.* 105, 473–485.
Parmacek et al., (1994) *Mol. Cell. Biol.,* 14, 1870–1885.
Parmacek, M. S., Vora, A. J., Shen, T., Barr, E., Jung, F., and Leiden, J. M. (1992) *Mol. Cell. Biol.* 12, 1967–1976.
Parmacek, M. S., Bengur, A. R., Vora, A. and Leiden, J. M. (1990) *J. Biol. Chem.* 265: 15970–15976.
Parmacek, M. S. and Leiden, J. M. (1989) *J. Biol. Chem.* 264, 13217–13225.
Parmacek, M. S., Ip, H. S., Jung, F., Shen, T., Martin, J. F., Vora, A. J., Olson, E. N., and Pauletto, P., Glukhova, M. A., and Sartore, S. (1993) *J. Vasc. Res.* 30, 279–292.
Poole, T. J. and Coffin, J. D. (1989) *J. Exp. Zool.* 251, 224–231.
Pratusevich, V. R., Seow, C. Y. and Ford, L. E. (1995) *J. Gen. Physiol.* 105, 73–94.
Ross, R. (1993) *Nature* 362, 801–809.
Ross, R. (1993) *Am. J. Pathol.* 143, 987–1002.
Ross, R. (1986) *N Engl. J. Med.* 314, 488–500.
Rovner, A. S., Murphy, R. A. and Owens, G. K. (1986) *J. Biol. Chem.* 261, 14740–14745.
Rudnicki, M. A., Schnegelsberg, P., Stead, R. H., Braun, T., Arnold, H. H. and Jaenisch, R. (1993). *Cell* 75, 1351–1359.
Sawtell, N. M. and Lessard, J. L. (1989) *J. Cell Biol.* 109:2929–2937.
Schwartz, R. S., Holmes, D. R., Topol, E. J. (1992) *J. Am. Coll. Cardiol.* 20, 1284–1293.
Schwartz, S. M., Campell, G. R., and Campbell, J. H. (1986) *Circ. Res.* 58, 427–440.
Seow, C. Y. and Ford, L. E. (1991) *J. Gen Physiol.* 97, 541–560.
Shanahan, C. M., Weissberg, P. L., and Metcalfe, J. C. (1993) *Circ. Res.* 73, 193–204.
Singh et al., (1988) *Cell,* 52, 415–423.
Strasser, P., Gimona, M., Moessler, H., Herzog, M., and Small, J. V. (1992) *Genbank* Direct Submission Accession Number Z19542
Tapscott, S. J. and Weintraub, H. (1991) *J. Clin. Invest.* 87, 1133–1138.
Taubman, M. B., Grant, J. W. and Nadal Ginard, B. (1987) *J. Cell Biol.* 104, 1505–1513.
Tripahy, S. K., Svensson E. C., Black, H. B., Goldwasser, E., Margalith, M., Hobart, P. M. and Leiden, J. M. Long-term expression of erythropoietin in the systemic circulation of mice following intramuscular injection of a plasmid DNA vector. Proc. Natl., Acad. Sci. USA, 1996.
Ueki, N., K. Sobue, K., Kanda, K., Hada, T., and Higashino, K. (1987) *Proc. Natl. Acad. Sci. USA* 84, 9049–9053.
Weintraub, H. (1989) *Cell* 58, 823–831.
Zanellato, A. M. C., Borione, A. C., Tonello, M., Scannapieco, G., Pauletto, P., and Sartore, S. (1990) *Arteriosclerosis* 10, 996–1009.

---

What is claimed is:

1. A method for providing a molecule of interest to a blood vessel in a mammal comprising:
   (a) providing a bioprosthesis seeded with a smooth muscle cell transfected with a nucleic acid segment comprising an SM22α promoter region operably linked to a DNA sequence encoding said molecule of interest that is other than mouse SM22α, wherein the SM22α promoter region has a maximum of 441 bases and comprises:
      (i) bases 900–1340 of SEQ ID NO:1;
      (ii) a sequence hybridizing with the complement of SEQ ID NO:1 under hybridizing conditions comprising 0.02M–0.15M sodium chloride at a temperature of 50° C. to 70° C.;
      (iii) an oligomer comprising SME1 (SEQ ID NO:21), SME2 (SEQ ID NO:23), SME3 (SEQ ID NO:25), SME4 (SEQ ID NO:27), SME5 (SEQ ID NO:31), or SME6 (SEQ ID NO:33); or
      (iv) a sequence that hybridizes with the complement of SME1 (SEQ ID NO:21), SME2 (SEQ ID NO:23), SME3 (SEQ ID NO:25), SME4 (SEQ ID NO:27), SME5 (SEQ ID NO:31), or SME6 (SEQ ID NO:33) under hybridizing conditions comprising 0.02M–0.15M sodium chloride at a temperature of 50° C. to 70° C.;
   (b) placing said seeded prosthesis in said blood vessel; and
   (c) obtaining expression of said molecule in said blood vessel.

2. A method for providing a molecule of interest to a blood vessel in a mammal comprising:
   (a) providing a bioprosthesis seeded with a smooth muscle cell transfected with a nucleic acid segment comprising an SM22α promoter region operably linked to a DNA sequence encoding said molecule of interest that is not mouse SM22α, wherein the SM22α promoter region has a maximum of 441 bases and comprises:
      (i) an oligomer comprising SME1 (SEQ ID NO:21), SME2 (SEQ ID NO:23), SME3 (SEQ ID NO:25), SME4 (SEQ ID NO:27), SME5 (SEQ ID NO:31), or SME6 (SEQ ID NO:33); or
      (ii) a sequence that hybridizes with the complement of SME1 (SEQ ID NO:21), SME2 (SEQ ID NO:23), SME3 (SEQ ID NO:25), SME4 (SEQ ID NO:27), SME5 (SEQ ID NO:31), or SME6 (SEQ ID NO:33) under hybridizing conditions comprising 0.02M–0.15M sodium chloride at a temperature of 50° C. to 70° C.;
   (b) placing said seeded prosthesis in said blood vessel; and
   (c) obtaining expression of said molecule in said blood vessel.

3. The method of claim 1, wherein said bioprosthesis comprises a graft.

4. The method of claim 1, wherein said bioprosthesis comprises a stent.

5. The method of claim 1, comprising the additional step of seeding said bioprosthesis with said transfected cell prior to said step (a).

6. The method of claim 5 comprising the additional step of transfecting said cell with said nucleic acid segment prior to said seeding step.

7. The method of claim 1, wherein the DNA sequence encodes a cell cycle regulator molecule.

8. The method of claim 7, wherein said cell cycle regulatory molecule is competent to inhibit restenosis.

9. The method of claim 7, wherein said cell cycle regulatory molecule is an Rb gene product, a p53, a cell cycle dependent kinase, a CDK kinase, or a cyclin.

10. The method of claim 7, wherein the cell cycle regulatory molecule is a phosphorylation deficient Rb gene product.

11. The method of claim 7, wherein the cell cycle regulatory molecule is a constitutively active Rb gene product.

12. The method of claim 7, wherein the cell cycle regulatory molecule is an RNA antisense molecule.

13. The method of claim 1, wherein the DNA sequence encodes a molecule competent to induce collateral blood vessel formation.

14. The method of claim 1, wherein said molecule is an angiogenesis factor.

15. The method of claim 13 or 14, wherein said molecule is a VEGF protein.

16. The method of claim 1, wherein said DNA sequence encodes a reporter molecule.

17. The method of claim 16, wherein the reporter molecule is β-galactosidase, firefly luciferase, neomycin resistance, dihydrofolate reductase, chloramphenicol acetyl transferase, human immunodeficiency virus gp120, an esterase, a phosphatase, a protease, a tissue plasminogen activator, a urokinase, or a herpes virus gD.

18. The method of claim 1, wherein the blood vessel is an artery.

19. The method of claim 18, wherein said artery is a coronary artery, a renal artery, a peripheral artery, or a carotid artery.

20. The method of claim 1, wherein said blood vessel is a vein.

21. The method of claim 20, wherein said vein is a coronary vein, a renal vein, a peripheral vein, or a jugular vein.

22. The method of claim 1, wherein the nucleic acid segment is transfected in a viral vector.

23. The method of claim 22, wherein the viral vector is a raus sarcoma virus vector, a p21 virus vector, a retrovirus vector, a herpes simplex virus vector, a cytomegalovirus vector.

24. The method of claim 22, wherein the viral vector is an adenovirus vector or an adeno-associated virus vector.

25. The method of claim 22, wherein the viral vector is replication-deficient.

26. A method of preparing a bioprosthesis competent to deliver a molecule of interest to a blood vessel in a mammal, comprising:
   (a) providing a bioprosthesis, and
   (b) seeding said bioprosthesis with a smooth muscle cell transfected with a nucleic acid segment comprising an SM22α promoter region operably linked to a DNA sequence encoding said molecule of interest that is other than mouse SM22α, wherein the SM22α promoter region has a maximum of 441 bases and comprises:
      (i) bases 900–1340 of SEQ ID NO:1;
      (ii) a sequence hybridizing with the complement of SEQ ID NO:1 under hybridizing conditions comprising 0.02M–0.15M sodium chloride at a temperature of 50° C. to 70° C.;
      (iii) an oligomer comprising SME1 (SEQ ID NO:21), SME2 (SEQ ID NO:23), SME3 (SEQ ID NO:25), SME4 (SEQ ID NO:27), SME5 (SEQ ID NO:31), or SME6 (SEQ ID NO:33); or
      (iv) a sequence that hybridizes with the complement of SME1 (SEQ ID NO:21), SME2 (SEQ ID NO:23), SME3 (SEQ ID NO:25), SME4 (SEQ ID NO:27), SME5 (SEQ ID NO:31), or SME6 (SEQ ID NO:33) under hybridizing conditions comprising 0.02M–0.15M sodium chloride at a temperature of 50° C. to 70° C.

27. The method of claim 26, wherein said bioprosthesis comprises a graft.

28. The method of claim 26, wherein said bioprosthesis comprises a stent.

29. The method of claim 26, wherein said molecule is competent to inhibit restenosis.

30. The method of claim 29, wherein said molecule is a cell cycle regulatory molecule.

31. The method of claim 30, wherein said molecule is an Rb gene product, a p53, a cell cycle dependent kinase, a CDK kinase, or a cyclin.

32. The method of claim 29, wherein said molecule is an antisense molecule.

33. The method of claim 29, wherein said molecule is an angiogenic factor.

34. The method of claim 33, wherein said factor is a VEGF protein.

35. A kit for making a seeded bioprosthesis comprising:
   (a) a nucleic acid segment comprising an SM22α promoter region operably linked to a gene other than mouse SM22α, wherein the SM22α promoter region has a maximum of 441 bases and comprises:
      (i) bases 900–1340 of SEQ ID NO:1;
      (ii) a sequence hybridizing with the complement of SEQ ID NO:1 under hybridizing conditions comprising 0.02M–0.15M sodium chloride at a temperature of 50° C. to 70° C.;
      (iii) an oligomer comprising SME1 (SEQ ID NO:21), SME2 (SEQ ID NO:23), SME3 (SEQ ID NO:25), SME4 (SEQ ID NO:27), SME5 (SEQ ID NO:31), or SME6 (SEQ ID NO:33); or
      (iv) a sequence that hybridizes with the complement of SME1 (SEQ ID NO:21), SME2 (SEQ ID NO:23), SME3 (SEQ ID NO:25), SME4 (SEQ ID NO:27), SME5 (SEQ ID NO:31), or SME6 (SEQ ID NO:33) under hybridizing conditions comprising 0.02M–0.15M sodium chloride at a temperature of 50° C. to 70° C.; and
   (b) a bioprosthesis competent to receive said nucleic acid segment.

36. A bioprosthesis comprising, on a surface thereof, a smooth muscle cell transfected with a nucleic acid segment comprising an SM22α promoter region operably linked to a DNA sequence encoding a molecule other than mouse SM22α, wherein the SM22α promoter region has a maximum of 441 bases and comprises:
   (i) bases 900–1340 of SEQ ID NO:1;
   (ii) a sequence hybridizing with the complement of SEQ ID NO:1 under hybridizing conditions comprising 0.02M–0.15M sodium chloride at a temperature of 50° C. to 70° C.;
   (iii) an oligomer comprising SME1 (SEQ ID NO:21), SME2 (SEQ ID NO:23), SME3 (SEQ ID NO:25), SME4 (SEQ ID NO:27), SME5 (SEQ ID NO:31), or SME6 (SEQ ID NO:33); or
   (iv) a sequence that hybridizes with the complement of SME1 (SEQ ID NO:21), SME2 (SEQ ID NO:23), SME3 (SEQ ID NO:25), SME4 (SEQ ID NO:27), SME5 (SEQ ID NO:31), or SME6 (SEQ ID NO:33) under hybridizing conditions comprising 0.02M–0.15M sodium chloride at a temperature of 50° C. to 70° C.

37. The kit of claim 35, wherein said bioprosthesis comprises a graft.

38. The kit of claim 35, wherein said bioprosthesis comprises a stent.

39. The kit of claim 35, wherein the DNA sequence encodes a cell cycle regulatory molecule.

40. The kit of claim 39, wherein said cell cycle regulatory molecule is competent to inhibit restenosis.

41. The kit of claim 39, wherein said cell cycle regulatory molecule is an Rb gene product, a p53, a cell cycle dependent kinase, a CDK kinase, or a cyclin.

42. The kit of claim 39, wherein the cell cycle regulatory molecule is a phosphorylation deficient Rb gene product.

43. The kit of claim 39, wherein the cell cycle regulatory gene is a constitutively active Rb gene product.

44. The kit of claim 39, wherein the cell cycle regulatory molecule is an RNA antisense molecule.

45. The kit of claim 35, wherein the DNA sequence encodes a molecule competent to induce collateral blood vessel formation.

46. The kit of claim 45, wherein said molecule is an angiogenesis factor.

47. The kit of claim 46, wherein said factor is a VEGF protein.

48. The kit of claim 35, wherein said DNA sequence encodes a reporter molecule.

49. The kit of claim 35, wherein the reporter molecule is β-galactosidase, firefly luciferase, neomycin resistance, dihydrofolate reductase, chloramphenicol acetyl transferase, human immunodeficiency virus gp120, an esterase, a phosphatase, a protease, a tissue plasminogen activator, a urokinase, or a herpes virus gD.

50. The method of claim 38, wherein the blood vessel is an artery.

51. The method of claim 50, wherein said artery is a coronary artery, a renal artery, a peripheral artery, or a carotid artery.

52. The method of claim 2, wherein said blood vessel is a vein.

53. The method of claim 52, wherein said vein is a coronary vein, a renal vein, a peripheral vein, or a jugular vein.

54. The kit of claim 35, wherein the nucleic acid segment is comprised in a viral vector.

55. The kit of claim 54, wherein the viral vector is a raus sarcoma virus vector, a p21 virus vector, a retrovirus vector, a herpes simplex virus vector, a cytomegalovirus vector.

56. The kit of claim 54, wherein the viral vector is an adenovirus vector or an adeno-associated virus vector.

57. The kit of claim 54, wherein the viral vector is replication-deficient.

58. The bioprosthesis of claim 36, wherein said bioprosthesis comprises a graft.

59. The bioprosthesis of claim 36, wherein said bioprosthesis comprises a stent.

60. The bioprosthesis of claim 36, wherein the DNA sequence encodes a cell cycle regulatory molecule.

61. The bioprosthesis of claim 60, wherein said cell cycle regulatory molecule is competent to inhibit restenosis.

62. The bioprosthesis of claim 60, wherein said cell cycle regulatory molecule is an Rb gene product, a p53, a cell cycle dependent kinase, a CDK kinase, or a cyclin.

63. The bioprosthesis of claim 60, wherein the cell cycle regulatory molecule is a phosphorylation deficient Rb gene product.

64. The bioprosthesis of claim 60, wherein the cell cycle regulatory gene is a constitutively active Rb gene product.

65. The bioprosthesis of claim 60, wherein the cell cycle regulatory molecule is an RNA antisense molecule.

66. The bioprosthesis of claim 36, wherein the DNA sequence encodes a molecule competent to induce collateral blood vessel formation.

67. The bioprosthesis of claim 66, wherein said molecule is an angiogenesis factor.

68. The bioprosthesis of claim 67, wherein said factor is VEGF protein.

69. The bioprosthesis of claim 36, wherein said DNA sequence encodes a reporter molecule.

70. The bioprosthesis of claim 36, wherein the reporter molecule is β-galactosidase, firefly luciferase, neomycin resistance, dihydrofolate reductase, chloramphenicol acetyl transferase, human immunodeficiency virus gp120, an esterase, a phosphatase, a protease, a tissue plasminogen activator, a urokinase, or a herpes virus gD.

71. The bioprosthesis of claim 36, wherein the nucleic acid segment is comprised in a viral vector.

72. The bioprosthesis of claim 71, wherein the viral vector is a raus sarcoma virus vector, a p21 virus vector, a retrovirus vector, a herpes simplex virus vector, a cytomegalovirus vector.

73. The bioprosthesis of claim 71, wherein the viral vector is an adenovirus vector or an adeno-associated virus vector.

74. The bioprosthesis of claim 71, wherein the viral vector is replication-deficient.

75. The method of claim 2, wherein the SM22α promoter region has a maximum of 441 bases and comprises (c) bases 900–1340 of SEQ ID NO:1, or (d) a sequence hybridizing with the complement of SEQ ID NO:1 under conditions comprising 0.02M–0.15 M sodium chloride at a temperature of 50° C. to 70° C.

* * * * *

UNITED STATES PATENT AND TRADEMARK OFFICE
CERTIFICATE OF CORRECTION

PATENT NO. : 6,331,527 B1
DATED : December 18, 2001
INVENTOR(S) : Parmacek et al.

It is certified that error appears in the above-identified patent and that said Letters Patent is hereby corrected as shown below:

Title page,
Item [54], please delete "PROMOTER" and insert -- PROMOTER FOR -- therefor.

Column 87,
Line 20, please delete "a cytomegalovirus" and insert -- or a cytomegalovirus -- therefor.

Column 89,
Line 27, please delete "a cytomegalovirus" and insert -- or a cytomegalovirus -- therefor.

Column 90,
Line 28, please delete "a cytomegalovirus" and insert -- or a cytomegalovirus -- therefor.

Signed and Sealed this

Tenth Day of September, 2002

Attest:

Attesting Officer

JAMES E. ROGAN
Director of the United States Patent and Trademark Office

SEQUENCE LISTING

<160> NUMBER OF SEQ ID NOS: 55

<210> SEQ ID NO 1
<211> LENGTH: 1419
<212> TYPE: DNA
<213> ORGANISM: Mus musculus

<400> SEQUENCE: 1

```
gaattcagga cgtaatcagt ggctggaaag caagagctct agaggagctc cagcttatta      60
tgacccttcc ttcagatgcc acaaggaggt gctggagttc tatgcaccaa tagcttaaac     120
cagccaggct ggctgtagtg gattgagcgt ctgaggctgc acctctctgg cctgcagcca     180
gttctgggtg agactgaccc tgcctgaggg ttctctcctt ccctctctct actcctttct     240
```

-continued

```
ccctctccct ctccctctct ctgtttcctg aggtttccag gattggggat gggactcaga      300
gacaccacta aagccttacc ttttaagaag ttgcattcag tgagtgtgtg agacatagca      360
cagatagggg cagaggagag ctggttctgt ctccactgtg tttggtcttg ggtactgaac      420
tcagaccatc aggtgtgata gcagttgtct ttaaccctaa ccctgagcct gtctcacctg      480
tcccttccca agaccactga agctaggtgc aagataagtg gggacccttt ctgaggtggt      540
aggatctttc acgataagga ctattttgaa gggagggagg gtgacactgt cctagtcctc      600
ttaccctagt gtctccagcc ttgccaggcc ttaaacatcc gcccattgtc accgctctag      660 aagggggccag ggttgacttg ctgctaaaca aggcactccc tagagaagca cccgctagaa      720
gcataccata cctgtgggca ggatgaccca tgttctgcca cgcacttggt agccttggaa      780
aggccacttt gaacctcaat tttctcaact gttaaatggg gtggtaactg ctatctcata      840
ataaagggga acgtgaaagg aaggcgtttg catagtgcct ggttgtgcag ccaggctgca      900
gtcaagacta gttcccacca actcgatttt aaagccttgc aagaaggtgg cttgtttgtc      960
ccttgcaggt tcctttgtcg ggccaaactc tagaatgcct cccctttct ttctcattga      1020 agagcagacc caagtccggg taacaaggaa gggtttcagg gtcctgccca taaaaggttt      1080
ttcccggccg ccctcagcac cgccccgccc cgaccccgc agcatctcca aagcatgcag      1140
agaatgtctc cggctgcccc cgacagactg ctccaacttg gtgtctttcc ccaaatatgg      1200
agcctgtgtg gagtgagtgg ggcggcccgg ggtggtgagc caagcagact tccatgggca      1260
gggaggggcg ccagcggacg gcagagggt gacatcactg cctaggcggc cttaaaccc      1320 ctcacccagc cggcgcccca gcccgtctgc cccagcccag acaccgaagc tactctcctt      1380
ccagtccaca aacgaccaag ccttgtaagt gcaagtcat                              1419
```

<210> SEQ ID NO 2
<211> LENGTH: 991
<212> TYPE: DNA
<213> ORGANISM: Mus musculus
<220> FEATURE:
<221> NAME/KEY: CDS
<222> LOCATION: (38)..(218)
<220> FEATURE:
<221> NAME/KEY: CDS
<222> LOCATION: (322)..(500)
<220> FEATURE:
<221> NAME/KEY: CDS
<222> LOCATION: (866)..(967)

<400> SEQUENCE: 2

```
cttttctcca cactctatac tttagctctg cctcaac atg gcc aac aag ggt cca      55
                                         Met Ala Asn Lys Gly Pro
                                          1               5 tcc tac ggc atg agc cga gaa gtg cag tcc aaa att gag aag aag tat      103
Ser Tyr Gly Met Ser Arg Glu Val Gln Ser Lys Ile Glu Lys Lys Tyr
         10                  15                  20 gac gag gag ctg gag gag cga cta gtg gag tgg att gta gtg cag tgt      151
Asp Glu Glu Leu Glu Glu Arg Leu Val Glu Trp Ile Val Val Gln Cys
     25                  30                  35 ggc cct gat gta ggc cgc cca gat cgt ggg cgc ctg ggc ttc cag gtg      199
Gly Pro Asp Val Gly Arg Pro Asp Arg Gly Arg Leu Gly Phe Gln Val
 40                  45                  50 tgg ctg aag aat ggt gtg g tgagtaaccc ttgcgaaggg aatctaggga            248
Trp Leu Lys Asn Gly Val
 55              60 tgtgtatgcc gccctacaaa ctgtgagaca gactccctga gctgagtgtt cagttgtgtt    308
```

```
ctgtacctgg cag att ctg agc aaa ttg gtg aac agc ctg tat cct gag         357
            Ile Leu Ser Lys Leu Val Asn Ser Leu Tyr Pro Glu
              1               5                  10 gga tcg aag cca gtg aag gtg cct gag aac cca ccc tcc atg gtc ttt        405
Gly Ser Lys Pro Val Lys Val Pro Glu Asn Pro Pro Ser Met Val Phe
         15                  20                  25 aag cag atg gaa cag gtg gct caa ttc ttg aag gca gct gaa gat tat        453
Lys Gln Met Glu Gln Val Ala Gln Phe Leu Lys Ala Ala Glu Asp Tyr
     30                  35                  40 gga gtc atc aag act gac atg ttc cag act gtt gac ctc tat gaa gg         500
Gly Val Ile Lys Thr Asp Met Phe Gln Thr Val Asp Leu Tyr Glu
 45                  50                  55 tataaggaaa aagggctgg agccagtggg cgagtggaga gcaagattat cagtcaagga      560
gaaggaatat caaaagccac aaccagctct gttgatgtgt tcatagcagg aatgggatat    620
gccaagagaa cacatagcaa ggggaccagc ttggtggtac agcatttcct tctgggtaca    680
agggcctgtt ttggatccta gaatatcaaa tatataccac accatactca ctagggttta    740
gaatatggtc tcttgaaccc tcttgatttg gtgccacttg ctccttggtt ggaccatttt    800
tgaagctggg caggtattgc ctatatggtc ctgaaattag ctccctggcc actcttctca    860 taggt aag gat atg gca gca gtg cag agg act cta atg gct ttg ggc         907
      Lys Asp Met Ala Ala Val Gln Arg Thr Leu Met Ala Leu Gly
        1               5                  10 agt ttg gct gtg acc aaa aac gat gga aac tac cgt gga gat ccc aac       955
Ser Leu Ala Val Thr Lys Asn Asp Gly Asn Tyr Arg Gly Asp Pro Asn
 15                  20                  25                  30 tgg ttt atg aag tatgtgtcca ctgggtctct ctgt                            991
Trp Phe Met Lys
```

<210> SEQ ID NO 3
<211> LENGTH: 60
<212> TYPE: PRT
<213> ORGANISM: Mus musculus

<400> SEQUENCE: 3

```
Met Ala Asn Lys Gly Pro Ser Tyr Gly Met Ser Arg Glu Val Gln Ser
  1               5                  10                  15

Lys Ile Glu Lys Lys Tyr Asp Glu Glu Leu Glu Glu Arg Leu Val Glu
             20                  25                  30

Trp Ile Val Val Gln Cys Gly Pro Asp Val Gly Arg Pro Asp Arg Gly
         35                  40                  45

Arg Leu Gly Phe Gln Val Trp Leu Lys Asn Gly Val
     50                  55                  60
```

<210> SEQ ID NO 4
<211> LENGTH: 59
<212> TYPE: PRT
<213> ORGANISM: Mus musculus

<400> SEQUENCE: 4

```
Ile Leu Ser Lys Leu Val Asn Ser Leu Tyr Pro Glu Gly Ser Lys Pro
  1               5                  10                  15

Val Lys Val Pro Glu Asn Pro Pro Ser Met Val Phe Lys Gln Met Glu
             20                  25                  30

Gln Val Ala Gln Phe Leu Lys Ala Ala Glu Asp Tyr Gly Val Ile Lys
         35                  40                  45

Thr Asp Met Phe Gln Thr Val Asp Leu Tyr Glu
     50                  55
```

<210> SEQ ID NO 5
<211> LENGTH: 34
<212> TYPE: PRT
<213> ORGANISM: Mus musculus

<400> SEQUENCE: 5

Lys Asp Met Ala Ala Val Gln Arg Thr Leu Met Ala Leu Gly Ser Leu
1               5                   10                  15

Ala Val Thr Lys Asn Asp Gly Asn Tyr Arg Gly Asp Pro Asn Trp Phe
            20                  25                  30

Met Lys

<210> SEQ ID NO 6
<211> LENGTH: 575
<212> TYPE: DNA
<213> ORGANISM: Mus musculus
<220> FEATURE:
<221> NAME/KEY: CDS
<222> LOCATION: (28)..(169)

<400> SEQUENCE: 6
acttaccctg gttccttttc ttctagg aaa gcc cag gag cat aag agg gac        51
                            Lys Ala Gln Glu His Lys Arg Asp
                             1               5 ttc aca gac agc caa ctg cag gag ggg aag cac gtc att ggc ctt caa     99
Phe Thr Asp Ser Gln Leu Gln Glu Gly Lys His Val Ile Gly Leu Gln
     10                  15                  20 atg ggc agc aac aga gga gcc tcg cag gct ggc atg aca ggc tat ggg    147
Met Gly Ser Asn Arg Gly Ala Ser Gln Ala Gly Met Thr Gly Tyr Gly
 25                  30                  35                  40 cga ccc cgg cag atc atc agt t agaaagggaa ggccagccct gagctgcagc    199
Arg Pro Arg Gln Ile Ile Ser
                45 atcctgctta gcctgcctca caaatgccta tgtaggttct tagccctgac agctctgagg    259 tgtcactggg caaagatgac tgcacatggg cagctcccac ctatccttag cctcagccca    319 gcatcttacc ccagagccac cactgccctg gcccctgttc ccagctgtac ccccacctct    379 actgttcctc tcatcctgga gtaagcaggg agaagtgggc tggggtagct ggctgtaggc    439 cagcccactg tccttgatat cgaatgtcct ttgaaggaga cccagcccag cctctacatc    499 ttttcctgga atatgttttt gggttgaaat tcaaaaagga aaaagaaaa atatataaat    559 atatatatat atatac                                                    575

<210> SEQ ID NO 7
<211> LENGTH: 47
<212> TYPE: PRT
<213> ORGANISM: Mus musculus

<400> SEQUENCE: 7

Lys Ala Gln Glu His Lys Arg Asp Phe Thr Asp Ser Gln Leu Gln Glu
1               5                   10                  15

Gly Lys His Val Ile Gly Leu Gln Met Gly Ser Asn Arg Gly Ala Ser
            20                  25                  30

Gln Ala Gly Met Thr Gly Tyr Gly Arg Pro Arg Gln Ile Ile Ser
        35                  40                  45

<210> SEQ ID NO 8
<211> LENGTH: 1102
<212> TYPE: DNA
<213> ORGANISM: Mus musculus

<220> FEATURE:
<221> NAME/KEY: CDS
<222> LOCATION: (77)..(681)

<400> SEQUENCE: 8

```
gcccgtctgc cccagcccag acaccgaagc tactctcctt ccagtccaca aacgaccaag      60
ccttctctgc tcaac atg gcc aac aag ggt cca tcc tac ggc atg agc cga     112
              Met Ala Asn Lys Gly Pro Ser Tyr Gly Met Ser Arg
                1               5                  10 gaa gtg cag tcc aaa att gag aag aag tat gac gag gag ctg gag gag     160
Glu Val Gln Ser Lys Ile Glu Lys Lys Tyr Asp Glu Glu Leu Glu Glu
         15                  20                  25 cga cta gtg gag tgg att gta gtg cag tgt ggc cct gat gta ggc cgc     208
Arg Leu Val Glu Trp Ile Val Val Gln Cys Gly Pro Asp Val Gly Arg
 30                  35                  40 cca gat cgt ggg cgc ctg ggc ttc cag gtg tgg ctg aag aat ggt gtg     256
Pro Asp Arg Gly Arg Leu Gly Phe Gln Val Trp Leu Lys Asn Gly Val
 45                  50                  55                  60 att ctg agc aaa ttg gtg aac agc ctg tat cct gag gga tcg aag cca     304
Ile Leu Ser Lys Leu Val Asn Ser Leu Tyr Pro Glu Gly Ser Lys Pro
                 65                  70                  75 gtg aag gtg cct gag aac cca ccc tcc atg gtc ttt aag cag atg gaa     352
Val Lys Val Pro Glu Asn Pro Pro Ser Met Val Phe Lys Gln Met Glu
             80                  85                  90 cag gtg gct caa ttc ttg aag gca gct gaa gat tat gga gtc atc aag     400
Gln Val Ala Gln Phe Leu Lys Ala Ala Glu Asp Tyr Gly Val Ile Lys
         95                 100                 105 act gac atg ttc cag act gtt gac ctc tat gaa ggt aag gat atg gca     448
Thr Asp Met Phe Gln Thr Val Asp Leu Tyr Glu Gly Lys Asp Met Ala
    110                 115                 120 gca gtg cag agg act cta atg gct ttg ggc agt ttg gct gtg acc aaa     496
Ala Val Gln Arg Thr Leu Met Ala Leu Gly Ser Leu Ala Val Thr Lys
125                 130                 135                 140 aac gat gga aac tac cgt gga gat ccc aac tgg ttt atg aag aaa gcc     544
Asn Asp Gly Asn Tyr Arg Gly Asp Pro Asn Trp Phe Met Lys Lys Ala
                145                 150                 155 cag gag cat aag agg gac ttc aca gac agc caa ctg cag gag ggg aag     592
Gln Glu His Lys Arg Asp Phe Thr Asp Ser Gln Leu Gln Glu Gly Lys
            160                 165                 170 cac gtc att ggc ctt caa atg ggc agc aac aga gga gcc tcg cag gct     640
His Val Ile Gly Leu Gln Met Gly Ser Asn Arg Gly Ala Ser Gln Ala
        175                 180                 185 ggc atg aca ggc tat ggg cga ccc cgg cag atc atc agt tagaaaggga     689
Gly Met Thr Gly Tyr Gly Arg Pro Arg Gln Ile Ile Ser
    190                 195                 200 aggccagccc tgagctgcag catcctgctt agcctgcctc acaaatgcct atgtaggttc    749
ttagccctga cagctctgag gtgtcactgg caaagatga ctgcacatgg gcagctccca     809
cctatcctta gcctcagccc agcatcttac cccagagcca ccactgccct ggcccctgtt    869
cccagctgta cccccacctc tactgttcct ctcatcctgg agtaagcagg gagaagtggg    929
ctggggtagc tggctgtagg ccagcccact gtccttgata tcgaatgtcc tttgaaggag    989
acccagccca gcctctacat cttttcctgg aatatgtttt tgggttgaaa ttcaaaaagg   1049
aaaaaagaaa aatatataaa tatatatata tacaaaaaaa aaaaaaaaaa aaa          1102
```

<210> SEQ ID NO 9
<211> LENGTH: 201
<212> TYPE: PRT
<213> ORGANISM: Mus musculus

<400> SEQUENCE: 9

| Met | Ala | Asn | Lys | Gly | Pro | Ser | Tyr | Gly | Met | Ser | Arg | Glu | Val | Gln | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Lys Ile Glu Lys Lys Tyr Asp Glu Glu Leu Glu Arg Leu Val Glu
          20                  25                  30

Trp Ile Val Val Gln Cys Gly Pro Asp Val Gly Arg Pro Asp Arg Gly
              35                  40                  45

Arg Leu Gly Phe Gln Val Trp Leu Lys Asn Gly Val Ile Leu Ser Lys
    50                  55                  60

Leu Val Asn Ser Leu Tyr Pro Glu Gly Ser Lys Pro Val Lys Val Pro
65                  70                  75                  80

Glu Asn Pro Pro Ser Met Val Phe Lys Gln Met Glu Gln Val Ala Gln
                85                  90                  95

Phe Leu Lys Ala Ala Glu Asp Tyr Gly Val Ile Lys Thr Asp Met Phe
            100                 105                 110

Gln Thr Val Asp Leu Tyr Glu Gly Lys Asp Met Ala Ala Val Gln Arg
        115                 120                 125

Thr Leu Met Ala Leu Gly Ser Leu Ala Val Thr Lys Asn Asp Gly Asn
130                 135                 140

Tyr Arg Gly Asp Pro Asn Trp Phe Met Lys Lys Ala Gln Glu His Lys
145                 150                 155                 160

Arg Asp Phe Thr Asp Ser Gln Leu Gln Glu Gly Lys His Val Ile Gly
                165                 170                 175

Leu Gln Met Gly Ser Asn Arg Gly Ala Ser Gln Ala Gly Met Thr Gly
            180                 185                 190

Tyr Gly Arg Pro Arg Gln Ile Ile Ser
        195                 200

```
<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 10
atcgaattcc gctactctcc ttccagccca caaacgacca agc                         43

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 11
atcaagcttg gtgggagctg cccatgtgca gtc                                    33

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 12
```

```
tgccgtagga tggacccttg ttggc                                           25
```

```
<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (1)
<223> OTHER INFORMATION: Y = C or T/U
<220> FEATURE:
<221> NAME/KEY: modified_base
<222> LOCATION: (4)
<223> OTHER INFORMATION: W = A or T/U
<220> FEATURE:
<221> NAME/KEY: modified_base
<222> LOCATION: (10)
<223> OTHER INFORMATION: R = A or G

<400> SEQUENCE: 13 ytawaaatar                                                            10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 14
tttaaaatcg                                                            10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 15
ttcaaaatag                                                            10

<210> SEQ ID NO 16
<211> LENGTH: 8
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (4)
<223> OTHER INFORMATION: M = A or C
<220> FEATURE:
<221> NAME/KEY: modified_base
<222> LOCATION: (5)
<223> OTHER INFORMATION: N= A or C or G or T/U
<220> FEATURE:
<221> NAME/KEY: modified_base
<222> LOCATION: (6-8)
<223> OTHER INFORMATION: S = G or C

<400> SEQUENCE: 16 cccmnsss                                                               8
```

```
<210> SEQ ID NO 17
<211> LENGTH: 9
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (1)
<223> OTHER INFORMATION: K = G or T/U
<220> FEATURE:
<221> NAME/KEY: modified_base
<222> LOCATION: (2)
<223> OTHER INFORMATION: R = A or G
<220> FEATURE:
<221> NAME/KEY: modified_base
<222> LOCATION: (6)
<223> OTHER INFORMATION: K = G or T/U
<220> FEATURE:
<221> NAME/KEY: modified_base
<222> LOCATION: (7-8)
<223> OTHER INFORMATION: R = A or G
<220> FEATURE:
<221> NAME/KEY: modified_base
<222> LOCATION: (9)
<223> OTHER INFORMATION: K = G or T/U

<400> SEQUENCE: 17 krggckrrk                                                              9

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (2)
<223> OTHER INFORMATION: K = G or T/U
<220> FEATURE:
<221> NAME/KEY: modified_base
<222> LOCATION: (3-4)
<223> OTHER INFORMATION: N = A or C or G or T/U
<220> FEATURE:
<221> NAME/KEY: modified_base
<222> LOCATION: (6)
<223> OTHER INFORMATION: N = A or C or G or T/U
<220> FEATURE:
<221> NAME/KEY: modified_base
<222> LOCATION: (9)
<223> OTHER INFORMATION: K = G or T/U

<400> SEQUENCE: 18 tknngnaak                                                              9

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Met Ile Arg Ile Cys Arg Lys Lys
 1               5

<210> SEQ ID NO 20
<211> LENGTH: 381
<212> TYPE: DNA
```

<213> ORGANISM: Mus musculus

<400> SEQUENCE: 20

```
agtcaagact agttcccacc aactcgattt taaagccttg caagaaggtg gcttgtttgt      60
cccttgcagg ttcctttgtc gggccaaact ctagaatgcc tccccctttc tttctcattg     120
aagagcagac ccaagtccgg gtaacaagga agggtttcag ggtcctgccc ataaaaggtt     180
tttcccggcc gccctcagca ccgccccgcc ccgaccccg cagcatctcc aaagcatgca      240
gagaatgtct ccggctgccc ccgacagact gctccaactt ggtgtctttc cccaaatatg     300
gagcctgtgt ggagtgagtg gggcggcccg gggtggtgag ccaagcagac ttccatgggc     360
agggaggggc gccagcggac g                                                381
```

<210> SEQ ID NO 21
<211> LENGTH: 47
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21

```
aaggaagggt tcagggtcc tgcccataaa aggtttttcc cggccgc                     47
```

<210> SEQ ID NO 22
<211> LENGTH: 47
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22

```
aaggaagggt tcagggtcc tgcccataga tcttttttcc cggccgc                     47
```

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23

```
ccgccctcag caccgccccg ccccgaggcc cgcagcatgt ccg                        43
```

<210> SEQ ID NO 24
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24

```
ccgccctcag caccgcggat ccccgacccc cgcagcatct ccg                        43
```

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer
```

<400> SEQUENCE: 25
ctccaaagca tgcagagaat gtctccggct gcccccg          37

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
ctcggatcca tgctagcaat gaattcggct gcccccg          37

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
tccaacttgg tgtctttccc caaatatgga gcctgtgtgg agtg          44

<210> SEQ ID NO 28
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
tccaacttgg tgtctttccc caaggatcca gcctgtgtgg agtg          44

<210> SEQ ID NO 29
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
tccaacttgg tgtctttccc cggatatgga gcctgtgtgg agtg          44

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
tccaacttgg tgtctttccc caaattagga gcctgtgtgg agtg          44

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
gggcagggag gggcgccagc g                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
gggcaggtac cgaattcagc g                                              21

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
ggacggcaga ggggtgacat cactgcctag gcggccg                             37

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
ggacggcaga ggggatccat gcctgcctag gcggccg                             37

<210> SEQ ID NO 35
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 35
ggacggcaga ggggatccat cactgcctag gcggccg                             37

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
ctggctaaag gggcggggct tggccagcc                                      29

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37

```
ctcccatttc catgacgtca tggtta                                          26
```

<210> SEQ ID NO 38
<211> LENGTH: 47
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38

```
aaggaagggt ttcagggtcc tgcccataga tcttttttcc cggccgc                   47
```

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39

```
ccgccctcag caccgcggat ccccgacccc cgcagcatct ccg                       43
```

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40

```
ctcggatcca tgctagcaat gaattcggct gcccccg                              37
```

<210> SEQ ID NO 41
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41

```
tccaacttgg tgtctttccc caaggatcca gcctgtgtgg agtg                      44
```

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42

```
tccaacttgg tgtctttccc cggatatgga gcctgtgtgg agtg                      44
```

<210> SEQ ID NO 43
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43

```
tccaacttgg tgtctttccc caaattagga gcctgtgtgg agtg                      44
```

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
gggcaggtac cgaattcagc g                                              21

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 45
ggacggcaga ggggatccat gcctgcctag gcggccg                             37

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
ggacggcaga ggggatccat cactgcctag gcggccg                             37

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (3)..(8)
<223> OTHER INFORMATION: W = A or T

<400> SEQUENCE: 47 ccwwwwwwcc                                                           10

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48
ctccaacttg gtgtctttcc ccggatatgg agcctgtgtg gagtg                    45

<210> SEQ ID NO 49
<211> LENGTH: 45
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 49
ctccaacttg gtgtctttcc ccaaattagg agcctgtgtg gagtg                              45

<210> SEQ ID NO 50
<211> LENGTH: 10
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 50
ccaaatatgg                                                                    10

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 51
ccatatatgg                                                                    10

<210> SEQ ID NO 52
<211> LENGTH: 441
<212> TYPE: DNA
<213> ORGANISM: Mus musculus

<400> SEQUENCE: 52
agtcaagact agttcccacc aactcgattt taaagccttg caagaaggtg gcttgtttgt             60
cccttgcagg ttcctttgtc gggccaaact ctagaatgcc tcccccttc tttctcattg             120 aagagcagac ccaagtccgg gtaacaagga agggtttcag ggtcctgccc ataaaaggtt            180
tttcccggcc gccctcagca ccgccccgcc ccgaccccg cagcatctcc aaagcatgca             240
gagaatgtct ccggctgccc ccgacagact gctccaactt ggtgtctttc cccaaatatg            300
gagcctgtgt ggagtgagtg gggcggcccg gggtggtgag ccaagcagac ttccatgggc            360
agggaggggc gccagcggac ggcagagggg tgacatcact gcctaggcgg cctttaaacc            420
cctcacccag ccggcgcccc a                                                      441

<210> SEQ ID NO 53
<211> LENGTH: 441
<212> TYPE: DNA
<213> ORGANISM: Mus musculus

<400> SEQUENCE: 53
tggggcgccg gctgggtgag gggtttaaag gccgcctagg cagtgatgtc acccctctgc            60
cgtccgctgg cgcccctccc tgcccatgga agtctgcttg gctcaccacc ccgggccgcc            120
ccactcactc cacacaggct ccatatttgg ggaaagacac caagttggag cagtctgtcg            180
ggggcagccg gagacattct ctgcatgctt tggagatgct gcggggtcg ggcggggcg              240 gtgctgaggg cggccgggaa aaaccttta tgggcaggac cctgaaaccc ttccttgtta            300
cccggacttg ggtctgctct tcaatgagaa agaaggggg aggcattcta gagtttggcc             360
cgacaaagga acctgcaagg gacaaacaag ccaccttctt gcaaggcttt aaaatcgagt            420
tggtgggaac tagtcttgac t                                                      441
```

```
<210> SEQ ID NO 54
<211> LENGTH: 47
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 54
ctgcagtcaa gactagttcc caccaactcg attttaaagc cttgcaa                    47

<210> SEQ ID NO 55
<211> LENGTH: 47
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 55
ttgcaaggct ttaaaatcga gttggtggga actagtcttg actgcag                    47
```